(12) United States Patent
Murakoshi et al.

(10) Patent No.: US 8,530,204 B2
(45) Date of Patent: Sep. 10, 2013

(54) METHOD FOR PRODUCING CARBOXYLIC ACID USING METHANOL-ASSIMILATING BACTERIUM

(75) Inventors: Yuriko Murakoshi, Kawasaki (JP); Kohei Ishikawa, Kawasaki (JP); Kazuya Kondo, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 166 days.

(21) Appl. No.: 12/241,293

(22) Filed: Sep. 30, 2008

(65) Prior Publication Data

US 2009/0142814 A1 Jun. 4, 2009

Related U.S. Application Data

(63) Continuation of application No. PCT/JP2007/057524, filed on Mar. 28, 2007.

(30) Foreign Application Priority Data

Mar. 30, 2006 (JP) .................................. 2006-095207

(51) Int. Cl.
| | |
|---|---|
| *C12P 13/04* | (2006.01) |
| *C12P 13/08* | (2006.01) |
| *C12N 9/00* | (2006.01) |
| *C12N 1/20* | (2006.01) |
| *C12N 15/00* | (2006.01) |
| *C07H 21/04* | (2006.01) |

(52) U.S. Cl.
USPC ........ 435/115; 435/106; 435/183; 435/252.3; 435/320.1; 536/23.2

(58) Field of Classification Search
None
See application file for complete search history.

(56) References Cited

U.S. PATENT DOCUMENTS

| | | | |
|---|---|---|---|
| 6,110,713 A * | 8/2000 | Hanson et al. ................. | 435/110 |
| 7,026,149 B2 | 4/2006 | Usuda et al. | |
| 7,029,893 B2 | 4/2006 | Usuda et al. | |
| 7,060,475 B2 | 6/2006 | Usuda et al. | |
| 7,163,810 B2 | 1/2007 | Yasueda et al. | |
| 7,211,416 B2 | 5/2007 | Asahara et al. | |
| 7,217,543 B2 | 5/2007 | Gunji et al. | |
| 7,223,572 B1 | 5/2007 | Gunji et al. | |
| 7,335,506 B2 | 2/2008 | Gunji et al. | |
| 2002/0061578 A1 | 5/2002 | Kato et al. | |
| 2003/0049805 A1 | 3/2003 | Nagase et al. | |
| 2003/0124687 A1 * | 7/2003 | Gunji et al. ................. | 435/115 |
| 2003/0232338 A1 | 12/2003 | Usuda et al. | |
| 2004/0091891 A1 | 5/2004 | Iomantas et al. | |
| 2004/0146974 A1 | 7/2004 | Gunji et al. | |
| 2004/0166570 A1 | 8/2004 | Asahara et al. | |

OTHER PUBLICATIONS

Tsujimoto et al. J Biotechnol. Jul. 13, 2006;124(2):327-37. Epub Feb. 17, 2006.*
Chan et al. Biochem J. Nov. 15, 1991;280 ( Pt 1):139-46.*
Tsujimoto et al. J Biotechnol. Jul. 13, 2006;124(2):327-37. Epub Feb. 17, 2006. Abstract.*
Bellmann, A., et al., "Expression control and specificity of the basic amino acid exporter LysE of *Corynebacterium glutamicum*," Microbiology 2001;147:1765-1774.
International Search Report for PCT Patent App. No. PCT/JP2007/057524 (Jul. 17, 2007).
International Preliminary Report on Patentability for PCT Patent App. No. PCT/JP2007/057524 (Oct. 30, 2008).
Baev, M. V., et al., "Regulation of ammonia assimilation in an obligate methylotroph *Methylobacillus flagellatum* under steady-state and transient growth conditions," Antonie van Leeuwenhoek, International Journal of General and Molecular Microbiology 1997;71:353-361.
Grothe, E., et al., "Fermentation optimization for the production of poly(β-hydroxybutyric acid) microbial thermoplastic," Enzyme and Microbiol. Technol. 1999;25:132-141.
Gunji, Y., et al., "Enhancement of L-lysine production in methylotroph *Methylophilus methylotrophus* by introducing a mutant LysE exporter," J. Biotechnol. 2006;127(1):1-13.
Weuster-Botz, D., et al., "Substrate Controlled Fed-Batch Production of L-Lysine with *Corynebacterium glutamicum*," Biotechnol. Prog. 1997;13:387-393.
Supplementary European Search Report for European Patent App. No. 07740960.5 (Nov. 21, 2011).

* cited by examiner

*Primary Examiner* — Christian Fronda
(74) *Attorney, Agent, or Firm* — Shelly Guest Cermak Cermak Nakajima LLP

(57) ABSTRACT

A method for producing a carboxylic acid by a fermentation process which comprises culturing a methanol-assimilating bacterium capable of producing the carboxylic acid in a liquid medium containing methanol and a counter ion to produce and accumulate the carboxylic acid in the medium, further comprising the feeding of a substance comprising methanol and a counter ion to the medium by fed-batch culturing to maintain the total ionic strength within the fermentation medium at or below a certain level.

5 Claims, 6 Drawing Sheets

METHOD FOR PRODUCING CARBOXYLIC ACID USING METHANOL-ASSIMILATING BACTERIUM

This application is a continuation under 35 U.S.C. §120 to PCT Patent Application No. PCT/JP2007/057524, filed on Mar. 28, 2007, which claims priority under 35 U.S.C. §119 to Japanese Patent Application No. 2006-095207, filed Mar. 30, 2006, both of which are incorporated by reference. The Sequence Listing filed electronically herewith is also hereby incorporated by reference in its entirety (File Name: US-370_Seq_List; File Size: 74 KB; Date Created: Sep. 30, 2008).

BACKGROUND OF THE INVENTION

1. Field of the Invention

The present invention relates to the microbiology industries, and more particularly, to a method of producing carboxylic acid by fermentation. The present invention also relates to the microorganism which is used in the production method 2. Brief Description of the Related Art L-amino acids such as L-lysine, L-glutamic acid, L-threonine, L-leucine, L-isoleucine, L-valine, and L-phenylalanine are industrially produced by fermentation using microorganisms belonging to the genus *Brevibacterium, Corynebacterium, Bacillus, Escherichia, Streptomyces, Pseudomonas, Arthrobacter, Serratia, Penicillium, Candida*, and the like. To enhance productivity, strains of microorganisms are employed which have been isolated from nature and artificial variants thereof. Moreover, various technologies have been disclosed which increase the production of L-amino acids, such as recombinant DNA technology.

Methanol is an economical and commercially available raw material used in the conventional fermentation methods of carboxylic acid. Microorganisms employed in such methods include those belonging to the genera *Achromobacter, Pseudomonas* (Japanese Patent Application Publication No. Showa 45-25273), *Protaminobacter* (Japanese Patent Publication No. Showa 49-125590), *Protaminobacter, Methanomonas* (Japanese Patent Application Publication No. Showa 50-25790), *Microcyclus* (Japanese Patent Application Publication No. Showa 52-18886), *Methylobacillus* (Japanese Patent Application Publication No. Heisei 4-91793), and *Bacillus* (Japanese Patent Application Publication No. Heisei 3-505284).

Thus far, the use of artificial mutations or recombinant DNA techniques have been developed and used in a method of producing L-amino acids using *Methylophilus* bacteria. Specifically, the enzymatic activities of dihydrodipicolinate synthase and/or aspartokinase were increased (International Publication No. 00/61723). The amino acid export process has been a major obstacle in the production of amino acids by fermentation from methanol using methanol-assimilating bacteria. To overcome this problem, a mutant of the LysE protein, which participates in the export of L-lysine, exhibits L-lysine export activity in methanol-assimilating bacteria, and was isolated from bacteria of the genus *Corynebacterium*. Therefore, by breeding using artificial mutations, recombinant DNA techniques, and this modified L-lysine export carrier, it is possible to efficiently produce L-lysine. Hence, a method for producing L-amino acid using bacteria of the genus *Methylophilus* was developed (International Publication No. 00/61723 and Japanese Patent Publication No. 2004-166594).

Through the breeding of microorganisms such as discussed above, the ability to produce substances using methanol-assimilating bacteria has been greatly improved. However, there is still a need for the development of inexpensive and efficient methods of producing carboxylic acids from methanol.

SUMMARY OF THE INVENTION

The present invention provides a method for producing carboxylic acids, particularly L-amino acids, with high efficiency from methanol, which is inexpensive and abundantly available.

It was noticed that during fermentation using methanol-assimilating bacteria and methanol as the carbon source, a high ionic strength inhibited the proliferation of the bacteria. By feeding the culture while keeping the rate of increase in ionic strength in the culture medium at or below a certain level, a high production rate could be achieved without inhibiting the growth of the bacteria.

It is an aspect of the present invention to provide a method for producing carboxylic acid by fermentation comprising culturing a methanol-assimilating bacterium that has an ability to produce carboxylic acid in a liquid fermentation medium containing methanol and a counter ion, and collecting the carboxylic acid from the medium or the bacterium, wherein the total ionic strength is controlled to be a predetermined level or less in the fermentation medium by feeding a composition comprising methanol and a counter ion to the medium.

It is a further aspect of the present invention to provide the method as described above, wherein the rate of increase of the total ionic strength in the medium is 0.02 mol/m$^3$/hour or less.

It is a further aspect of the present invention to provide the method as described above, wherein the ionic strength is controlled during the proliferation period of the methanol-assimilating bacterium.

It is a further aspect of the present invention to provide the method as described above, wherein said substance is selected from the group consisting of ammonium sulfate, ammonium chloride, ammonium glutamate, ammonium succinate, ammonium fumarate, ammonium aspartate, urea, and combinations thereof.

It is a further aspect of the present invention to provide the method as described above, wherein said carboxylic acid is an L-amino acid.

It is a further aspect of the present invention to provide the method as described above, wherein said L-amino acid is L-lysine.

It is a further aspect of the present invention to provide the method as described above, wherein said methanol-assimilating bacterium is belongs to a genera selected from the group consisting of the genus *Acromobacter, Pseudomonas, Protaminobacter, Methanomonas, Microcyclus, Methylobacillus, Bacillus,* and *Methylophilus*.

It is a further aspect of the present invention to provide the method as described above, wherein said methanol-assimilating bacterium has been modified to increase the activity of an enzyme selected from the group consisting of diaminopimelate dehydrogenase, diaminopimelate decarboxylase, aspartate semialdehyde dehydrogenase, and combinations thereof.

It is a further aspect of the present invention to provide the method as described above, wherein DNA encoding dihydrodipicolinate synthase and/or aspartokinase that has been modified so it is not subject to feedback inhibition by L-lysine is present in said methanol-assimilating bacterium.

It is a further aspect of the present invention to provide the method as described above, wherein DNA encoding mutant lysE protein which promotes the export of L-lysine to the outside of the bacterium is present in said methanol-assimilating bacterium.

It is a further aspect of the present invention to provide a method for producing carboxylic acid by fermentation comprising culturing a methanol-assimilating bacterium that has an ability to produce the carboxylic acid in a liquid medium containing methanol and a counter ion, anc collecting the carboxylic acid from the medium or the bacterium, wherein a composition comprising methanol and a counter ion is fed to the medium by fed-batch culturing.

It is a further aspect of the present invention to provide the method as described above, wherein said counter ion is a monovalent ion.

It is a further aspect of the present invention to provide the method as described above, wherein said counter ion is selected from the group consisting of ammonium chloride, ammonium glutamate, ammonium succinate, ammonium fumarate, ammonium aspartate, and combinations thereof.

It is a further aspect of the present invention to provide the method as described above, wherein said carboxylic acid is an L-amino acid.

It is a further aspect of the present invention to provide the method as described above, wherein said L-amino acid is L-lysine.

It is a further aspect of the present invention to provide the method as described above), wherein said methanol-assimilating bacterium is of a genera selected from the group consisting of *Acromobacter, Pseudomonas, Protaminobacter, Methanomonas, Microcyclus, Methylobacillus, Bacillus*, and *Methylophilus*.

It is a further aspect of the present invention to provide the method as described above, wherein said methanol-assimilating bacterium has been modified to increase the activity of an enzyme selected from the group consisting of diaminopimelate dehydrogenase, diaminopimelate decarboxylase, aspartate semialdehyde dehydrogenase, and combinations thereof.

It is a further aspect of the present invention to provide the method as described above, wherein DNA encoding dihydrodipicolinate synthase and/or aspartokinase that has been modified so it is not subject to feedback inhibition by L-lysine is present in the bacterium.

It is a further aspect of the present invention to provide the method as described above, DNA encoding a variant lysE protein promoting the export of L-lysine to the outside of the cell when introduced into a methanol-assimilating bacterium.

DESCRIPTION OF THE PREFERRED EMBODIMENTS

<1> Production Method

Figure 1:
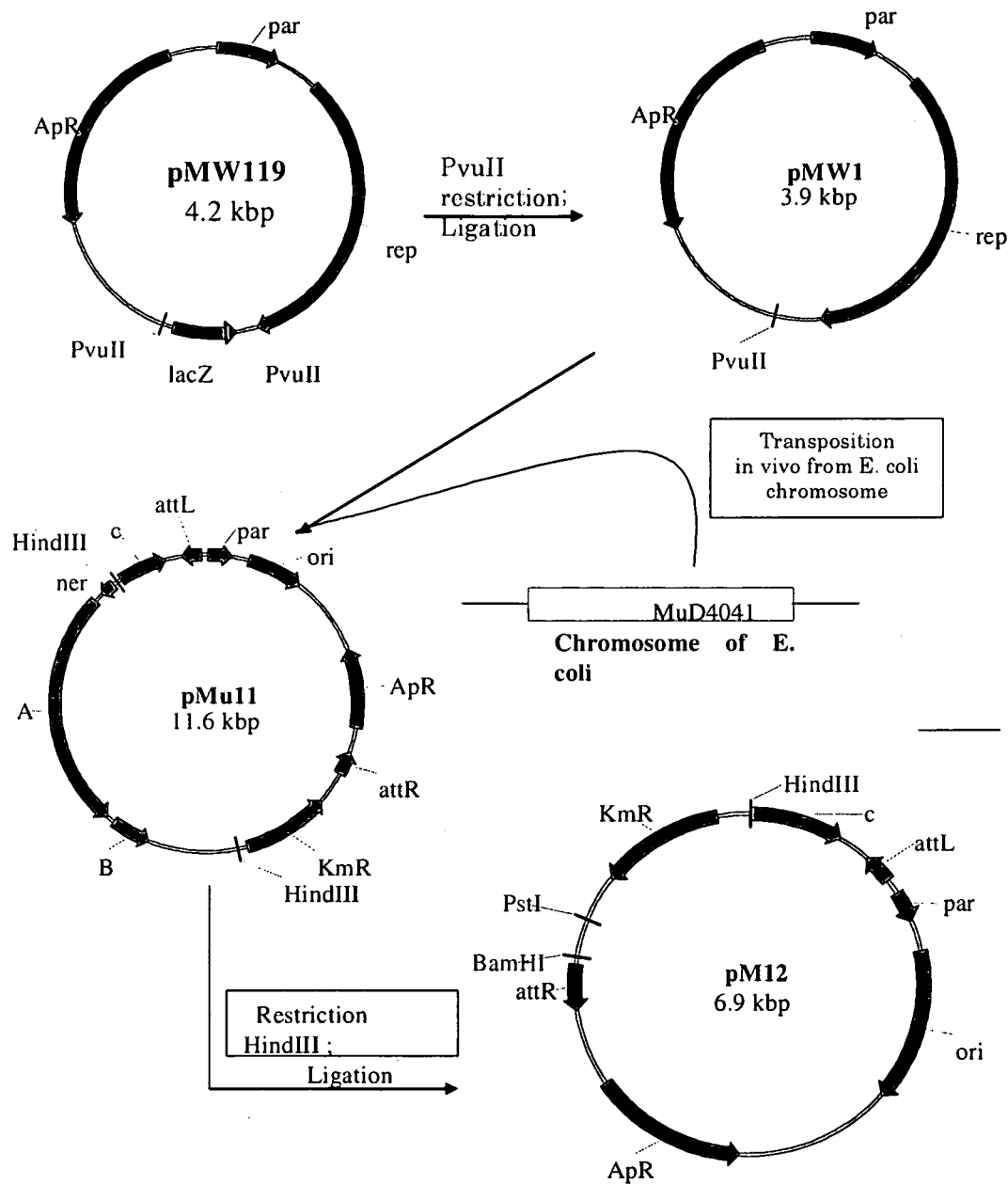
FIG. 1 shows the construction of the plasmid pM12.

A method of producing a carboxylic acid by culturing a methanol-assimilating bacterium having the ability to produce a carboxylic acid in a liquid medium containing methanol and a counter ion is described. More specifically, during the culture, methanol and the counter ion are added to the medium by a fed-batch method to control the total ionic strength at a predetermined level. The term "total ionic strength" means the strength of all ions which are present in the medium. The phrase "all ions contained in the medium" means all the cations and anions in the medium which contain carboxylic acid, carboxylic acid counter ions, other organic acids, and the like.

The term "carboxylic acid" means a substance having a carbon structure in the form of a carboxyl group ($-CO_2H$), including, for example, organic acids, fatty acids, amino acids, hydroxy acids, and keto acids. The carboxylic acid may be an L-amino acid, with no particular limitation on the type of L-amino acid. Examples include basic amino acids such as L-lysine, L-ornithine, L-arginine, L-histidine, and L-citrulline; aliphatic amino acids such as L-isoleucine, L-alanine, L-valine, L-leucine, and L-glycine; amino acids in the form of hydroxymonoaminocarboxylic acids, such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; and acidic amino acids such as L-glutamic acid, L-aspartic acid, L-glutamine, and L-asparagine. Of these, the basic L-amine acids L-lysine, L-asparagine, L-ornithine, and L-histidine are desirable.

The medium contains methanol as the carbon source, and is adjusted to contain counter ions of carboxylic acid.

The composition or substance serving as the source of the counter ions may be capable of maintaining a low total ionic strength in the medium. A composition containing monovalent or divalent anions is desirable. Examples are ammonium sulfate, ammonium chloride, ammonium glutamate, ammonium succinate, ammonium fumarate, ammonium aspartate, and urea.

The composition containing methanol and a counter ion is desirably fed to the culture medium in a feed medium. However, the composition containing methanol and counter ions may also be present in the initial medium. The term "initial medium" indicates the medium which is used in the batch culture prior to feeding any other medium, or the medium that is fed to the culture. The term "feed medium" indicates the medium that is fed into a fermentation vessel over the course of the fed-batch culture. The term "fermentation medium" indicates the medium used in the fermentation vessel, and the carboxylic acid is collected from this fermentation medium. "Fermentation vessel" means the apparatus in which the carboxylic acid fermentation is conducted, and a fermentation tank or jar fermentor may be employed. The capacity of the vessel need only be sufficient for the production and collection of the carboxylic acid.

The ionic strength of the counter ions in the fermentation medium may be controlled over the course of the culture, with the rate of increase in ionic strength of the total counter ions in the medium maintained at or below a predetermined level. The feeding of the composition containing the counter ions may be conducted while controlling the rate of rise in ionic strength to 0.02 mol/m$^2$/hour or less, desirably 0.015 mol/m$^2$/hour or less, and preferably, 0.01 mol/m$^2$/hour or less.

The ionic strength may be limited to or less than a predetermined level over the entire course of the culture, but may be so limited only during certain steps. For example, when there are periods of proliferation of the microorganism (proliferation period) and periods of production of the carboxylic acid (production period), the ionic concentration may be limited to or less than a predetermined concentration during the proliferation period. The ionic strength need not be kept within the above-stated range at all times during the culture; it is possible that the amount of counter ions which are present at a certain period may exceed the above-stated range, and then be reduced during culturing. The composition containing counter ions can also be intermittently added when the amount of counter ions decreases in fermentation. The term "proliferation period" indicates the period at the start of the culture when the carbon source is primarily used for bacterial growth. This period maybe about 10 hours, desirably 18 hours, and preferably 24 hours, and is the period during which the microorganism undergoes logarithmic growth. The "production period" indicates the period beginning 24 hours after the start of the culture during which production of carboxylic acid occurs.

It is sufficient that the feed medium contain a minimum number of counter ions of carboxylic acid; however, sulfer may still temporarily run short. The term "temporarily," for example, indicates the counter ions may run short for a period of about 20 percent, 40 percent, or a maximum of 60 percent of the total duration of fermentation. During the period when the counter ions run short, and may temporarily be 0, the rate of the increase in ionic strength may be 0.001 mol/m$^2$/hour or higher.

The rate of the increase in ionic strength in the fermentation medium can be calculated by measuring the quantity of sulfate ions, chloride ions, carbonate ions, and carboxylic acid. For example, the sulfate and chloride ions can be measured by ion chromatography, and the carbonate ions can be measured with a carbonic acid gas measuring apparatus.

Other carbon sources may be present in the medium in addition to methanol, such as glucose, glycerol, fructose, sucrose, maltose, mannose, galactose, starch hydrolysis products, molasses, and other sugars. Additionally, acetic acid, citric acid, and other organic acids may be present. Other raw materials which may be present and serve as the carbon source include cane molasses, beet molasses, high test molasses, and citrus molasses, as well as the hydrolysis products of natural raw materials such as cellulose, starch, corn, cereals, and tapioca. Carbon dioxide dissolved in the culture liquid can also function as the carbon source. These carbon sources can be present in the initial medium as well as in the feed medium. They may be mixed with methanol in both the initial medium and feed medium, or the culture may be conducted using only methanol as the carbon source in the feed medium, and some other carbon source initially.

Methanol is desirably fed to the fermentation medium so that the proportion in the fermentation medium is 2 percent or less, desirably 0.5 percent or less, and preferably, 0.2 percent or less.

The source of nitrogen in the medium may include counter ions, ammonium sulfate, ammonium chloride, ammonium glutamate, other ammonium salts, nitrates, and the like. Ammonia gas and ammonia water which are used to adjust the pH are also sources of nitrogen. Peptones, yeast extracts, meat extracts, wheat germ extracts, corn steep liquor, soybean hydrolysis products, and the like may also be present. These nitrogen sources may be present in both the initial medium and feed medium. These nitrogen sources may be blended into both the initial medium and the feed medium, or the nitrogen source present in the feed medium may be different from that present in the initial medium.

In addition to a carbon source, nitrogen source, and sulfur source, a phosphorus source is also desirably present in the medium. Phosphorus sources that are suitable for use include potassium dihydrogen phosphate, dipotassium hydrogen phosphate, pyrolinic acid, and other phosphoric acid polymers.

In addition to a carbon source, nitrogen source, and sulfur source, the medium may also contain a growth-promoting factor, such as trace metals, amino acids, vitamins, fatty acids, nucleic acids, peptones containing the same, casamino acids, yeast extracts, and soy protein degradation products. Examples of trace metals include iron, manganese, magnesium, and calcium. Examples of vitamins include vitamin B1, vitamin B2, vitamin B6, nicotinic acid, nicotinamide, and vitamin B12. These growth-promoting factors may be incorporated into the initial medium, or may be incorporated into the feed medium.

Furthermore, when an auxotrophic mutant requires nutrients such as amino acids or the like for growth, the required nutrients may be added to the medium. The addition of L-methionine and L-threonine when using L-lysine producing bacteria is desirable because L-lysine producing bacteria often auxotrophic for L-methionine or L-threonine and/or contain a deletion which results in degradation of L-threonine (U.S. Patent Application Publication 2004-0214296).

The culture may be conducted at a fermentation temperature of 20 to 45° C., preferably 33 to 42° C., with aeration. Here, the oxygen concentration is adjusted to between 5 and 50 percent, desirably about 10 percent. The pH is controlled to 5 to 9 and the culture is conducted with aeration. When the pH is reduced during the culture, for example, calcium carbonate or an alkali such as ammonia gas or aqueous ammonia may be added to neutralize the culture. Culturing under such conditions, desirably for about 10 to 120 hours, results in the accumulation of a large amount of carboxylic acid in the culture solution. The concentration of the carboxylic acid is higher than in wild-type strains; the concentration of L-lysine is not limited as long as L-lysine can be isolated and collected from the medium. The concentration is 10 g/L or greater, desirably 30 g/L or greater, and preferably, 50 g/L or greater.

The carboxylic acid can be collected from the culture medium at the end of the culture by any known collection method. For example, after removing the bacterial mass from the culture solution by centrifugal separation or the like, concentration precipitation can be used for collection. L-lysine can be collected by combining ordinary ion-exchange resin methods, precipitation methods, and other known methods.

The culture method may include batch culture, fed-batch culture, and continuous culture. To maintain the carboxylic acid accumulation at or above a prescribed level in the present invention, the seed culture and main culture can be conducted separately. The seed culture can be conducted as a shaking culture in a flask or the like, or as a batch culture. The main culture can be conducted as fed-batch culture or continuous culture. Both the seed culture and main culturing can be conducted as batch culture.

During the course of a fed-batch culture or continuous culture, the feeding of methanol and nutrient sources may be temporarily suspended. During the period of maximum feeding, feeding is stopped for 30 percent of the time or less, desirably 20 percent of the time or less, and preferably, 10 percent of the time or less. When the feed medium is intermittently added, the feed medium may be initially added over a predetermined level, and the second and following additions may occur when an increase in the pH or the dissolved oxygen concentration is detected by a computer (U.S. Pat. No. 5,912, 113).

A method of producing a carboxylic acid is described by fermentation of a methanol-assimilating bacterium having the ability to produce a carboxylic acid in a liquid medium containing methanol and counter ions. By this method, carboxylic acid is produced in the same medium, and the counter ion is a monovalent ion, such as ammonium chloride, ammonium glutamate, ammonium succinate, ammonium fumarate, and ammonium aspartate.

<2> The Methanol-Assimilating Bacteria

The term "methanol-assimilating bacterium" indicates a bacterium that is capable of growing using methanol as its main carbon source. Specific examples include bacteria of the genus *Methylophilus*, such as *Methylophilus methylotrophus*, bacteria of the genus *Methylobacillus*, such as *Methylobacillus glycogenes* and *Methylobacillus flagellatus*, bacteria of the genera *Acromobacter* and *Pseudomonas* (JP45-25273A), bacteria of the genus *Protaminobacter* (JP49-125590A), bacteria of the genera *Protaminobacter* and *Methanomonas* (JP50-25790A), and bacteria of the genus *Microcyclus* (JP52-18886A). Bacteria of the genus *Methylobacterium* may also be employed.

Examples of *Methylophilus methylotrophus* include the AS1 (NCIMB10515) and W3A1 (NCIMB 11348) strains. *Methylophilus methylotrophus* AS1 (NCIMB10515) and W3A1 (NCIMB 11348) are available from the National Collections of Industrial and Marine Bacteria, NCIMB Lts., Torry Research Station 135, Abbey Road, Aberdeen AB9 8DG, United Kingdom.

Examples of *Methylobacillus glycogenes* include the T-11 (NCIMP 11375), ATCC 21276, ATCC 21371, ATR80 (Appl. Microbiol. Biotechnol., (1994), Vol. 42, pp. 67-72), and A513 (Appl. Microbiol. Biotechnol., (1994), Vol. 42, pp. 67-72) strains. The *Methylobacillus glycogenes* NCIMB 11375 strain is available from the National Collections of Industrial and Marine Bacteria, NCIMB Lts., Torry Research Station 135, Abbey Road, Aberdeen AB9 8DG, United Kingdom.

Examples of *Methylobacillus flagellatus* include the ATTC 51484, KT (N. I. Govorukhina et al., Microbiology (Russia) 56 (1987), pp. 849-854), and VKM B-1610 strains. *Methylobacillus flagellatus* VKM B-1610 is available from the All-Russian Collection of Microorganisms (Russia, 142290, Moscow Region, Pushchino, pr. Nauki, 5, IBPM).

The *Methylobacillus glycogenes* ATCC 21276 and ATCC 21371, and the *Methylobacillus flagellatus* ATTC 51484 strains may be obtained from the American Type Culture Collection (ATCC) (ATCC, Address: P.O. Box 1549, Manassas, Va. 20108, 1, USA).

The term "capable of producing a carboxylic acid" means the ability to produce and secrete free carboxylic acid into the medium, that is, outside the cell, when cultured in the medium, and particularly means the ability to produce more carboxylic acid than the wild-type strain (parent strain). Examples of the wild-type strain include the AS1 strain (NCIMB 10515) for bacteria of the genus *Methylophilus* and the T-11 strain (NCIMB 11375) for bacteria of the genus *Methylobacillus*.

To obtain the ability to produce a carboxylic acid, a conventional method for breeding *Escherichia* bacteria may be used, such as by acquiring an auxotrophic mutant, analog resistant, strain, or metabolic control mutant strain, as well as by constructing a recombinant strain with enhanced activity of a carboxylic acid biosynthesis enzyme. (see Amino Acid Fermentation, Gakkai Shuppan Center, 1st ed. May 30, 1986, pp. 77-100). Therefore, when breeding carboxylic acid-producing bacteria, one or more properties such as an auxotrophic mutant, analog resistant, or metabolically controlled mutation may be imparted. The expression of one or more carboxylic acid biosynthesis-related enzymes may be increased. The acquisition of an auxotrophic mutant, analog resistance, or metabolically controlled mutation may be combined with the strengthening of a carboxylic acid biosynthesis-related enzyme.

Strains with an auxotrophic mutant, carboxylic acid analog-resistant strains, and variants with controlled metabolisms that are capable of producing carboxylic acid can be obtained by subjecting a parent strain or wild-type strain to a known mutagenic treatment, such as by irradiation with X-rays or ultraviolet radiation, or by treatment with a mutagenic agent such as N-methyl-N'-nitro-N-nitrosoguanidine (NTG) or ethyl methane sulfonate (EMS), and selecting those strains that exhibit both a auxotrophic mutant, analog resistance, or metabolically controlled mutation and the ability to produce a carboxylic acid from among the variants.

Examples of gene recombination include increasing the expression of the gene encoding an enzyme involved in the biosynthesis of the target carboxylic acid and reducing the activity of the gene encoding an enzyme involved in degradation of the targeted carboxylic acid.

Specific examples of microorganisms which are able to produce a carboxylic acid, and particularly microorganisms which are also able to produce L-amino acids, are described below. However, the microorganisms that can be employed are not limited to these.

<2-1> Imparting the Ability to Produce L-Lysine

Methanol-assimilating bacteria which are able to produce L-lysine, such as strains of *Methylophilus methylotrophus*, can be obtained by subjecting a strain which is not able to produce, or produces very little, L-lysine to a mutagenic treatment to impart resistance to a lysine analog such as S-(2-aminoethyl)-L-cysteine ("AEC" hereinafter). Methods of mutagenic treatment include subjecting the bacterial strain to a physical stimulus such as UV radiation, X-ray, or γ-rays, or treating it with a chemical mutagenic agent such as NTG. *Methylophilus methylotrophus* AJ13608 is an example of a bacterial strain of the genus *Methylophilus* which is able to produce L-lysine that was obtained in this manner.

The original bacterial strain was bred by imparting AEC-resistance to the *Methylophilus methylotrophus* AS1 strain. *Methylophilus methylotrophus* AJ13608 was deposited as deposit number FERM P-17416 with the National Institute of Bioscience and Human-Technology, Agency of Industrial Science and Technology (now the International Patent Organism Depositary (Chuo No. 6, 1-banchi, 1-chome, Tsukuba-shi Higashi, Ibaraki-ken, Japan, Postal Code 305-8566) of the National Institute of Advanced Industrial Science and Technology, an Independent Administrative Institution) on Jun. 10, 1999, and was converted to international deposit under the Budapest Treaty on Mar. 31, 2000, with the designation FERM BP-7112.

Methanol-assimilating bacteria which are able to produce L-lysine can also be bred using a gene recombination technique to introduce and increase DNA encoding genes involved in the biosynthesis of L-lysine. These genes include those encoding enzymes of the L-lysine biosynthesis pathway, such as dihydrodipicolinate synthase, diaminopimelate decarboxylase, and aspartate semialdehyde dehydrogenase.

For the genes of enzymes that are subject to feedback inhibition by L-lysine, such as dihydropicolinate acid synthase and aspartokinase, it is desirable to reduce or eliminate feedback inhibition by L-Lysine.

Furthermore, the ability to produce L-amino acid can also be enhanced by increasing the activity of proteins involved in the secretion of L-amino acids to the outside of the bacterium. For example, the LysE protein encoded by the lysE gene is known to contribute to the secretion of L-lysine to the outside of the cell (Vrljic, M., Sahm, H. and Eggeling, L. (1996) Mol. Microbiol. 22, 815-826, International Publication No. 97/23597). The wild-type of the lysE gene derived from bacteria of the genus *Brevibacterium* does not function at all in bacteria of the genera *Methylophilus* and *Methylobacillus*, but by mutating lysE, this protein is able to function in methylotrophes. The mutant lysE24 protein described below is an example of such a mutant lysE protein. The methanol-assimilating bacterium AJ110196, which has the lysE24 gene as well as the gene encoding dihydrodipicolinate synthase modified so it is not subject to feedback inhibition by L-lysine, was deposited (FERM BP-10434) under the Budapest Treaty at the International Patent Organism Depositary (Chuo No. 6, 1-banchi, 1-chome, Tsukuba-shi Higashi, Ibaraki-ken, Japan, Postal Code 305-8566) of the National Institute of Advanced Industrial Science and Technology, an Independent Administrative Institution, on Oct. 12, 2005.

The genes that can be employed in microorganisms will be specifically described below.

The dapA* Gene

The DNA encoding dihydrodipicolinate synthase which is desensitized to feedback inhibition by L-lysine (hereinafter, "the dapA* gene") is not particularly limited, however, it is preferably, for example, the DNA encoding a dihydrodipicolinate synthase derived from, or native to, a bacterium belonging to the genus *Escherichia*, and having a mutation to desensitize feedback inhibition by L-lysine.

An example of the DNA encoding wild-type dihydrodipicolinate synthase derived from, or native to, a bacterium belonging to the genus *Escherichia* is that which encodes the amino acid sequence of SEQ ID NO: 41. An example of the mutation which results in desensitization of the feedback inhibition by L-lysine is the histidine residue at position 118 in the amino acid sequence of SEQ ID NO: 41 is replaced with a tyrosine residue (H118Y mutation). Therefore, an example of the dapA* gene is the DNA encoding the amino acid sequence of SEQ ID NO: 41 in which the histidine residue at position 118 is replaced with a tyrosine residue.

The dapA* gene may also be a DNA encoding a protein which is at least 80%, preferably at least 90%, more preferably at least 95%, particularly preferably at least 98% homologous to the entire amino acid sequence of SEQ ID NO: 41, and which also has the H118Y mutation and dihydrodipicolinate synthase activity.

Moreover, the dapA* gene may encode a protein having the amino acid sequence of SEQ ID NO: 41, but which includes substitution, deletion, insertion, addition, or the like of one or several amino acids, so long as the protein has the H118Y mutation and the dihydrodipicolinate synthase activity is not impaired.

Although the number of amino acids which constitutes "several" may differ depending on their relative positions in the three-dimensional structure of the protein, or the types of amino acid residues being altered, it is specifically 1 to 20, preferably 1 to 10, and more preferably 1 to 5. The above-mentioned substitution of amino acids is preferably a conservative substitution. Examples of conservative substitutions include: substitution of ser or thr for ala; substitution of gln, his, or lys for arg; substitution of glu, gln, lys, his, or asp for asn; substitution of asn, glu, or gln for asp; substitution of ser or ala for cys; substitution of asn, glu, lys, his, asp, or arg for gln; substitution of gly, asn, gln, lys, or asp for glu; substitution of pro for gly; substitution of asn, lys, gln, arg, or tyr for his; substitution of leu, met, val, or phe for ile; substitution of ile, met, val, or phe for leu; substitution of asn, glu, gln, his, or arg for lys; substitution of ile, leu, val or phe for met; substitution of trp, tyr, met, ile, or leu for phe; substitution of thr or ala for ser; substitution of ser or ala for thr; substitution of phe or tyr for trp; substitution of his, phe, or trp for tyr; and substitution of met, ile, or leu for val. The amino acid substitutions, deletions, insertions, additions, inversions, or the like may be the result of a naturally-occurring mutation (mutant or variant) due to an individual difference, or a difference in the bacterial species harboring the dihydrodipicolinate synthase gene.

The dapA* gene may be able to hybridize with a complementary strand of the nucleotide sequence of SEQ ID NO: 40, or a probe that can be prepared from the sequence, under stringent conditions so long as the gene encodes a protein having the H118Y mutation and dihydrodipicolinate synthase activity. The term "stringent conditions" refers to conditions where a so-called specific hybrid is formed and a non-specific hybrid is not formed. It is difficult to clearly define the conditions with a numerical value, but examples include conditions corresponding to a salt concentration and temperature of washing which are typical for a standard Southern hybridization, e.g., washing at 60° C. with 1×SSC and 0.1% SDS, preferably at 60° C. with 0.1×SSC and 0.1% SDS, and more preferably at 68° C. with 0.1×SSC and 0.1% SDS, once or preferably twice or three times.

The dapA* gene may be obtained by site-specific mutagenesis, or from the RSFD80 plasmid as described below.

It is known that the wild-type dihydrodipicolinate synthase derived from coryneform bacteria is not subject to feedback inhibition by L-lysine (J Gen Microbiol. 1988 December; 134 (12): 3221-9.). Therefore, it is not always necessary to use a DNA encoding a dihydrodipicolinate synthase which is desensitized to feedback inhibition by L-lysine.

DNA encoding mutant LysE that promotes export or secretion of L-lysine to the outside of the bacterium when the DNA is introduced into methanol-assimilating bacterium Examples of DNA encoding a mutant LysE protein that promotes export of L-lysine to the outside of a bacterium when the DNA is introduced into a methanol-assimilating bacterium include the LysE24 gene (US 2003-0124687), lysE56 gene (US 2004-0146974), and lysE24m5 (WO 2006/059715).

The expression "promoting export or secretion of L-lysine to the outside of a bacterium" means that when a methanol-assimilating bacterium containing the DNA is cultured in a medium, the amount of L-lysine exported into the medium increases as compared with the methanol-assimilating bacterium not containing the DNA. An increase in the export of the L-lysine to the outside of the cell occurs when there is an increase in L-lysine accumulation in the medium during the culture of the methanol-assimilating bacterium containing the DNA as compared with the accumulation when methanol-assimilating bacterium not containing the DNA is cultured.

The DNA encoding mutant LysE that promotes export of L-lysine to the outside of a bacterium when the DNA is introduced into the methanol-assimilating bacterium is preferably, but is not limited to, a DNA encoding the LysE protein derived from a bacterium belonging to the genus *Brevibacterium* and having a mutation which promotes the export of L-lysine to the outside of a bacterium when the DNA is introduced into the methanol-assimilating bacterium, and examples thereof include the LysE24 gene (US 2003-0124687), lysE56 gene (US 2004-0146974), and lysE24m5 (WO 2006/059715).

(1) lysE24 Gene

The wild-type lysE gene encodes a protein (wild-type lysE protein: SEQ ID NO: 55) having a loop region and six hydrophobic helixes that is involved in the export of L-lysine to the outside of a bacterium. The mutant lysE24 gene encodes a mutant lysE protein that does not have the loop region and promotes export of L-lysine, L-arginine, or both when the DNA is introduced into the methanol-assimilating bacterium.

Examples of the LysE24 gene include the LysE24 gene described in JP 2004-166594 A (US 2005-003495).

An example includes the DNA encoding the protein of SEQ ID NO: 51. In addition, the protein may be not less than 80%, preferably not less than 90%, more preferably not less than 95%, particularly preferably not less than 98% homologous to the entire amino acid sequence of SEQ ID NO: 51, so long as the gene can promote export of L-lysine to the outside of a bacterium when it is introduced into a methanol-assimilating bacterium.

Moreover, the gene may be the DNA encoding the protein having the sequence of SEQ ID NO: 51, but which includes substitutions, deletions, insertions, additions, or the like of one or several amino acids so long as the activity for promoting export of L-lysine to the outside of a cell is not impaired.

Moreover, the lysE24 gene may be a DNA which is able to hybridize with a complementary strand of the nucleotide sequence of SEQ ID NO: 50, or a probe that can be prepared from the nucleotide sequence, under stringent conditions so long as the gene encodes a protein having the activity for promoting export of L-lysine to the outside of a cell.

The definitions of the terms "several" and "stringent conditions" and preferable amino acid substitutions are the same as described above.

The lysE24 gene can be obtained from, for example, the plasmid pRSlysE24 described in JP 2004-166594 A (US 2005-003495). The *E. coli* JM109 strain transformed with pRSlysE24 was designated as AJ13830, and deposited at the National Institute of Advanced Industrial Science and Technology, International Patent Organism Depositary on Jun. 4, 2001 and given an accession number of FERM P-18369. Then, the deposit was converted to an international deposit under the provisions of the Budapest Treaty on May 13, 2002, and given the accession number FERM BP-8040.

(2) lysE56 Gene

An example of the lysE56 gene is the gene encoding the protein having the amino acid sequence of SEQ ID NO: 55 in which at least the glycine residue at position 56 is replaced with another amino acid residue (US 2004-0146974). The gene may also encode a protein having the amino acid sequence of SEQ ID NO: 55 but which is not less than 80%, preferably not less than 90%, more preferably not less than 95%, particularly preferably not less than 98% homologous to SEQ ID NO: 55, and in which the glycine residue at position 56 is replaced with another amino acid residue, so long as the gene can promote export of L-lysine to the outside of a methanol-assimilating bacterium.

(3) lysE24m5 Gene

This gene includes a DNA having the nucleotide sequence of the lysE24 gene, but which has been modified so that each reading frame includes a stop codon, and promotes export of L-lysine, L-arginine, or both to the outside of a methanol-assimilating bacterium when the DNA is introduced into the bacterium. Specific examples include the DNA having the nucleotide sequence of SEQ ID NO: 56 (WO 2006/059715). The gene may be a DNA which is able to hybridize with a complementary strand of the nucleotide sequence of SEQ ID NO: 56, or a probe that can be prepared from the nucleotide sequence, under stringent conditions so long as the gene encodes a protein having the activity for promoting export of L-lysine to the outside of a cell.

The ddh Gene

The diaminopimelate dehydrogenase activity can be enhanced using a gene encoding diaminopimelate dehydrogenase (hereinafter, "the ddh gene").

An example of the ddh gene includes, but is not limited to, a DNA encoding diaminopimelate dehydrogenase derived from, or native to, a coryneform bacterium (SEQ ID NO: 53).

The ddh gene may be a DNA encoding a protein which is not less than 80%, preferably not less than 90%, more preferably not less than 95%, particularly preferably not less than 98% homologous to the entire amino acid sequence of SEQ ID NO: 53, and which has diaminopimelate dehydrogenase activity.

The ddh gene may also be a DNA encoding the protein having the sequence of SEQ ID NO: 53, but which includes one or several amino acid substitutions, deletions, insertions, additions, or the like, so long as diaminopimelate dehydrogenase activity is not impaired.

Moreover, the ddh gene may be a DNA which is able to hybridize with a complementary strand of the nucleotide sequence of SEQ ID NO: 52, or a probe that can be prepared from the nucleotide sequence, under stringent conditions so long as the gene encodes a protein having diaminopimelate dehydrogenase activity.

The definitions of the terms "several" and "stringent conditions" and preferable amino acid substitution are the same as described above.

The ddh gene from coryneform bacterium can be obtained by amplification through PCR using two oligonucleotide primers (for example, SEQ ID NOS: 11 and 12 described in WO/9516042, U.S. Pat. No. 6,040,160), which are prepared based on the known nucleotide sequence of ddh from *Corynebacterium glutamicum* (Ishino, S. et al., Nucleic Acid Res., 15, 3917 (1987)) and using the chromosomal DNA of *Brevibacterium lactofermentum* or *Corynebacterium glutamicum* as the template.

The lysA Gene

The diaminopimelate decarboxylase activity can be enhanced using the diaminopimelate decarboxylase gene (hereinafter, "the lysA gene"). An example of the lysA gene includes, but is not limited to, the DNA encoding diaminopimelate decarboxylase derived from, or native to, a bacterium belonging to the genus *Methylophilus* (SEQ ID NO: 49).

The lysA gene may be a DNA encoding a protein which is not less than 80%, preferably not less than 90%, more preferably not less than 95%, particularly preferably not less than 98% homologous to the entire amino acid sequence of SEQ ID NO: 49 and having diaminopimelate decarboxylase activity.

The lysA gene may also be a DNA encoding a protein having the sequence of SEQ ID NO: 49, but which includes one or several amino acid substitutions, deletions, insertions, additions, or the like so long as diaminopimelate decarboxylase activity is not impaired.

Moreover, the lysA gene may be a DNA which is able to hybridize with a complementary strand of the nucleotide sequence of SEQ ID NO: 48, or a probe that can be prepared from the nucleotide sequence, under stringent conditions so long as the gene encodes a protein having diaminopimelate decarboxylase activity.

The definitions of the terms "several" and "stringent conditions" and preferable amino acid substitutions are the same as described above.

The lysA gene of *Methylophilus methylotrophus* can be obtained by PCR using two oligonucleotide primers prepared based on the known sequence and using the chromosomal DNA of *Methylophilus methylotrophus* as the template.

The dapB Gene

The dihydrodipicolinate reductase activity can be enhanced using a gene encoding dihydrodipicolinate reductase (hereinafter, "the dapB gene"). An example of the dapB gene includes, but is not limited to, a DNA encoding dihydrodipicolinate reductase derived from, or native to, a bacterium belonging to the genus *Escherichia* (SEQ ID NO: 43).

The dapB gene may be a DNA encoding a protein which is not less than 80%, preferably not less than 90%, more preferably not less than 95%, particularly preferably not less than 98% homologous to the entire amino acid sequence of SEQ ID NO: 43 and having dihydrodipicolinate reductase activity.

The dapB gene may also be a DNA encoding the protein having a sequence of SEQ ID NO: 43, but which includes one or several amino acid substitutions, deletions, insertions, additions, so long as the dihydrodipicolinate reductase activity is not impaired.

Moreover, the dapB gene may be a DNA which is able to hybridize with a complementary strand of the nucleotide sequence of SEQ ID NO: 42, or a probe that can be prepared from the nucleotide sequence, under stringent conditions so long as the gene encodes a protein having the dihydrodipicolinate reductase activity.

The definitions of the terms "several" and "stringent conditions" and preferable amino acid substitutions are the same as described above.

The dihydrodipicolinate reductase gene (dapB) can be amplified by PCR using two oligonucleotide primers prepared based on the known nucleotide sequence and using the chromosomal DNA of *E. coli* as the template.

The asd Gene

The aspartate-semialdehyde dehydrogenase activity can be enhanced using the gene encoding aspartate-semialdehyde dehydrogenase (hereinafter, "the asd gene"). An example of the asd gene includes, but is not limited to, a DNA encoding aspartate-semialdehyde dehydrogenase derived from, or native to, a bacterium belonging to the genus *Escherichia* (SEQ ID NO: 45).

The asd gene may be a DNA encoding a protein which is not less than 80%, preferably not less than 90%, more preferably not less than 95%, particularly preferably not less than 98% homologous to the entire amino acid sequence of SEQ ID NO: 45 and having aspartate-semialdehyde dehydrogenase activity.

The asd gene may also be a DNA encoding a protein having the sequence of SEQ ID NO: 45, but which includes one or several amino acid substitutions, deletions, insertions, additions, or the like so long as the aspartate-semialdehyde dehydrogenase activity is not impaired.

Moreover, the asd gene may be a DNA which is able to hybridize with a complementary strand of the nucleotide sequence of SEQ ID NO: 44, or a probe that can be prepared from the nucleotide sequence, under stringent conditions so long as the gene encodes a protein having aspartate-semialdehyde dehydrogenase activity.

The definitions of the terms "several" and "stringent conditions" and preferable amino acid substitutions are the same as described above.

The aspartate-semialdehyde dehydrogenase gene (asd) can be amplified by PCR using two oligonucleotide primers prepared based on the known nucleotide sequence and using the chromosomal DNA of *E. coli* as the template.

The lysC* Gene

The methanol-assimilating bacterium may further include a DNA encoding aspartokinase that is desensitized to feedback inhibition by L-lysine.

Examples of the DNA encoding aspartokinase that is desensitized to feedback inhibition by L-lysine (hereinafter, "the lysC* gene") preferably include, but are not limited to, the DNA encoding aspartokinase derived from, or native to, a bacterium belonging to the genus *Escherichia* and having a mutation to desensitize to feedback inhibition by L-lysine.

An example of the DNA encoding the wild-type aspartokinase derived from a bacterium belonging to the genus *Escherichia* is the DNA encoding the amino acid sequence of SEQ ID NO: 47. An example of the mutation to desensitize feedback inhibition by L-lysine is the threonine residue at position 352 is replaced with an isoleucine residue in the amino acid sequence of SEQ ID NO: 47 (T352I mutation). Therefore, an example of the lysC* gene is the DNA encoding the amino acid sequence of SEQ ID NO: 47 in which the threonine residue at position 352 is replaced with an isoleucine residue.

The lysC* gene may be a DNA encoding a protein which is not less than 80%, preferably not less than 90%, more preferably not less than 95%, particularly preferably not less than 98% homologous to the entire amino acid sequence of SEQ ID NO: 47, includes the T352I mutation, and has aspartokinase activity.

The lysC*gene may also be a DNA encoding the protein having the sequence of SEQ ID NO: 47, but which includes one or more amino acid substitutions, deletions, insertions, additions, or the like so long as it includes the T352I mutation and the aspartokinase activity is not impaired.

Moreover, the lysC* gene may be a DNA which is able to hybridize with a complementary strand of the nucleotide sequence of SEQ ID NO: 46, or a probe that can be prepared from the nucleotide sequence, under stringent conditions so long as the gene has the T352I mutation and encodes a protein having aspartokinase activity.

The definitions of the terms "several" and "stringent conditions" and preferable amino acid substitutions are the same as described above.

The lysC* gene may be obtained by site-specific mutagenesis, or from the RSFD80 plasmid as described below.

The DNA encoding aspartokinase which is desensitized to feedback inhibition by L-lysine does not necessarily have to be DNA encoding variant aspartokinase. That is, the wild-type form can be employed so long as it is not subject to L-lysine feedback inhibition.

In the present invention, the phrase "increasing the activity of enzyme" means that the enzymatic activity in the cell is increased relative to the activity in the wild-type strain (for example, the *M. methylotrophus* AS1 strain) or the parent strain (for example, a cell with no modifications to increase the specific combination of enzymes as described herein), and also means that the bacterium exhibits an enzymatic activity that is not present in the wild-type or parent strain. The methods of measuring the activity of the above-described enzymes are known, and increasing the activity in the cell can be readily confirmed by those of ordinary skill in the art.

Examples of the procedure which can be used to enhance or increase the intracellular activity include, but are not limited to, the following procedures and combinations thereof:

(1) Transformation with a plasmid carrying the DNA encoding each protein.

(2) Incorporation into the chromosome of the DNA encoding the each protein.

(3) Modifying the promoter sequences of the genes encoding the proteins.

The methanol-assimilating bacterium should have the ability to produce L-lysine as a result of the modifications mentioned above, for example, increasing the expression of one or more of the following genes: lysE24, dapA*, lysA, ddh, dapB, asd, (lysC*). The phrase "the ability to produce L-lysine" indicates the ability to produce a recoverable quantity of L-lysine in the medium when the methanol-assimilating bacterium is cultivated in medium.

The methanol-assimilating bacterium may have mutations which makes it auxotrophic, analog-resistant, and/or metabolically controlled, or the like, and then the modifications such as those described above may be made. Examples include bacteria that have been modified as set forth above, such as variants requiring L-homoserine, L-threonine, and/or L-methionine (JP48-28078A and 56-6499A); mutants which are auxotrophic for inositol or acetic acid (JP55-9784A and 56-8692A); and mutants which are resistant to oxalidine, lysine hydroxamate, S-(2-aminoethyl)cysteine, γ-methyl lysine, α-chlorocaprolactam, DL-α-amino-ε-caprolactam, α-aminolauryllactam, aspartic acid-analog, sulfa agents, quinoids, or N-lauroyl leucine.

Alternatively, mutations resulting in auxotrophic mutants, analog resistance, metabolism controls, and the like can be introduced after imparting the above-described modification (gene amplification).

Examples of methods for increasing expression of the aspartokinase gene (lysC* gene) and dihydrodipicolinate synthase gene (dapA* gene) that is not subject to feedback inhibition by L-lysine and will be shown below.

To increase the expression of the dapA* gene and the lysC* gene, DNA fragments of the genes are ligated to a vector that is able to replicate in bacteria of the genus *Methylophilus*, desirably a multicopy vector, to prepare recombinant DNA. This is then transformed into the *Methylophilus* bacterium host. Since the number of copies of these genes is increased, the activity of dihydrodipicolinate synthase and aspartokinase in the cell is increased. Dihydrodipicolinate synthase is abbreviated to "DDPS," aspartokinase to "AK," and aspartokinase III to "AKIII."

Any microorganism of the genus *Methylophilus* having DNA capable of expressing DDPS activity and AK activity can be used. The microorganism may be a wild-type strain or a mutant strain derived from a wild-type strain. *E. coli* (*Escherichia coli*) K-12 strain and *Methylophilus methylotrophus* ASI strain (NCIMB 10515) may be used as the host strain. The DNA sequence of the gene encoding DDPS derived from genus *Escherichia* (Richaud, F, et al. J. Bacteriol., 297 (1986)) and the gene encoding AKIII (Cassan, M., Pasrot, C., Cohen, G. N. and Patte, J. C., J. Biol. Chem., 261, 1052 (1986)) have both been determined. Thus, these genes can be obtained by primers synthesized based on the sequences of the genes and using PCR with chromosomal DNA of *E. coli* K-12 or the like as the template. Examples of dapA and lysC derived from *E. coli* are shown below, but the genes are not limited to these.

The DDPS and AK should not be subject to feedback inhibition by L-lysine. Wild-type DDPS derived from *E. coli* is known to be subject to feedback inhibition by L-lysine. Wild-type AKIII derived from *E. coli* is also known to be inhibited by L-lysine and to be subject to feedback inhibition by L-lysine. Accordingly, mutations that remove this feedback inhibition are desirably introduced prior to introduction into bacteria of the genus *Methylophilus*.

However, for example, since DDPS derived from bacteria of the genus *Corynebacterium* is not subject to feedback inhibition by L-lysine, the DDPS gene and the AK gene are not necessarily the above-noted mutant genes.

It is possible to obtain dapA* encoding DDPS and lysC* encoding AK which are not subject to feedback inhibition by performing PCR with two oligonucleotide primers prepared using known sequences employing plasmid containing these genes as the template.

The broad-host-range plasmid RSFD80 is known to contain dapA* and lysC* (WO95/16042). An *E. coli* JM109 strain that has been transformed with this plasmid is named "AJ12396." This strain was deposited (FERM P-13936) with the National Institute of Bioscience and Human-Technology, Agency of Industrial Science and Technology, MITI (now the International Patent Organism Depositary of the National Institute of Advanced Industrial Science and Technology, an Independent Administrative Institution) on Oct. 28, 1993, and converted to international deposit under the Budapest Treaty on Nov. 1, 1994, and given the designation FERM BP-4859. RSFD80 can be obtained by known methods from the AJ12396 strain.

The sequence of the dapA* on the RSFD80 has a T instead of a C at base position 597 (see the wild-type dapA gene at SEQ ID NO: 40). Thus, this mutation results in the encoded protein sequence having a tyrosine residue instead of a histidine residue at position 118 in the amino acid sequence of SEQ ID NO: 41. The sequence of the lysC* on the RSFD80 has a T instead of a C at base position 1638 (see the wild-type lysC of SEQ ID NO: 46). Thus, this mutation results in the encoded protein sequence having an isoleucine residue instead of the threonine residue at position 352 in the amino acid sequence of SEQ ID NO: 47.

The plasmid used to clone the gene can be able to replicate in a microorganism such as *Escherichia*; examples are pBR322, pTWV228, pMW119, and pUC19.

The vector which is able to function in a bacterium of the genus *Methylophilus* is, for example, a plasmid that is autonomously replicable in a bacterium of the genus *Methylophilus*. Examples include the broad-host-range vector RSF1010 and its derivatives, such as pAYC32 (Chistorerdov, A. Y., Tsygankov, Y. D. Plasmid, 1986, 16, 161-167), pMFY42 (Gene, 44, 53 (1990)), pRP301, and pTB70 (Nature, 287, 396 (1980)). pBBR1, another broad-host-range vector that is incompatible with RSF1010, and its derivatives, such as pBHR1, (Antoine, R. and Locht, C., Molecular Microbiology, 6, 1785-99 (1992)) are further examples.

When the DNA encoding dapA*, lysC*, and other proteins is ligated to the vector which is able to function in the *Methylophilus* bacterium, the vector is cut with restriction enzymes corresponding to the terminals of the DNA fragments containing these genes. The ligation is normally conducted with a ligase such as T4 DNA ligase. These genes can be located on separate vectors, or located on a single vector.

Methods well known to those of ordinary skill in the art can be employed to cut and ligate the DNA, prepare chromosomal DNA, conduct PCR, prepare plasmid DNA, conduct transformation, identify oligonucleotides for use as primers, and the like. These methods are described in Sambrook, J., Fritsch, E. F., and Maniatis, T., "Molecular Cloning, A Laboratory Manual, Second Edition," Cold Spring Harbor Laboratory Press (1989) and the like.

Any method that allows for adequate transformation efficiency can be employed to introduce the recombinant DNA thus prepared into the *Methylophilus* bacterium. One example is electroporation (Canadian Journal of Microbiology, 43. 197 (1997)).

DDPS and AK activity can be increased by introducing multiple copies of dapA* and lysC* into the chromosomal DNA of the *Methylophilus* bacterium. Introduction of multiple copies of the DNA can be accomplished by using a sequence that is present in multiple copies on the chromosomal DNA as a target, and conducting homologous recombination. Repetitive DNA and the inverted repeats present on the ends of transposons are typically present in multiple copies on the chromosomal DNA. Alternatively, as is disclosed in JP2-109985A, dapA* and/or lysC* can be carried on a transposon, and transposed resulting in the introduction of multiple copies into the chromosomal DNA. Regardless of the chosen, the increase in the number of copies of dapA* and lysC* in the transformant amplifies the DDPS and AK activity.

In addition to amplifying the genes as described above, DDPS and AK activity can also be increased by substituting the native promoters of dapA* and lysC* with a stronger promoter (see Japanese Patent Application Publication No. Heisei 1-215280). Examples of known strong promoters are the lac promoter, trp promoter, trc promoter, tac promoter, lambda phage PR promoter, PL promoter, tet promoter, amyE promoter, and spac promoter. Replacing the native promoter with one of these promoters increases the expression of dapA* and lysC*, thereby amplifying DDPS and AK activity. The enhancement of expression regulation sequences can be combined with increasing the number of copies of dapA* and lysC*.

Enhancing the expression of the dapA* gene and lysC* gene to increase the activity of DDPS and AK within the cell has been described. Increasing the expression of the lysE24 gene, dapB gene, lysA gene, ddh gene, and asd gene is also similarly possible.

In addition to enhancing the expression of the above-described six or seven genes, other enzymes involved in the biosynthesis of L-lysine can also be increased in the methanol-assimilating bacterium. Examples of such enzymes include phosphenol pyruvate carboxylase (JP 60-87788A), aspartate aminotransferase (JP6-102028A), enzymes in the diaminopimelic acid pathway, such as diaminopimelate epimerase (JP2003-135066A), and enzymes in the aminoadipic acid pathway, such as homoaconitate hydratase.

Examples of enzymes that catalyze reactions directed away from the L-lysine synthesis pathways to produce compounds other than L-lysine are homoserine dehydrogenase (see WO 95/23864) and L-lysine decarboxylase (Japanese Patent Application Publication No. 2004-254544). Modifications can be made in these enzymes so that enzymatic activity is reduced by inactivation of the gene by homologous recombination.

The methanol-assimilating bacterium can also be modified so that L-methionine is required for growth (JP2004-248669A) by subjecting the bacterium to natural mutation or a mutagenic treatment so that it cannot grow in a medium that does not contain L-methionine, or by disruption of the metA gene (JP2004-248669A) or metF gene (SEQ ID NO: 58).

Examples of bacteria producing L-amino acids other than L-lysine are described below. The ability to produce an L-amino acid can be imparted by obtaining a variant with an auxotrophic mutant, an analog-resistant mutant, or a metabolically controlled mutant; creating a strain which overexpresses an enzyme involved in the biosynthesis of the L-amino acid; or applying a method that has conventionally been used to breed bacteria of the genus *Escherichia*, coryneform bacteria, or the like (see Amino Acid Fermentation, Gakkai Shuppan Center, 1st ed. May 30, 1986, pp. 77-100).

Furthermore, L-amino acid-producing bacteria can also be constructed by increasing the expression of genes related to the biosynthesis of the L-amino acid and attenuating the genes that degrade the L-amino acid.

2-2 Imparting the Ability to Produce L-Glutamic Acid

The ability to produce L-glutamic acid can be imparted to a *Methylophilus* bacterium, for example, by introducing DNA encoding enzymes such as glutamate dehydrogenase (JP61-268185A), glutamine synthetase, glutamate synthase, isocitrate dehydrogenase (JP62-166890 and 63-214189), aconitate hydratase (JP62-294086A), citrate synthase (JP62-201585A and Showa 63-119688A), phosphenol pyruvate carboxylase (JP60-87788A and JP62-55089A), pyruvate dehydrogenase, pyruvate kinase, phosphenol pyruvate synthase, enolase, phosphoglyceromutase, phosphoglycerate kinase, glyceryl aldehyde-3-phosphate dehydrogenase, triosephosphate isomerase, fructose bisphosphate aldolase, phosphofructokinase (JP63-102692A), glucose phosphate isomerase, and glutamine oxoglutarate aminotransferase (WO 99/07853).

The activity of enzymes that catalyze reactions which result in degradation of L-glutamic acid, or which direct reactions away from the biosynthesis pathway of L-glutamic acid so that compounds other than L-glutamic acid are produced, can be decreased or deleted. Examples of these enzymes include α-ketoglutarate dehydrogenase (αKGDH), isocitrate lyase, phosphate acetyl transferase, acetate kinase, acetohydroxylate synthase, acetolactate synthase, formate acetyltransferase, lactate dehydrogenase, glutamate decarboxylase, and 1-pyrroline dehydrogenase.

2-3 Imparting the Ability to Produce L-Threonine

The ability to produce L-threonine can be imparted or increased by, for example, increasing the activities of aspartokinase, homoserine dehydrogenase, homoserine kinase, and threonine synthase. The activity of these enzymes can be increased, for example, by transforming a *Methylophilus* bacterium with a recombinant plasmid containing the threonine operon (see JP 55-131397A, JP59-31691A, JP56-15696A, and JP3-501682A).

Furthermore, the ability to produce L-threonine can be imparted and increased by amplifying or introducing the threonine operon which includes the gene encoding aspartokinase which is not subject to feedback inhibition by L-threonine (JP1-29559A), the gene encoding homoserine dehydrogenase (JP60-012995A), or the genes encoding homoserine kinase and homoserine dehydrogenase (JP61-195695).

The ability to produce L-threonine can also be enhanced by introducing DNA encoding a mutant phosphenol pyruvate carboxylase which is not subject to feedback inhibition by aspartic acid.

2-4 Imparting the Ability to Produce L-Valine

The ability to produce L-valine can be imparted by, for example, introducing genes related to the biosynthesis of L-valine from which the control mechanisms have essentially been removed. Mutations that essentially remove the control mechanisms from genes related to the biosynthesis of L-valine can also be introduced.

The ilvGMEDA operon of *E. coli*, for example, is related to the biosynthesis of L-valine. The threonine deaminase encoded by the ilvA gene catalyzes the deamination reaction from L-threonine to 2-ketobutyric acid, which is a rate-limiting step in the biosynthesis of L-isoleucine. Accordingly, for the L-valine synthesis reaction to progress efficiently, an operon that does not express threonine deaminase activity should be used. Therefore, the ilvA gene on the ilvGMEDA operon should be mutated or partially or entirely deleted so that threonine deaminase activity is not expressed.

Furthermore, expression of the ilvGMEDA operon is regulated and attenuated by L-valine, L-isoleucine, and/or L-leucine. Thus, the region required for attenuation should be deleted or mutation so that expression is not inhibited by the produced L-valine.

The ilvGMEDA operon that does not express threonine deaminase activity and that is not attenuated by the produced L-amino acid can be obtained by subjecting the wild-type ilvGMEDA operon to a mutagenic treatment or through changes caused by genetic recombination techniques (see WO 96/06926).

2-5 Imparting the Ability to Produce L-Leucine

The ability to produce L-leucine can be imparted or increased by, for example, introducing genes relating to the biosynthesis of L-leucine from which the control mechanisms have been essentially removed into the *Methylophilus* bacteria, in addition to the above-described properties required for the production of L-valine. It is also possible to introduce mutations that essentially remove the control mechanisms of the genes related to the biosynthesis of L-leucine. An example of such a gene is the leuA gene which has been mutated to remove the inhibition by L-leucine.

2-6 Imparting the Ability to Produce L-Isoleucine

The ability to produce L-isoleucine can be imparted by introducing the thrABC operon which includes the *E. coli* thrA gene encoding aspartokinase 1-homoserine dehydrogenase I which has been mutated to remove the inhibition by L-threonine, and the ilvGMEDA operon, which has been mutated to delete regions required for attenuation. The operon may also contain the ilvA gene encoding threonine deaminase which has been mutated to delete the inhibition by L-isoleucine (see JP8-47397A).

2-7 Imparting the Ability to Produce Other Amino Acids

The biosynthesis of L-tryptophan, L-phenylalanine, L-tyrosine, L-threonine, and L-isoleucine can be increased by enhancing the ability to produce phosphenol pyruvate in the *Methylophilus* bacteria (WO 97/08333).

The ability to produce L-phenylalanine and L-tyrosine can be enhanced by amplifying or introducing the desensitizable chorismate mutase-prephenate dehydratase (CM-PDT) gene (see JP62-130693A) or the desensitizable 3-deoxy-D-arabino-hepturonic acid-7-phosphate synthase (DS) gene (see JP5-236947A and JP61-124375A).

Furthermore, the ability to produce L-tryptophan can be enhanced by amplifying or introducing the tryptophan operon containing the gene encoding desensitizable anthranylate synthase (JP57-71397A and JP62-244382A, and U.S. Pat. No. 4,371,614).

The phrase "enzymatic activity is increased" indicates that the activity of the enzyme in the cell is higher than in the wild-type strain. When a bacterial strain with increased enzymatic activity is obtained through modification(s) made by genetic recombination techniques, then the activity of the enzyme in the cell is greater than before the modification(s). The phrase "enzymatic activity is decreased" indicates that the activity of the enzyme within the cell is lower than in the wild-type strain. When a bacterial strain with reduced enzymatic activity is obtained through modification(s) made by genetic recombination techniques, then the activity of the enzyme within the cell is lower than before the modification(s).

EXAMPLES

The present invention is described in detail below through the following non-limiting embodiments.

Reference Example 1

Unless specifically stated otherwise, the reagents used in these examples were obtained from Wako Pure Chemical Industries, Ltd. or Nacalai Tesque, Inc. The compositions of the media are as indicated below. The pH of the media was adjusted with NaOH or HCl.

| LB medium: | |
|---|---|
| Tryptone peptone (made by Difco) | 10 g/L |
| Yeast extract (made by Difco) | 5 g/L |
| NaCl | 10 g/L |
| pH 7.0 | |
| Steam sterilization was conducted for 20 minutes at 120° C. | |
| LB agar medium: | |
| Bacto agar | 15 g/L |
| Steam sterilization was conducted for 20 minutes at 120° C. | |
| SEII medium | |
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 µg/L |
| $MnSO_4 \cdot 5H_2O$ | 25 µg/L |
| $ZnSO_4 \cdot 7H_2O$ | 23 µg/L |
| $CaCl_2 \cdot 2H_2O$ | 72 mg/L |
| $FeCl_3 \cdot 6H_2O$ | 9.7 mg/L |
| Methanol | 0.5% (vol/vol) |
| pH 7.0 | |

All ingredients except for methanol were steam sterilized for 15 minutes at 121° C. The methanol was added after the components had suitably cooled.

| SEII production medium: | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 µg/L |
| $MnSO_4 \cdot 5H_2O$ | 25 µg/L |
| $ZnSO_4 \cdot 7H_2O$ | 23 µg/L |
| $CaCl_2 \cdot 2H_2O$ | 72 mg/L |
| $FeCl_3 \cdot 6H_2O$ | 9.7 mg/L |
| Sodium pyruvate | 2.5 g/L |
| $CaCO_3$ (made by Kanto Chemical Co., Inc.) | 30 g/L |
| Methanol | 2% (vol/vol) |
| pH 7.0 | |

All ingredients except for methanol were steam sterilized for 15 minutes at 121° C. The methanol was added after the component had suitably cooled.

| SEII agar medium | |
|---|---|
| $K_2HPO_4$ | 1.9 g/L |
| $NaH_2PO_4$ | 1.56 g/L |
| $MgSO_4 \cdot 7H_2O$ | 0.2 g/L |
| $(NH_4)_2SO_4$ | 5 g/L |
| $CuSO_4 \cdot 5H_2O$ | 5 µg/L |
| $MnSO_4 \cdot 5H_2O$ | 25 µg/L |
| $ZnSO_4 \cdot 7H_2O$ | 23 µg/L |
| $CaCl_2 \cdot 2H_2O$ | 72 mg/L |
| $FeCl_3 \cdot 6H_2O$ | 9.7 mg/L |
| Sodium pyruvate | 1.0 g/L |
| Methanol | 1% (vol/vol) |
| pH 7.0 | |
| Bacto agar (made by Difco) | 15 g/L |

All ingredients except for methanol were steam sterilized for 15 minutes at 121° C. The methanol and, as needed, L-methionine solution adjusted to 20 g/L and sterilized by filtration, were added after the components had suitably cooled.

Reference Example 1

Construction of a Mini-Mu System, pMIV-Km, pMIV-Km-EA, pAET7

To increase the number of copies of the lysE24 and variant dapA genes on the chromosome, the *E. coli* bacteriophage Mu-phage gene recombination system was employed.

Figure 2:
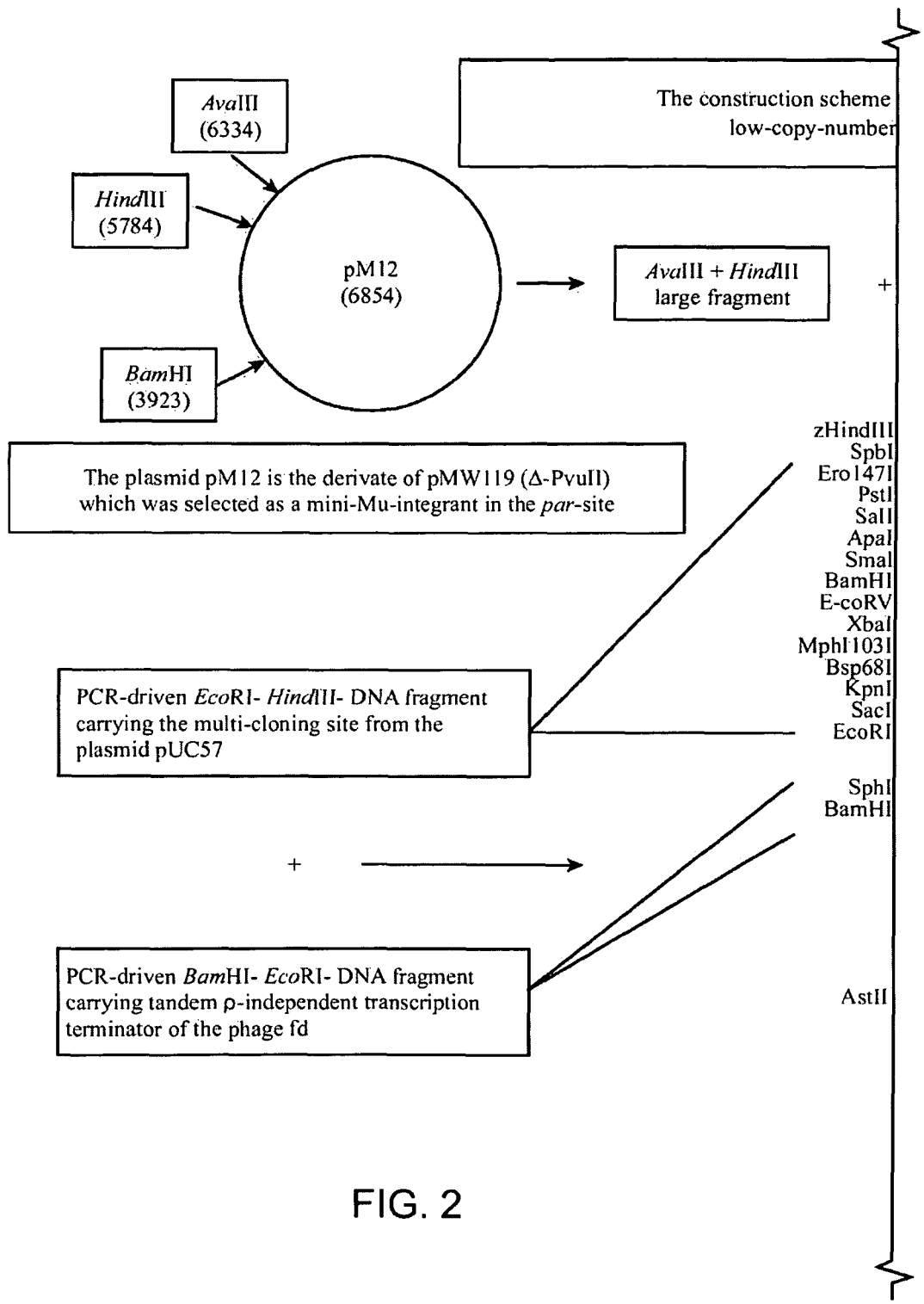
FIG. 2 shows the construction of the pMIV5.
Figure 2:
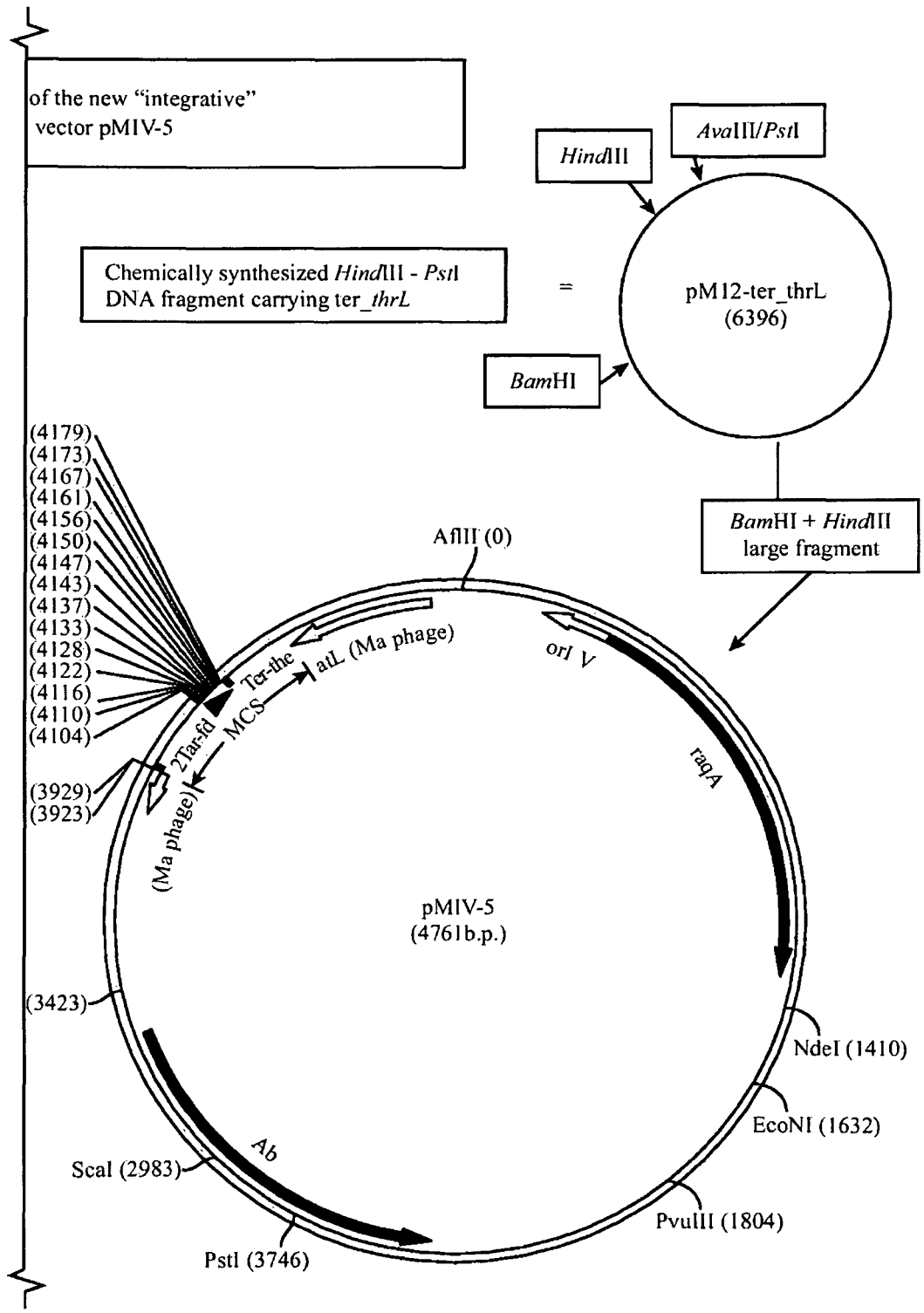

Construction of pMIV5 (FIGS. 1 and 2)

In order to incorporate Mu-phage into the chromosome of *Escherichia coli*, a drug resistance gene located between the recognition sequences attL and attR, and a transferase (Mu transposase) are required. Both of these genes do not need to be carried on the same vector. First, the pMIV5 plasmid was contracted, which contains the recognition sequences attL and attR, and a kanamycin resistance gene, while the pAET7 plasmid with the Mu transposase was constructed separately. Both of these plasmids can function when they are present in the same bacterium, resulting in the transfer of the region located between attL and attR to the chromosomal DNA.

The pMIV5 plasmid was constructed as follows. First, pMW119 (available from TOYOBO Co., Ltd.) is digested with the PvuII restriction enzyme and separated by agarose gel electrophoresis to collect a fragment of about 3.9 kbp. This fragment was ligated with the DNA Ligation Kit (Takara Bio Inc.), to obtain the pMW1 plasmid. Subsequently, mini-Mu-phage was transferred to the pMW1 plasmid in *E. coli* cells. Specifically, pMD4041 (Journal of Bacteriology 158, 488-495 (1984)) was introduced into the *Escherichia coli* K12 strain, and a strain resistant to kanamycin and sensitive to ampicillin was selected to obtain a strain in which the plasmid pMD4041 was eliminated and mini-Mu 4041 was transferred to the chromosome. A factor that represses Mu transfer of mini-Mu4041, for example, c repressor, has a temperature-sensitive mutation. Therefore, when the strain is cultured at 42° C., c repressor of mini-Mu on the chromosome is deactivated, and the transfer of mini-Mu4041 to the chromosome is significantly activated, resulting in cell death. The strain with lysogenized mini-Mu4041 on the chromosome was transformed with pMW1 at 30° C. This strain was cultured in LB medium until the number of cells reached $2 \times 10^8$ cells/ml, and then was treated at 42° C. for 1 hour. In order to obtain a plasmid with mini-Mu4041 transferred to the pMW1 plasmid, plasmid DNA was prepared from the cells and used to transform an *Escherichia coli* strain. Plasmids were prepared from 50 of the transformants displaying kanamycin and ampicillin resistance, and the structures of the plasmids were determined by treating with a restriction enzyme, to thereby select the plasmid of interest. This plasmid was designated as pMu11. In the plasmid pMu11, mini-Mu4041 was transferred to the par region in the pMW1. More specifically, in pMW119 which contains fragments of the known plasmids pBR322 and pSC101, mini-Mu4041 was inserted into position 259, where the boundary position between the plasmids was defined as position 0. The plasmid was digested with the HindIII restriction enzyme and separated by agarose gel electrophoresis to collect a fragment of about 6.9 kbp, and this fragment was ligated with the DNA Ligation Kit (Takara Bio Inc.), to construct the pM12 plasmid (FIG. 1). pM12 was digested with HindIII-AvaIII (EcoT22I) and used as a vector into which the terminator region of the PCR-amplified thr operon of *E. coli* was inserted. PCR amplification was performed using the chromosomal DNA of *E. coli* as the template and p-ter-thrL-f (SEQ ID NO: 1) and p-ter-thrL-r (SEQ ID NO: 2) as primers, under the following conditions for 25 cycles: denaturation at 94° C. for 20 seconds, annealing at 55° C. for 30 seconds, and extension at 72° C. for 60 seconds. The resulting plasmid was digested with the EcoRI-HindIII restriction enzyme, and the PCR-amplified multi-cloning site region and the PCR-amplified ρ-factor independent transcription termination factor fragment from a bacteriophage fd were inserted into the plasmid. The multi-cloning site region was amplified by PCR using the pUC57 plasmid (Fermentus AB, available from LITHUANIA) as the template and pUC57-MCS-f (SEQ ID NO: 3:) and pUC57-MCS-r (SEQ ID NO: 4) as primers, and PCR was performed under the following conditions for 25 cycles: denaturation at 94° C. for 20 seconds, annealing at 55° C. for 30 seconds, and extension at 72° C. for 30 seconds. The amplified fragment was digested with EcoRI-BamHI, the recognition sites of which had been added to the primer. The ρ-factor independent transcription termination factor fragment was amplified by PCR using the genomic DNA of the bacteriophage fd as the template and ter-fd-f (SEQ ID NO: 5) and ter-fd-r (SEQ ID NO: 6:) as primers, and PCR was performed under the following conditions for 25 cycles: denaturation at 94° C. for 20 seconds, annealing at 55° C. for 30 seconds, and extension at 72° C. for 30 seconds. The amplified fragment was digested with EcoRI-HindIII, recognition sites of which had been added to the primer. The three fragments were ligated with the DNA Ligation kit (Takada Bio Inc.) to construct the pMIV5 plasmid (FIG. 2). Then, the plasmid was digested with EcoRV, and a kanamycin resistance gene fragment obtained by cleaving a commercially-available plasmid (pUC4K) with HincII was inserted into the plasmid to construct the pMIV5-Km plasmid.

pMIV-Km-lysE24dapA

A gene of interest was inserted into the pMIV5-Km plasmid, and used to incorporate the gene with mini-Mu, and the plasmid was used to transfer the gene fragment of interest to the chromosome. Specifically, the plasmid pMIV5-Km was digested with SmaI, followed by a dephosphorylation treatment. The fragment lysE24+dapA* was obtained by amplification through PCR using a known plasmid containing the pRSlysEdapA gene (JP 2003-61687 A) as the template, and pRS-1s (SEQ ID NO: 8:) and dapA-r (SEQ ID NO: 7:) as primers. PCR was performed under the following conditions for 25 cycles: denaturation at 94° C. for 20 seconds, annealing at 55° C. for 30 seconds, and extension at 72° C. for 120 seconds. PCR-amplified fragments were ligated with the TaKaRa BKL kit (Takara Bio Inc.) to construct the pMIV-Km-lysE24dapA plasmid.

Figure 4:
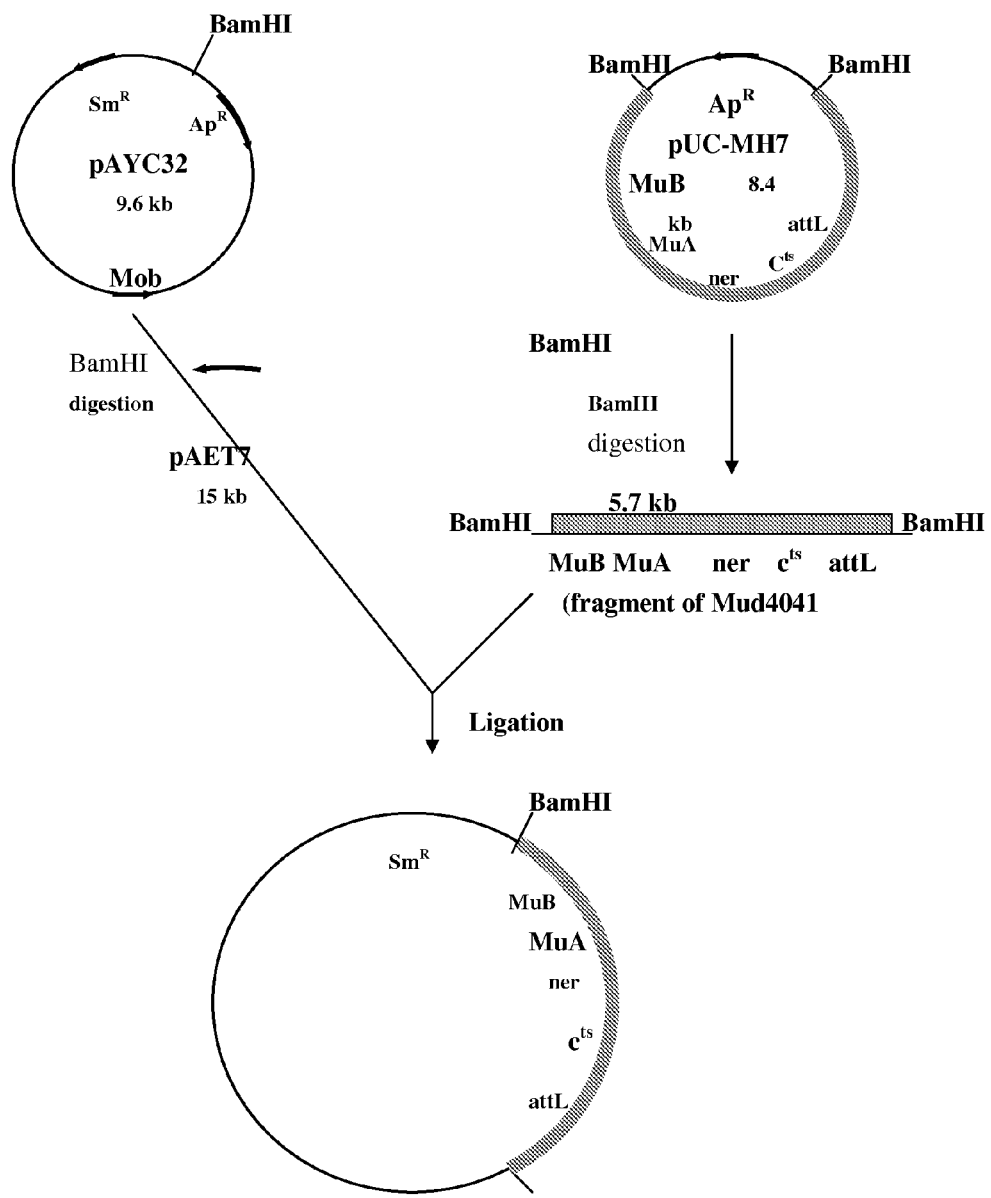
FIG. 4 shows the construction of the plasmid pAET7.
Figure 5:
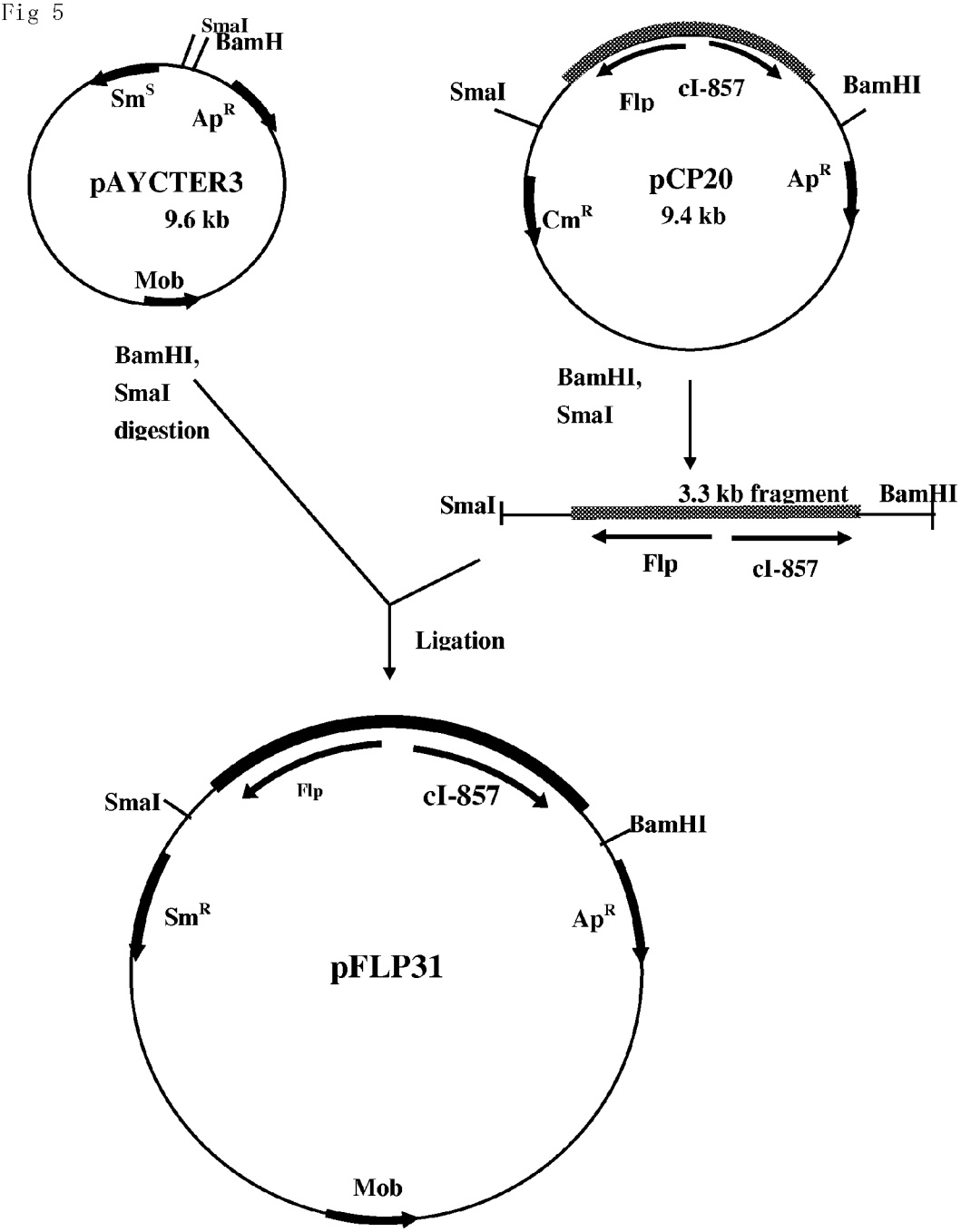
FIG. 5 shows the construction of the plasmid pFLP31.

Construction of pAET7 (FIG. 4)

pUC1918 (Gene, (1993) 134, 89-91) was digested with the EcoRI restriction enzyme, and the resulting fragment was blunt-ended. This fragment was used to insert a blunt-ended DNA fragment encoding Mu transposase, and a DNA fragment was obtained by digesting pMu4041 (Journal of Bacteriology, (1984), 158, 488-495) with ScaI-Eco47III. This plasmid was designated as pUC-MH7. pUC-MH7 was digested with BamHI, and the resulting DNA fragment encoding Mu transposase was inserted into the BamHI site of pAYC32 (Journal of General Microbiology 137, 169-178 (1991)) to obtain the pAET7 plasmid.

Reference Example 2

Incorporation of the lysE24 and Mutant dapA Genes into the Chromosome of *Methylophilus methylotrophus*, and the Acquisition of VAE#1

First, pAET7 was introduced into the *M. methylotrophus* AS strain by electroporation, and the bacterium was inoculated onto an SEII plate containing 50 mg/l streptomycin.

Then, the pMIV-Km-lysE24dapA plasmid was introduced into the resulting transformant to obtain strains that formed colonies on the SEII plate containing 20 mg/l kanamycin and 50 mg/l streptomycin. The mini-Mu cassette includes a kanamycin resistance gene, and the pMIV-Km-lysE24dapA plasmid, which cannot replicate in *M. methylotrophus*. Therefore, the kanamycin-resistant colonies have the mini-Mu cassette inserted into the chromosome. Accordingly, 200 strains were randomly selected and spread onto an SEII plate containing 50 mg/l streptomycin and 20 mg/L kanamycin, followed by culturing at 37° C. overnight. Then, bacterial cells present on the medium surface of about 0.3 square centimeters were scraped off and inoculated into an SEII production medium (5 ml) containing 50 mg/l streptomycin and 20 mg/L kanamycin, and the cells were cultured with shaking at 37° C. for 34 hours. After completion of the culture, the bacterial cells were removed by centrifugation, and the concentration of L-lysine in each culture supernatant was measured using a Biotech-analyzer AS-210 (manufactured by Sakura Seiki Co., Ltd.). The strain containing the highest concentration of L-lysine was selected and designated as VAE#1.

Reference Example 3

Acquisition of a Strain with High Copy Numbers of lysE24 and Mutant dapA Genes (VAE#8)

The VAE#1 strain was shown to have one or two copies of the mini-Mu cassette inserted into the chromosome. Therefore, in order to improve productivity of L-lysine, the mini-Mu cassette was amplified on the chromosome. The gene encoding the MuC protein, which is capable of suppressing Mu transposase activity, is present on the pAET7 plasmid carrying the Mu transposase. The MuC protein is temperature sensitive, and therefore, when the strain is cultured at 42° C., the Mu transposase is active, resulting in amplification of the mini-Mu cassette on the chromosome. Specifically, the VAE#1 strain was suspended in SEII liquid medium to an appropriate concentration, and the suspension was incubated at 42° C. for 1 hour and diluted to an appropriate concentration. The bacterial solutions were inoculated onto SEII plates containing 50 mg/L streptomycin and 20 mg/L kanamycin to form single colonies. From the single colonies, 200 colonies were selected randomly and spread on SEII plates containing 50 mg/L streptomycin and 20 mg/L kanamycin, followed by culturing at 37° C. overnight. Then, bacterial cells which were present on the medium surface of about 0.3 square centimeters were scraped off and inoculated into an SEII production medium (5 ml) containing 50 mg/L streptomycin and 20 mg/L kanamycin, and the cells were cultured with shaking at 37° C. for 34 hours. After completion of the culture, the bacterial cells were removed by centrifugation, and the concentration of L-lysine in each culture supernatant was measured using a Biotech-analyzer AS-210 (manufactured by Sakura Seiki Co., Ltd.). The strain with the highest concentration of L-lysine was designated as VAE#2. The procedure was repeated 8 times to obtain the VAE#8 strain. The amount of Lys produced by VAE#1 was defined as 100, and the relative value of the amount of Lys produced by the VAE#8 strain was calculated and is shown in Table 1.

TABLE 1

| Strain | Relative amount of produced Lys (%) |
| --- | --- |
| VAE#1 | 100 |
| VAE#8 | 800 |

Reference Example 4

Determination of Transfer Site in VAE#8

Next, the site containing the transferred mini-Mu cassette was transferred onto the chromosome of the VAE#8 strain was determined. The chromosomal DNA of the VAE#8 strain was prepared and completely digested with the SalI restriction enzyme. The resulting fragment was ligated to the pHSG398 vector, and selection was performed in an LB agar medium containing 12.5 mg/L chloramphenicol and 25 mg/L kanamycin to prepare plasmid DNA from the colonies. There is a kanamycin resistance gene on the mini-Mu cassette and chromosomal DNA around the transfer site in the plasmid. The nucleotide sequence of the plasmid was determined using a sequencing primer (SEQ ID NO: 9), which was designed outwardly in the inside of attR present on the right hand edge of the mini-Mu cassette, to thereby determine the transfer site of the mini-Mu cassette. It is also possible to construct a strain identical to VAE#8 based on the information of the transfer region determined by the above-described method.

Reference Example 5

Imparting Met-Auxotrophy to VAE#8 (#403)

Next, methionine auxotrophy was imparted to the VAE#8 strain. Imparting amino acid auxotrophy to an amino acid-producing bacterium is effective for controlling the number of bacterial cells during the culture. The VAE#8 strain was mutated by treatment with NTG by a known method (WO 00/61723, U.S. Pat. No. 7,223,572) and appropriately diluted to a cell density to form a single colony, and the bacterium was inoculated into an SEII agar medium containing 0.5 g/L L-methionine. The cells were replicated on an SEII agar medium containing no L-methionine to obtain a strain that could not grow on the plate, that is, a strain auxotrophic for L-methionine. The strain was designated as #403. A plurality of genes from the #403 strain, which is known to be involved in the biosynthesis of L-methionine, were cloned by a method well-known to a person skilled in the art based on the homology to another microorganism to determine the nucleotide sequences. As a result, it was found that part of the metF gene encoding 5,10-methylenetetrahydrofolate reductase was deleted. Specifically, it was found that the region between the 92nd nucleotide and the 344th nucleotide, as counted from the initiation codon of the metF gene, was deleted. Therefore, L-methionine auxotrophy was imparted by disrupting the metF gene of VAE#8 by a known method (JP 2004-229662 A, Homologous recombination method using linear DNA). Details are described in Example 19. The strain with an artificially disrupted metF was found to have the same properties as the strain auxotrophic for L-methionine obtained by the above-described NTG-mutation treatment, #403. A DNA fragment was prepared to disrupt the gene by overlap-PCR (Ho, S, N., Hunt, H. D., Horton, R. M., Pullen, J. K. and Pease, L. R., Gene, 77, 51-9. (1989)). When the #403 strain and the control strain VAE#8 were cultured in the SEII production medium containing 0.075 g/L L-methionine and 2.5 g/L sodium pyruvate, the amount of Lys increased. The amount of Lys produced by the VAE#8 strain was defined as 100, and the relative value of the amount of Lys produced by the #403 strain was calculated and is shown in Table 2.

TABLE 2

| Strain | Relative amount of produced Lys (%) |
|---|---|
| VAE8 | 100 |
| #403 | 156 |

Reference Example 6

Figure 3:
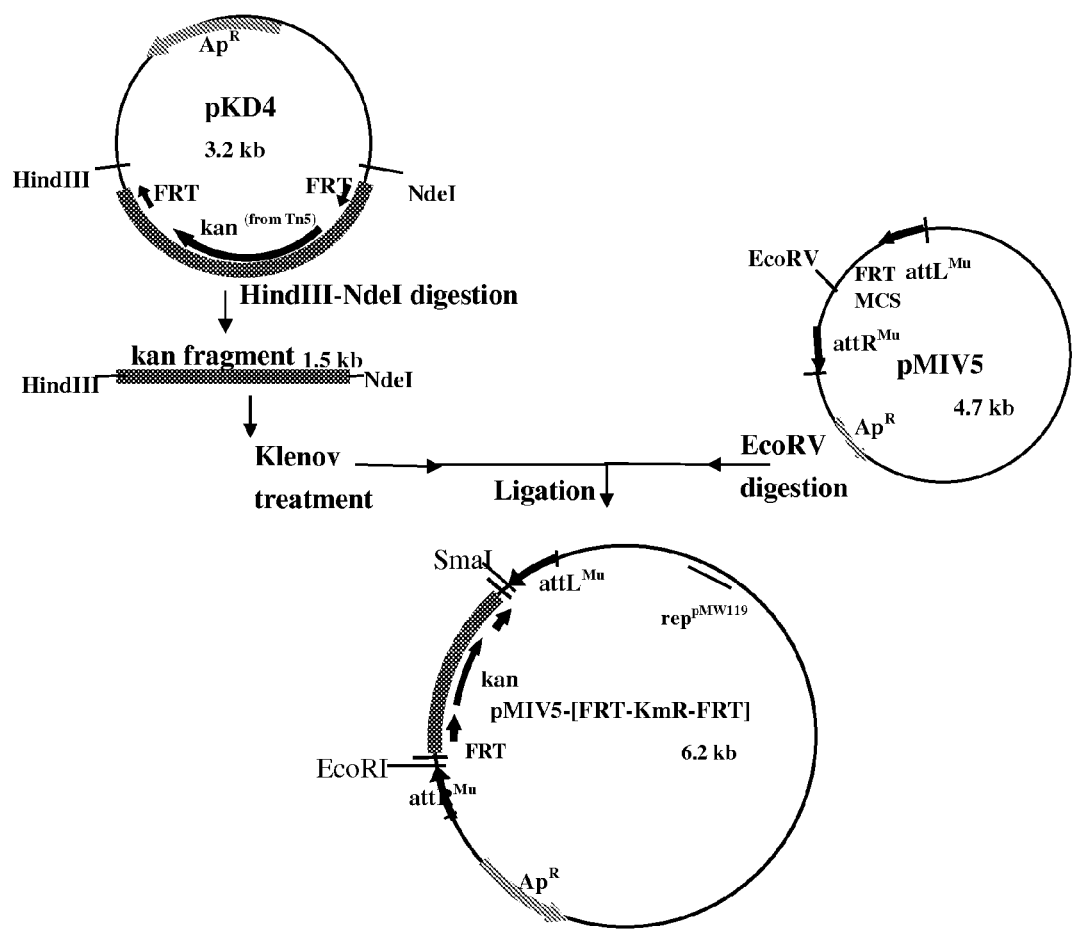
FIG. 3 shows the construction of the plasmid pMIV-FRT-mFRT.

Construction of the pMIV-FRTGmFRT and pMIV-FRTGmFRT-EAplasmids (FIG. 3)

In order to further incorporate a mini-Mu cassette into the #403 strain, an insertion cassette having a gene resistant to an antibiotic other than kanamycin was constructed. Specifically, the pMIV5 plasmid was digested with EcoRV and used as a vector. Then, pKD4 (Proceedings of the National Academy of Sciences of the United States of America, (2000) 97, 6640-6645) was digested with HindIII-NdeI, and the resulting fragment was blunt-ended, followed by insertion of the fragment having the kanamycin resistance gene region. This plasmid was designated as pMIV-FRTKmFRT. The plasmid was digested with the BglII restriction enzyme, and the resulting fragment was blunt-ended, followed by insertion of the PCR-amplified gentamicin resistance gene fragment. PCR was performed using pML122 (Gene, 89, 37-46. (1990)) as the template and pGm-f (SEQ ID NO: 10) and pGm-r (SEQ ID NO: 11) as primers, under the following conditions for 25 cycles: denaturation at 94° C. for 20 seconds, annealing at 55° C. for 30 seconds, and extension at 72° C. for 60 seconds. The plasmid was designated as pMIV-FRTGmFRT. A gene of interest was inserted into the region between attL and attR to construct a mini-Mu cassette to amplify the gene of interest on the chromosome of *M. methylotrophus* (FIG. 3). Specifically, the pMIV-FRTGmFRT plasmid was digested with the SmaI restriction enzyme, followed by dephosphorylation. The lysE24+dapA* fragment was obtained by amplification with PCR using a known plasmid having the pRSlysEdapA gene (JP 2003-61687 A, U.S. Pat. No. 7,169,587) as the template, and pRS-1s and dapA-r as primers. PCR was performed under the following conditions for 25 cycles: denaturation at 94° C. for 20 seconds, annealing at 55° C. for 30 seconds, and extension at 72° C. for 120 seconds. PCR-amplified fragments were phosphorylated using a TaKaRa BKL kit (Takara Bio Inc.) and ligated to a vector, to thereby construct the pMIV-FRTGmFRT-EA plasmid. The pKD4 and pCP20 plasmids were registered at the *E. coli* Genetic Stock Center as CGSC strains #7632 and #7629, respectively, and are available from the Center.

Reference Example 7

Acquisition of a Strain with Higher Copy Numbers of the lysE24 and Mutant dapA Genes Using pMIV-Gm-EA (#403-11-Gm)

First, pAET7 was introduced into the #403 strain, and the cells were inoculated onto an SEII plate containing 50 mg/l streptomycin. Then, the pMIV-FRTGmFRT-EA plasmid was introduced into the resulting pAET7 transformant by electroporation to obtain strains that formed colonies on an SEII plate containing 50 mg/l streptomycin. The mini-Mu cassette includes a gentamicin resistance gene, and the pMIV-FRTG-mFRT-EA plasmid cannot replicate in *M. methylotrophus*. Therefore, the gentamicin-resistant strain has the mini-Mu cassette inserted into the chromosome. Accordingly, 200 strains were randomly selected and spread on an SEII plate containing 50 mg/L streptomycin and 20 mg/L gentamicin, followed by culturing at 37° C. overnight. Then, bacterial cells which were present on the medium surface of about 0.3 square centimeters were scraped off and inoculated into an SEII production medium (5 ml) containing 50 mg/l streptomycin and 20 mg/L gentamicin, and the cells were cultured with shaking at 37° C. for 48 hours. After completion of the culture, the bacterial cells were removed by centrifugation, and the concentration of L-lysine in each culture supernatant was measured using a Biotech-analyzer AS-210 (manufactured by Sakura Seiki Co., Ltd.). The strain with the highest concentration of L-lysine was selected and designated as #403-11Gm.

Reference Example 8

Determination of the Transfer Site in #403-11-Gm

Next, the site containing the transferred mini-Mu cassette on the chromosome of the #403-11-Gm strain was determined. The chromosomal DNA of the #403-11 strain was prepared and completely digested with the SalI restriction enzyme. The resulting fragment was ligated to the pHSG398 vector, and selection was performed in an LB agar medium containing 12.5 mg/L chloramphenicol and 25 mg/L gentamicin to prepare a plasmid DNA from the resulting colonies. There is a cloned kanamycin resistance gene on the mini-Mu cassette, as well as the chromosomal DNA around the transfer site in the plasmid. The nucleotide sequence of the plasmid was determined using a sequencing primer (SEQ ID NO: 12), which was designed in the attR region present on the right hand edge of the mini-Mu cassette, to thereby determine the transfer site of the mini-Mu cassette. It is also possible to construct a strain identical to #403-11Gm based on the information of the transfer region determined by the above-described method.

Reference Example 9

Elimination of the Antibiotic-Resistant Marker from #403-11-Gm (pFLP31), and Acquisition of the #403-11 Strain Construction of pAYCTER3

Synthetic DNAs of SEQ ID NO: 13 and SEQ ID NO: 14, designed to contain the pUC19 multi-cloning site, were annealed by a well-known method to produce a polylinker. The polylinker was designed to have the same terminal as that of the fragment cleaved with restriction enzymes EcoRI and BglII. Moreover, the primers of SEQ ID NO: 15 and SEQ ID NO: 16 were synthesized, and the region encoding the rrnB terminator sequence was amplified by PCR from the chromosomal DNA of the *Escherichia coli* K-12 strain prepared by a conventional method (Saito and Miura [Biochim. Biophys. Acta, 72, 619 (1963)]). The primers of SEQ ID NO: 13 and SEQ ID NO: 14 were designed to have the recognition sequences of the restriction enzymes BglII and BclI, respectively. PCR was performed using Pyrobest DNA polymerase (manufactured by Takara Bio Inc.) under reaction conditions recommended by the manufacturer. The resulting PCR fragment was digested with restriction enzymes BglII and BclI, and the PCR fragment was ligated to the above-mentioned polylinker, to produce a DNA fragment of about 400 bp. The ligation reaction was performed with a DNA Ligation Kit Ver. 2.1 (manufactured by Takara Bio Inc.) under reaction conditions recommended by the manufacturer. Then, a fragment of about 9.2 kbp, obtained by cleaving pAYC32 (J. Gen. Microbiol., 137, 169-178 (1991)) with restriction enzymes EcoRI and BamHI, was collected, and the above-mentioned DNA fragment was inserted to construct the pAYCTER3 expression plasmid, which is capable of functioning in *M. methylotrophus* NCIMB 10515. pAYCTER3 lacks a sequence upstream on the 5' side of the strA gene, and alternatively has a pUC19 multi-cloning site and an rrnB terminator.

Construction of pFLP31

The gentamicin resistance gene from the #403-11Gm strain constructed in Reference Example 7 was designed so that it is located between two FRT sequences, so the drug resistance gene can be eliminated from the chromosome by a reaction with FLP recombinase. pAYCTER3 constructed by the above-mentioned method was digested with BamHI-SmaI, and a 3.3-kbp fragment obtained by cleaving pCP20 (Proceedings of the National Academy of Sciences of the United States of America, (2000) 97, 6640-6645) with SmaI-BamHI containing an FLP recombinase was inserted. The resulting plasmid was designated as pFLP31. The plasmid pCP20 was registered at the *E. coli* Genetic Stock Center as CGSC strain #7629, and it is available from the Center.

Elimination of the Antibiotic-Resistance Marker pAET7 was eliminated from #403-11Gm by a known method to obtain a streptomycin-sensitive strain. The above-mentioned plasmid pFLP31 was introduced into the strain by electroporation, and the cells were inoculated onto an SEII agar medium containing 50 mg/L streptomycin and 0.5 g/L L-methionine. The resulting strain was suspended to an appropriate concentration in an SEII agar medium containing 50 mg/L streptomycin and 0.5 g/L L-methionine. The suspension was heated to 42° C. for 1 hour and diluted to form single colonies, and the cells were inoculated onto an SEII agar medium containing 50 mg/L streptomycin and 0.5 g/L L-methionine. From the colonies, strains sensitive to gentamicin were selected. Then, pAET7 was eliminated from the strain to obtain a streptomycin-sensitive strain, which was designated as #403-11. When the #403-11 strain and a control strain (#403 strain) were cultured in an SEII production medium containing 0.075 g/L L-methionine and 2.5 g/L sodium pyruvate, the amount of Lys that was produced increased. The amount of Lys produced by the #403 strain was defined as 100, and the relative value of the amount of Lys produced by the #403-11 strain was calculated and shown in Table 3.

TABLE 3

| Strain | Relative amount of produced Lys (%) |
|---|---|
| #403 | 100 |
| #403-11 | 108 |

Reference Example 10

Confirmation of Increased DDPS Activity

In #403-11 obtained as described above, 8 copies of the lysE24dapA cassette were transferred to the chromosome. Therefore, the activity of dihydrodipicolinate synthase encoded by dapA was increased in the #403-11 strain. The dihydrodipicolinate synthase activity was measured by modifying a known method (Journal of Biological Chemistry, 240, 4710-4716 (1965)). Specifically, a reaction solution was prepared so as to contain 50 mM imidazole-HCl (pH 7.4), 2 mM L-aspartate-β-semialdehyde, 2 mM sodium pyruvate, and a cell extract, and the final volume of the solution was adjusted to 1 ml. The results are shown in Table 4.

TABLE 4

| Bacterial strain | Specific activity (milliunit/milligram protein) |
|---|---|
| AS1 | 12 |
| #403-11 | 129 |

The amount of enzyme that produces 1 micromol of a product per minute was defined as 1 unit.

Reference Example 11

Construction of the pBGEA Plasmid, and Construction of #403-11/pBGEA (1) Construction of the pBGEA Plasmid Carrying an L-Lysine Biosynthetic Enzyme Gene (dapA*) and a Gene Having L-Lysine Export Activity (lysE24)

In order to introduce the dapA* and LysE24 genes into a bacterium belonging to the genus *Methylophilus*, pBHR1 (Antoine, R. and Locht, C., Molecular Microbiology, 6, 1785-99. (1992)) was used to construct pBGEA for expressing dapA* and LysE24. First, pBHR1 was digested with the DraI restriction enzyme, and the resulting fragment was added to a phenol/chloroform solution and mixed to terminate the reaction. After the reaction mixture was centrifuged, the upper layer was collected, and DNA was collected by ethanol precipitation. The resulting DNA fragment was blunt-ended using a DNA Blunting kit (manufactured by Takara Shuzo).

The dapA* and LysE24 genes were obtained from pRSlysEdapA (JP 2003-61687 A, U.S. Pat. No. 7,169,587). The *E. coli* JM109 strain transformed with the pRSlysEdapA plasmid was designated as AJ13832 and deposited at National Institute of Advanced Industrial Science and Technology, International Patent Organism Depositary on Jun. 4, 2001 under the accession number FERM P-18371. Then, the deposit was converted to an international deposit under the provisions of the Budapest Treaty on May 13, 2002 under the accession number FERM BP-8042. First, pRSlysEdapA was digested with restriction enzymes EcoRI and BglII, and the resulting fragment was added to a phenol/chloroform solution and mixed to terminate the reaction. After the reaction mixture was centrifuged, the upper layer was collected, and DNA was collected by ethanol precipitation. Then, the DNA fragment of interest was separated by electrophoresis on an 0.8% agarose gel, and the DNA fragment of about 2.0 Kbp was collected by using EASY TRAP ver. 2 (DNA collection kit, manufactured by Takara Shuzo). The resulting DNA fragment was blunt-ended with a BKL kit (manufactured by Takara Shuzo) and phosphorylated.

The digestion product of pBHRI, and the dapA* and LysE24 gene region fragments prepared as described above were ligated by using a DNA Ligation Kit Ver. 2 (manufactured by Takara Shuzo). This ligation product was used to transform *Escherichia coli* (*E. coli* JM109 competent cells, manufactured by Takara Shuzo), and the cells were inoculated into an LB agar medium containing 20 mg/L of kanamycin and incubated overnight at 37° C. The colonies that appeared on the agar medium were inoculated into an LB liquid medium containing 20 mg/L of kanamycin and cultured at 37° C. for 8 hours with shaking. Plasmid DNA was extracted from each culture medium by the alkali-SDS method, and the structure of each plasmid was confirmed by digestion with restriction enzymes and determination of the nucleotide sequence. A plasmid with identical transcription directions of the chloramphenicol resistance gene and the dapA* and lysE24 genes was selected as pBHR-EA.

A gentamicin resistant marker was introduced into pBHR-EA obtained as described above to construct the pBGEA plasmid. First, pBHR-EA was digested with the restriction enzyme NcoI, and the resulting fragment was added to a phenol/chloroform solution and mixed to terminate the reaction. After the reaction mixture was centrifuged, the upper layer was collected, and DNA was collected by ethanol precipitation. The resulting DNA fragment was blunt-ended by using a DNA Blunting kit (manufactured by Takara Shuzo). The gentamicin resistance gene region was amplified by PCR using pML122 (Monika Labes, Alfred Puhler, and Reinhard Simon, Gene, 89, (1990), 37-46) as the template DNA and pGm-f (SEQ ID NO: 17) and pGm-r (SEQ ID NO: 18) as primers, and PCR was performed under the following conditions: denaturation at 94° C. for 10 seconds, annealing at 60° C. for 30 seconds, and extension at 72° C. for 90 seconds. The PCR was performed using Pyrobest DNA polymerase (manufactured by Takara Shuzo). The resulting gentamicin resistance gene fragment was blunt-ended by using a BKL kit (manufactured by Takara Shuzo) and phosphorylated.

The digestion product of pBHR-EA and the gentamicin resistance gene region fragment prepared as described above were ligated by using a DNA Ligation Kit Ver. 2 (manufactured by Takara Shuzo). This ligation product was used to transform *Escherichia coli* (*E. coli* JM109 competent cells, manufactured by Takara Shuzo), and the cells were inoculated onto an LB agar medium containing 20 mg/L of gentamicin and incubated overnight at 37° C. The colonies that appeared on the agar medium were inoculated into an LB liquid medium containing 20 mg/L of gentamicin and cultured at 37° C. for 8 hours with shaking. Plasmid DNA was extracted from each culture medium by the alkali-SDS method, and the structure of each plasmid was confirmed by digestion with restriction enzymes and determination of the nucleotide sequence to obtain pBGEA. pBGEA was then introduced into the #403-11 strain prepared in Example 9, in which the lysE24 and dapA* genes had been incorporated into the chromosome, to enhance the lysE24 and dapA* genes. The strain was designated as #403-11/pBGEA. When #403-11/pBGEA and the control strain #403-11 were cultured in an SEII production medium containing 20 mg/L kanamycin, 50 mg/L gentamicin (the medium for the control strain contains no gentamicin), 0.075 g/L L-methionine, and 2.5 g/L sodium pyruvate, the amount of Lys increased. The amount of Lys produced by the #403-11 strain was defined as 100, and the relative value of the amount of Lys produced by the #403-11/pBGEA strain was calculated and shown in Table 5. It was found that the introduction of the plasmid increased the amount of Lys produced by the #403-11 strain.

TABLE 5

| Strain | Relative amount of produced Lys (%) |
|---|---|
| #403-11 | 100 |
| #403-11/pBGEA | 111 |

Reference Example 12

Construction of the pRSlysA, pRSddh, pRSdapB, pRSasd, and pRSask Plasmids, Introduction of the Plasmids into the #403-11/pBGEA Strain, and Evaluation of L-Lysine Productivity Next, expression plasmids carrying each Lys biosynthetic gene were constructed, and the plasmids were introduced into the #403-11/pBGEA strain, and the effects on L-lysine productivity were investigated.

<1> Construction of the pRSlysA Plasmid

The diaminopimelate decarboxylase gene (lysA) from *Methylophilus methylotrophus* was obtained by PCR using two oligonucleotide primers prepared based on a known sequence (SEQ ID NO: 13 in WO2000/061723) and using the chromosomal DNA of *Methylophilus methylotrophus* as the template. PCR was performed using plysA-f (SEQ ID NO: 19:) and plysA-r (SEQ ID NO: 20) as primers, under the following conditions for 25 cycles: denaturation at 94° C. for 20 seconds, annealing at 55° C. for 30 seconds, and extension at 72° C. for 60 seconds. The amplified lysA gene fragment from *M. methylotrophus* was digested with Sse8387I-XbaI, recognition sites of which had been added into the primer sequence, and the resulting fragment was ligated to pRStac (JP 2003-61687 A, U.S. Pat. No. 7,169,587) which had been digested with Sse8387I-XbaI. The plasmid was designated as pRSlysA.

<2> pRSddh

The diaminopimelate hydrogenase gene (ddh) from *Brevibacterium lactofermentum* was obtained by amplification with PCR using two kinds of oligonucleotide primers prepared based on the known nucleotide sequence of ddh based on *Corynebacterium glutamicum* (Ishino, S. et al. Nucleic acid res. 15, 3917 (1987)) and using the chromosomal DNA of *Brevibacterium lactofermentum* 2256 strain (ATCC 13869 strain) as the template. PCR was performed using pddh-f (SEQ ID NO: 21) and pddh-r (SEQ ID NO: 22) as primers, under the following conditions for 25 cycles: denaturation at 94° C. for 20 seconds, annealing at 55° C. for 30 seconds, and extension at 72° C. for 60 seconds. The amplified ddh gene fragment was digested with Sse8387I-XbaI, recognition sites of which had been added into the primer sequence, and the resulting fragment was ligated to pRStac (JP 2003-61687 A, U.S. Pat. No. 7,169,587) digested with Sse8387I-XbaI. The plasmid was designated as pRSddh.

<3> pRSdapB

The dihydrodipicolinate reductase gene (dapB) from *E. coli* was amplified by PCR using two oligonucleotide primers prepared based on the known nucleotide sequence and using the chromosomal DNA of *E. coli* as the template. PCR was performed using pdapB-f (SEQ ID NO: 23:) and pdapB-r (SEQ ID NO: 24) as primers, under the following conditions for 25 cycles: denaturation at 94° C. for 20 seconds, annealing at 55° C. for 30 seconds, and extension at 72° C. for 60 seconds. The amplified dapB gene fragment was digested with Sse8387I-XbaI, recognition sites of which had been added into the primer sequence, and the resulting fragment was ligated to pRStac (JP 2003-61687 A, U.S. Pat. No. 7,169, 587) which had been digested with Sse8387I-XbaI. The plasmid was designated as pRSdapB.

<4> pRSlasd

The aspartate-semialdehyde dehydrogenase gene (asd) from *E. coli* was amplified by PCR using two oligonucleotide primers prepared based on the known nucleotide sequence using the chromosomal DNA of *E. coli* as the template. PCR was performed using pasd-f (SEQ ID NO: 25) and pasd-r (SEQ ID NO: 26) as primers, under the following conditions for 25 cycles: denaturation at 94° C. for 20 seconds, annealing at 55° C. for 30 seconds, and extension at 72° C. for 60 seconds. The amplified ddh gene fragment was digested with Sse8387I-XbaI, recoinition sites of which had been added into the primer sequence, and the resulting fragment was ligated to pRStac (JP 2003-61687 A, U.S. Pat. No. 7,169,587) which had been digested with Sse8387I-XbaI. The plasmid was designated as pRSasd.

<5> pRSask

The aspartokinase gene (ask) from *Methylophilus methylotrophus* was obtained by PCR using two oligonucleotide primers prepared based on a known sequence (SEQ ID NO: 5 in WO2000/061723) and using a chromosomal DNA of *Methylophilus methylotrophus* as a template. PCR was performed using pask-f (SEQ ID NO: 27:) and pask-r (SEQ ID NO: 28:) as primers. The following cycle was repeated 25 times: denaturation at 94° C. for 20 seconds, annealing at 55° C. for 30 seconds, and extension at 72° C. for 90 seconds. The amplified ask gene fragment from *M. methylotrophus* was digested with Sse8387I-XbaI, recognition sites of which had been added into the primer and blunt-ended, and the resulting fragment was ligated to pRStac (JP 2003-61687 A, U.S. Pat. No. 7,169,587) which had been digested with Sse8387I and blunt-ended. The plasmid was designated as pRSask.

<6> Introduction and Evaluation of the Plasmids

The five plasmids prepared as described above were separately introduced into the #403-11/pBGEA strain prepared in Example 11, and the resulting strains were cultured in an SEII production medium containing 0.075 g/L L-methionine and 2.5 g/L sodium pyruvate. However, Lys productivity did not improve in all the strains. In the strain with ddh, Lys productivity was reduced.

Reference Example 13

Enhancement of ddh+lysA in Combination, Construction of the pDA Plasmid, and Evaluation of Productivity of L-Lysine The #403-11 strain was modified so that expression of the lysE24 and dapA* genes, which are effective for improving Lys production in *M. methylotrophus*, was sufficiently enhanced by gene incorporation and plasmid introduction. This strain was used to determine the next limiting factor in Lys production. As shown in Reference Example 12, when the genes were separately increased, the effective gene could not be determined. Therefore, various plasmids were constructed to enhance the genes in combination, each carrying two genes, and introduced into the #403-11 strain. As a result, it was found that by increasing the expression of both the lysA and ddh genes, the productivity of L-lysine was improved.

Diaminopimelate dehydrogenase encoded by ddh was thought to reversibly catalyze both the production and degradation reactions of diaminopimelic acid, and that enhancing ddh alone promoted not only production but also degradation of diaminopimelic acid. On the other hand, diaminopimelate decarboxylase, which catalyzes the reaction subsequent to that of diaminopimelate dehydrogenase, is an irreversible enzyme that causes a decarboxylation reaction prior to L-lysine production. It was thought that enhancing both diaminopimelate dehydrogenase and diaminopimelate decarboxylase together prevented degradation of diaminopimelic acid by diaminopimelate dehydrogenase and promoted synthesis of diaminopimelic acid.

Specifically, the pRSddh plasmid was digested with SapI, and the resulting fragment was blunt-ended and dephospho-rylated to produce a vector, into which a PCR-amplified DNA fragment including the lysA gene region containing the tac promoter region. PCR amplification was performed using the pRSlysA plasmid as the template and ptac-f (SEQ ID NO: 29:) and plysA-r (SEQ ID NO: 20:) as primers. The following cycle was repeated 25 times: denaturation at 94° C. for 20 seconds, annealing at 55° C. for 30 seconds, and extension at 72° C. for 60 seconds. The resulting PCR-amplified fragment was digested with XbaI, and the resulting fragment was blunt-ended and ligated to the above-mentioned vector. In the resulting plasmid, the transcription directions of the ddh and lysA genes were identical, and the plasmid was designated as pDA. When a strain into which the pDA was introduced, (#403-11/pBGEA/pDA) and the control strain #403-11/pBGEA, were cultured in an SEII production medium containing 20 mg/L kanamycin, 50 mg/L gentamicin, and 50 mg/L streptomycin (the medium for the control strain contains no streptomycin), 0.075 g/L L-methionine, and 2.5 g/L sodium pyruvate, the amount of Lys increased. The amount of Lys produced by the #403-11/pBGEA strain was defined as 100, and the relative value of the amount of Lys produced by the #403-11/pBGEA/pDA strain was calculated and shown in Table 6.

TABLE 6

| Strain | Relative amount of produced Lys (%) |
| --- | --- |
| #403-11/pBGEA | 100 |
| #403-11/pBGEA/pDA | 120 |

Reference Example 14

Enhancement of Further L-Lysine Biosynthetic Genes in Combination, Construction of pBDAS (lysA+ddh+dapB+asd), and Evaluation of L-Lysine Productivity It was found that the L-lysine productivity was improved by increasing the expression of both the ddh and lysA genes in combination, since these genes are capable of catalyzing two sequential reactions in the biosynthesis pathway. The effect of enhancing other enzyme genes in combination with ddh+lysA was investigated and it was found that the use of dapB and asd in combination with ddh and lysA improved L-lysine production.

Specifically, the pRSdapB plasmid was digested with EcoRI, and the resulting fragment was blunt-ended and dephosphorylated to prepare a vector. The plasmid pDA was digested with HpaI-SapI, and the resulting DNA fragment of 2.5 kbp, which includes lysA and ddh which each have a tac promoter upstream of the genes, was collected and blunt-ended to be ligated to the vector, to thereby construct pBDA. The plasmid was found to have the ddh and lysA genes inserted upstream of dapB so that the direction of ddh and lysA and the direction of dapB were identical. The pBDA plasmid was further digested with SapI, and the resulting fragment was blunt-ended and dephosphorylated to prepare a vector. A PCR-amplified DNA fragment including the asd gene region containing a tac promoter region was then inserted into the vector. PCR amplification was performed using the pRSasd plasmid as the template and ptac-f and pasd-r as primers. The following cycle was repeated 25 times: denaturation at 94° C. for 20 seconds, annealing at 55° C. for 30 seconds, and extension at 72° C. for 90 seconds. The resulting PCR-amplified fragment was blunt-ended and phosphorylated, and the fragment was ligated to the above-mentioned vector. The resulting plasmid was designated as pBDAS. When a strain into which the pBDAS plasmid was introduced (#403-11/pBGEA/pBDAS), and a control strain #403-11/pBGEA, were cultured in an SEII production medium containing 20 mg/L kanamycin, 50 mg/L gentamicin, and 50 mg/L streptomycin (the medium for the control strain contains no streptomycin), 0.075 g/L L-methionine, and 2.5 g/L sodium pyruvate, the amount of Lys increased. The amount of Lys produced by the #403-11/pBGEA strain was defined as 100, and the relative value of the amount of Lys produced by the #403-11/pBGEA/pBDAS strain was calculated and is shown in Table 7.

TABLE 7

| Strain | Relative amount of produced Lys (%) |
|---|---|
| #403-11/pBGEA | 100 |
| #403-11/pBGEA/pDA | 120 |
| #403-11/pBGEA/pBDAS | 143 |

Example: 1

The Effect on Fermentation Results of the Rate of Increase in Ionic Concentration The effect on L-lysine fermentation of the rate of increase in ionic concentration was determined with the #403-11/pBGEA/pBDAS strain.

First, all of the bacterial cells obtained by culturing the #403-11/pBGEA/pBDAS strain in SEII agar medium for 24 hours at 37° C. were scraped off a single plate, and the entire suspension solution was inoculated into a 1-liter jar fermenter containing 300 mL of main culture medium, and culturing was conducted at 34° C. at pH 6.6. The composition of the main culture medium is indicated below.

| Main culture medium: | |
|---|---|
| $K_2HPO_4$ | 1.9 g/L |
| $NaH_2PO_4$ | 1.56 g/L |
| Sodium pyruvate | 2.5 g/L |
| $MgSO_4 \cdot 7H_2O$ | 0.2 g/L |
| $(NH_4)_2SO_4$ | 4.97 g/L |
| L-methionine | 0.65 g/L |
| Citric acid | 1 g/L |
| $MgSO_4 \cdot 7H_2O$ [sic] | 1 g/L |
| $CuSO_4 \cdot 5H_2O$ | 25 μg/L |
| $MnSO_4 \cdot 5H_2O$ | 125 μg/L |
| $ZnSO_4 \cdot 7H_2O$ | 115 μg/L |
| $CaCl_2 \cdot 2H_2O$ | 0.36 g/L |
| $FeCl_3 \cdot 6H_2O$ | 48.5 mg/L |
| Methanol | 2% (vol/vol) |
| Streptomycin sulfate | 50 mg/L |
| Gentamicin sulfate | 50 mg/L |
| Kanamycin sulfate | 25 mg/L |

Components other than methanol and the antibiotics were mixed, sterilized by filtration. Subsequently, methanol and filter-sterilized antibiotics were added.

During culturing, the pH was adjusted to 6.6 by the addition of ammonia gas. When the methanol in the medium dropped to 0.2% or below, a 100 percent methanol solution was fed by fed-batch culturing.

In Lys fermentation, a nitrogen source was added to the medium for Lys production and ammonium sulfate was added to the medium to supply counter ions for the targeted amino acid. In the course of adding ammonium sulfate to the medium, the effect of feeding resulted in the rate of increase in total ionic strength in the medium of 0.03 mol/m$^3$/hour, 0.02 mol/m$^3$/hour, and 0.012 mol/m$^3$/hour were examined.

The results are given in Table 8. The production is given as a relative value where production under conditions of a rate of increase in ionic strength of 0.03 mol/m$^3$/hour was adopted as 100 percent. As shown in Table 1, as the rate of increase in ionic strength dropped, production was found to rise. As a result, it was determined that L-lysine production was enhanced by conducting feeding so that the rate of increase in ionic strength in the medium was maintained at 0.02 mol/m$^3$/hour, desirably 0.012 mol/m$^3$/hour or less.

TABLE 8

| Rate of increase in ionic strength (mol/m$^3$/hour) | Production Relative value (%) |
|---|---|
| 0.03 | 100 |
| 0.02 | 106 |
| 0.012 | 133 |

Example: 2

To examine the effect of the reduced rate of increase in ionic strength on the fermentation, a nitrogen source of ammonium chloride and glutamic acid was employed as a monovalent counter ion. The glutamic acid was employed in the form of a solution that had been neutralized with ammonia.

First, in the same manner as in Example 1, All of the bacterial cells obtained by culturing the #403-11/pBGEA/pBDAS strain in SEII agar medium for 24 hours at 37° C. were scraped up, and the entire suspension solution was inoculated into a 1-liter jar fermenter containing 300 mL of main culture to 6.6 medium, and culturing was conducted at pH 6.6 and 34° C. The pH was adjusted during culturing by the addition of ammonia gas. When the methanol in the medium dropped to 0.2% or below, a 100% methanol solution was fed to conduct fed-batch culturing.

In the course of adding nitrogen sources in the form of ammonium chloride and glutamic acid to the medium, these compounds were fed so as to achieve rates of increase in ionic strength of 0.008 mol/m$^3$/hour and 0.006 mol/m$^3$/hour.

The results are given in Table 9. The production is given as a relative value where production under conditions of a rate of increase in ionic strength of 0.03 mol/m$^3$/hour with the use of ammonium sulfate was adopted as 100 percent. As a result of the test, it was confirmed that an increase in the rate of ionic strength of 0.012 mol/m$^3$/hour or less further increased production.

TABLE 9

| Nitrogen source | Rate of increase in ionic strength (mol/m$^3$/hour) | Production Relative value (%) |
|---|---|---|
| Ammonium sulfate | 0.03 | 100 |
| Ammonium sulfate | 0.02 | 106 |
| Ammonium sulfate | 0.012 | 133 |
| Ammonium chloride | 0.008 | 148 |
| Glutamic acid | 0.006 | 147 |

INDUSTRIAL APPLICABILITY

The present invention enhances the production of carboxylic acid by methanol-assimilating bacteria.

We claim:

1. A method for producing L-lysine by fermentation comprising

A) culturing a *Methylophilus methylotrophus* bacterium in a liquid fermentation medium containing methanol and a counter ion, B) collecting L-lysine from the medium or the bacterium, wherein the total ionic strength in the fermentation medium is controlled to increase at a rate of 0.02 mol/m³/hour or less by adding a composition comprising methanol and a counter ion to the medium by fed-batch culturing, and wherein said counter ion is derived from a substance selected from the group consisting of ammonium sulfate, ammonium chloride, ammonium glutamate, ammonium succinate, ammonium fumarate, ammonium aspartate, urea, and combinations thereof.

2. The method according to claim 1, wherein the total ionic strength is controlled during the proliferation period of the *Methylophilus methylotrophus* bacterium.

3. The method according to claim 1, wherein said *Methylophilus methylotrophus* bacterium has been modified to increase the activity of an enzyme selected from the group consisting of diaminopimelate dehydrogenase, diaminopimelate decarboxylase, aspartate semialdehyde dehydrogenase, and combinations thereof.

4. The method according to claim 3, wherein DNA encoding feedback-resistant dihydrodipicolinate synthase and/or aspartokinase is present in said *Methylophilus methylotrophus* bacterium.

5. The method according to claim 3, wherein DNA encoding mutant lysE protein which promotes the export of L-lysine to the outside of the bacterium is present in said *Methylophilus methylotrophus* bacterium.

* * * * *

SEQUENCE LISTING

<160> NUMBER OF SEQ ID NOS: 59

<210> SEQ ID NO 1
<211> LENGTH: 25
<212> TYPE: DNA
<213> ORGANISM: Artificial sequence
<220> FEATURE:
<223> OTHER INFORMATION: primer

<400> SEQUENCE: 1
aaaaagctta acacagaaaa aagcc                                              25

<210> SEQ ID NO 2
<211> LENGTH: 28
<212> TYPE: DNA
<213> ORGANISM: Artificial sequence
<220> FEATURE:
<223> OTHER INFORMATION: primer

<400> SEQUENCE: 2
aaactgcagt ggtcgaaaaa aaaagccc                                           28

<210> SEQ ID NO 3
<211> LENGTH: 23
<212> TYPE: DNA
<213> ORGANISM: Artificial sequence
<220> FEATURE:
<223> OTHER INFORMATION: primer

<400> SEQUENCE: 3
aaagaattcg agctcggtac ctc                                                23

<210> SEQ ID NO 4
<211> LENGTH: 23
<212> TYPE: DNA
<213> ORGANISM: Artificial sequence
<220> FEATURE:
<223> OTHER INFORMATION: primer

<400> SEQUENCE: 4
aaaaagcttg catgcaggcc tct                                                23

<210> SEQ ID NO 5
<211> LENGTH: 21
<212> TYPE: DNA
<213> ORGANISM: Artificial sequence
<220> FEATURE:
<223> OTHER INFORMATION: primer

<400> SEQUENCE: 5
aaaggatccg catgccgttg a                                                  21

<210> SEQ ID NO 6
<211> LENGTH: 93
<212> TYPE: DNA
<213> ORGANISM: Artificial sequence
<220> FEATURE:
<223> OTHER INFORMATION: primer

<400> SEQUENCE: 6
aaagaattcc gatacaatta aaggctcctt ttggagcctt tttttggag attttcaacg         60

```
tgaaaaaatt attattcgca attccaagct aat                                    93
```

```
<210> SEQ ID NO 7
<211> LENGTH: 36
<212> TYPE: DNA
<213> ORGANISM: Artificial sequence
<220> FEATURE:
<223> OTHER INFORMATION: primer

<400> SEQUENCE: 7
cattctagat ccctaaactt tacagcaaac cggcat                                 36

<210> SEQ ID NO 8
<211> LENGTH: 22
<212> TYPE: DNA
<213> ORGANISM: Artificial sequence
<220> FEATURE:
<223> OTHER INFORMATION: primer

<400> SEQUENCE: 8
cacagagaca tattgcccgt tg                                                22

<210> SEQ ID NO 9
<211> LENGTH: 29
<212> TYPE: DNA
<213> ORGANISM: Artificial sequence
<220> FEATURE:
<223> OTHER INFORMATION: primer

<400> SEQUENCE: 9
catctgtttc atttgaagcg cgaaagcta                                         29

<210> SEQ ID NO 10
<211> LENGTH: 21
<212> TYPE: DNA
<213> ORGANISM: Artificial sequence
<220> FEATURE:
<223> OTHER INFORMATION: primer

<400> SEQUENCE: 10
cgccagccag gacagaaatg c                                                 21

<210> SEQ ID NO 11
<211> LENGTH: 22
<212> TYPE: DNA
<213> ORGANISM: Artificial sequence
<220> FEATURE:
<223> OTHER INFORMATION: primer

<400> SEQUENCE: 11
gtccagcggt ttttcttggg ct                                                22

<210> SEQ ID NO 12
<211> LENGTH: 29
<212> TYPE: DNA
<213> ORGANISM: Artificial sequence
<220> FEATURE:
<223> OTHER INFORMATION: primer

<400> SEQUENCE: 12
catctgtttc atttgaagcg cgaaagcta                                         29

<210> SEQ ID NO 13
<211> LENGTH: 57
<212> TYPE: DNA
<213> ORGANISM: Artificial sequence
```

```
<220> FEATURE:
<223> OTHER INFORMATION: primer

<400> SEQUENCE: 13
aattcgagct cggtacccgg ggatcctcta gagtcgacct gcaggcatgc aagctta        57

<210> SEQ ID NO 14
<211> LENGTH: 57
<212> TYPE: DNA
<213> ORGANISM: Artificial sequence
<220> FEATURE:
<223> OTHER INFORMATION: primer

<400> SEQUENCE: 14
gatctaagct tgcatgcctg caggtcgact ctagaggatc cccgggtacc gagctcg        57

<210> SEQ ID NO 15
<211> LENGTH: 30
<212> TYPE: DNA
<213> ORGANISM: Artificial sequence
<220> FEATURE:
<223> OTHER INFORMATION: primer

<400> SEQUENCE: 15
ctatgatcat ttgcctggcg gcagtagcgc        30

<210> SEQ ID NO 16
<211> LENGTH: 31
<212> TYPE: DNA
<213> ORGANISM: Artificial sequence
<220> FEATURE:
<223> OTHER INFORMATION: primer

<400> SEQUENCE: 16
cttagatctc aaaaagagtt tgtagaaacg c        31

<210> SEQ ID NO 17
<211> LENGTH: 21
<212> TYPE: DNA
<213> ORGANISM: Artificial sequence
<220> FEATURE:
<223> OTHER INFORMATION: primer

<400> SEQUENCE: 17
cgccagccag gacagaaatg c        21

<210> SEQ ID NO 18
<211> LENGTH: 22
<212> TYPE: DNA
<213> ORGANISM: Artificial sequence
<220> FEATURE:
<223> OTHER INFORMATION: primer

<400> SEQUENCE: 18
gtccagcggt ttttcttggg ct        22

<210> SEQ ID NO 19
<211> LENGTH: 39
<212> TYPE: DNA
<213> ORGANISM: Artificial sequence
<220> FEATURE:
<223> OTHER INFORMATION: primer

<400> SEQUENCE: 19
aaacccgggg atcctgagcg ccaataccct caaacgcct        39
```

<210> SEQ ID NO 20
<211> LENGTH: 43
<212> TYPE: DNA
<213> ORGANISM: Artificial sequence
<220> FEATURE:
<223> OTHER INFORMATION: primer

<400> SEQUENCE: 20
tttcccgggc ttggcggctt cggttttttt attaggggtt gcc        43

<210> SEQ ID NO 21
<211> LENGTH: 41
<212> TYPE: DNA
<213> ORGANISM: Artificial sequence
<220> FEATURE:
<223> OTHER INFORMATION: primer

<400> SEQUENCE: 21
acccctgcag ggccaccaca attttggagg attacaagaa c          41

<210> SEQ ID NO 22
<211> LENGTH: 33
<212> TYPE: DNA
<213> ORGANISM: Artificial sequence
<220> FEATURE:
<223> OTHER INFORMATION: primer

<400> SEQUENCE: 22
tcctctagac tcgagctaaa ttagacgtcg cgt                   33

<210> SEQ ID NO 23
<211> LENGTH: 35
<212> TYPE: DNA
<213> ORGANISM: Artificial sequence
<220> FEATURE:
<223> OTHER INFORMATION: primer

<400> SEQUENCE: 23
gcgcctgcag gcgctggtta ctctgaaaac ggtct                 35

<210> SEQ ID NO 24
<211> LENGTH: 46
<212> TYPE: DNA
<213> ORGANISM: Artificial sequence
<220> FEATURE:
<223> OTHER INFORMATION: primer

<400> SEQUENCE: 24
gcatctagag acaatttaaa aacataacac caaaaataaa agggcc     46

<210> SEQ ID NO 25
<211> LENGTH: 40
<212> TYPE: DNA
<213> ORGANISM: Artificial sequence
<220> FEATURE:
<223> OTHER INFORMATION: primer

<400> SEQUENCE: 25 gccectgcag gccggcacat ttatacagca cacatctttg            40

<210> SEQ ID NO 26
<211> LENGTH: 35
<212> TYPE: DNA
<213> ORGANISM: Artificial sequence
<220> FEATURE:
<223> OTHER INFORMATION: primer

<400> SEQUENCE: 26
taatctagaa agattacgcc agttgacgaa gcatc 35

<210> SEQ ID NO 27
<211> LENGTH: 40
<212> TYPE: DNA
<213> ORGANISM: Artificial sequence
<220> FEATURE:
<223> OTHER INFORMATION: primer

<400> SEQUENCE: 27
agggaattct aaaccggata tggcgatggc aggtggtact 40

<210> SEQ ID NO 28
<211> LENGTH: 39
<212> TYPE: DNA
<213> ORGANISM: Artificial sequence
<220> FEATURE:
<223> OTHER INFORMATION: primer

<400> SEQUENCE: 28
taactgcagg aagttttaat agtaccaaca cagcgcatg 39

<210> SEQ ID NO 29
<211> LENGTH: 39
<212> TYPE: DNA
<213> ORGANISM: Artificial sequence
<220> FEATURE:
<223> OTHER INFORMATION: primer

<400> SEQUENCE: 29
aaaagatctc ccgttctgga taatgttttt tgcgccgac 39

<210> SEQ ID NO 30
<211> LENGTH: 20
<212> TYPE: DNA
<213> ORGANISM: Artificial sequence
<220> FEATURE:
<223> OTHER INFORMATION: primer

<400> SEQUENCE: 30
tggactgacg gtggctactc 20

<210> SEQ ID NO 31
<211> LENGTH: 18
<212> TYPE: DNA
<213> ORGANISM: Artificial sequence
<220> FEATURE:
<223> OTHER INFORMATION: primer

<400> SEQUENCE: 31
gaccacgtca ttttccct 18

<210> SEQ ID NO 32
<211> LENGTH: 58
<212> TYPE: DNA
<213> ORGANISM: Artificial sequence
<220> FEATURE:
<223> OTHER INFORMATION: primer

<400> SEQUENCE: 32
ccagcctaca caatcgctca agacgtgtaa tgcacttccg gatgaaactc agggtaag 58

<210> SEQ ID NO 33
<211> LENGTH: 19
<212> TYPE: DNA
<213> ORGANISM: Artificial sequence

```
<220> FEATURE:
<223> OTHER INFORMATION: primer

<400> SEQUENCE: 33
tgccaaatac gggctactg                                          19

<210> SEQ ID NO 34
<211> LENGTH: 18
<212> TYPE: DNA
<213> ORGANISM: Artificial sequence
<220> FEATURE:
<223> OTHER INFORMATION: primer

<400> SEQUENCE: 34
tccgggctca attcactc                                           18

<210> SEQ ID NO 35
<211> LENGTH: 53
<212> TYPE: DNA
<213> ORGANISM: Artificial sequence
<220> FEATURE:
<223> OTHER INFORMATION: primer

<400> SEQUENCE: 35
gagaatagga acttcggaat aggaactaag gaggagctgg ttgcgtttac gtc    53

<210> SEQ ID NO 36
<211> LENGTH: 30
<212> TYPE: DNA
<213> ORGANISM: Artificial sequence
<220> FEATURE:
<223> OTHER INFORMATION: primer

<400> SEQUENCE: 36
gcattacacg tcttgagcga ttgtgtaggc                              30

<210> SEQ ID NO 37
<211> LENGTH: 34
<212> TYPE: DNA
<213> ORGANISM: Artificial sequence
<220> FEATURE:
<223> OTHER INFORMATION: primer

<400> SEQUENCE: 37
cctccttagt tcctattccg aagttcctat tctc                         34

<210> SEQ ID NO 38
<211> LENGTH: 35
<212> TYPE: DNA
<213> ORGANISM: Artificial sequence
<220> FEATURE:
<223> OTHER INFORMATION: primer

<400> SEQUENCE: 38
gaacctgcag gccctgacac gaggtagatt atgtc                        35

<210> SEQ ID NO 39
<211> LENGTH: 55
<212> TYPE: DNA
<213> ORGANISM: Artificial sequence
<220> FEATURE:
<223> OTHER INFORMATION: primer

<400> SEQUENCE: 39
ctttcggcta gaagagcgag atgcagataa aaaaattaaa ggcaattatt ctccg  55
```

<210> SEQ ID NO 40
<211> LENGTH: 879
<212> TYPE: DNA
<213> ORGANISM: Escherichia coli
<220> FEATURE:
<221> NAME/KEY: CDS
<222> LOCATION: (1)..(876)

<400> SEQUENCE: 40

| | | | | | | | | | | | | | | | | |
|---|---|---|---|---|---|---|---|---|---|---|---|---|---|---|---|---|
| atg | ttc | acg | gga | agt | att | gtc | gcg | att | gtt | act | ccg | atg | gat | gaa | aaa | 48 |
| Met | Phe | Thr | Gly | Ser | Ile | Val | Ala | Ile | Val | Thr | Pro | Met | Asp | Glu | Lys | |
| 1 | | | | 5 | | | | | 10 | | | | | 15 | | |
| ggt | aat | gtc | tgt | cgg | gct | agc | ttg | aaa | aaa | ctg | att | gat | tat | cat | gtc | 96 |
| Gly | Asn | Val | Cys | Arg | Ala | Ser | Leu | Lys | Lys | Leu | Ile | Asp | Tyr | His | Val | |
| | | 20 | | | | | 25 | | | | | 30 | | | | |
| gcc | agc | ggt | act | tcg | gcg | atc | gtt | tct | gtt | ggc | acc | act | ggc | gag | tcc | 144 |
| Ala | Ser | Gly | Thr | Ser | Ala | Ile | Val | Ser | Val | Gly | Thr | Thr | Gly | Glu | Ser | |
| | 35 | | | | | 40 | | | | | 45 | | | | | |
| gct | acc | tta | aat | cat | gac | gaa | cat | gct | gat | gtg | gtg | atg | atg | acg | ctg | 192 |
| Ala | Thr | Leu | Asn | His | Asp | Glu | His | Ala | Asp | Val | Val | Met | Met | Thr | Leu | |
| | 50 | | | | | 55 | | | | | 60 | | | | | |
| gat | ctg | gct | gat | ggg | cgc | att | ccg | gta | att | gcc | ggg | acc | ggc | gct | aac | 240 |
| Asp | Leu | Ala | Asp | Gly | Arg | Ile | Pro | Val | Ile | Ala | Gly | Thr | Gly | Ala | Asn | |
| 65 | | | | | 70 | | | | | 75 | | | | | 80 | |
| gct | act | gcg | gaa | gcc | att | agc | ctg | acg | cag | cgc | ttc | aat | gac | agt | ggt | 288 |
| Ala | Thr | Ala | Glu | Ala | Ile | Ser | Leu | Thr | Gln | Arg | Phe | Asn | Asp | Ser | Gly | |
| | | | | 85 | | | | | 90 | | | | | 95 | | |
| atc | gtc | ggc | tgc | ctg | acg | gta | acc | cct | tac | tac | aat | cgt | ccg | tcg | caa | 336 |
| Ile | Val | Gly | Cys | Leu | Thr | Val | Thr | Pro | Tyr | Tyr | Asn | Arg | Pro | Ser | Gln | |
| | | 100 | | | | | 105 | | | | | 110 | | | | |
| gaa | ggt | ttg | tat | cag | cat | ttc | aaa | gcc | atc | gct | gag | cat | act | gac | ctg | 384 |
| Glu | Gly | Leu | Tyr | Gln | His | Phe | Lys | Ala | Ile | Ala | Glu | His | Thr | Asp | Leu | |
| | 115 | | | | | 120 | | | | | 125 | | | | | |
| ccg | caa | att | ctg | tat | aat | gtg | ccg | tcc | cgt | act | ggc | tgc | gat | ctg | ctc | 432 |
| Pro | Gln | Ile | Leu | Tyr | Asn | Val | Pro | Ser | Arg | Thr | Gly | Cys | Asp | Leu | Leu | |
| | 130 | | | | | 135 | | | | | 140 | | | | | |
| ccg | gaa | acg | gtg | ggc | cgt | ctg | gcg | aaa | gta | aaa | aat | att | atc | gga | atc | 480 |
| Pro | Glu | Thr | Val | Gly | Arg | Leu | Ala | Lys | Val | Lys | Asn | Ile | Ile | Gly | Ile | |
| 145 | | | | | 150 | | | | | 155 | | | | | 160 | |
| aaa | gag | gca | aca | ggg | aac | tta | acg | cgt | gta | aac | cag | atc | aaa | gag | ctg | 528 |
| Lys | Glu | Ala | Thr | Gly | Asn | Leu | Thr | Arg | Val | Asn | Gln | Ile | Lys | Glu | Leu | |
| | | | | 165 | | | | | 170 | | | | | 175 | | |
| gtt | tca | gat | gat | ttt | gtt | ctg | ctg | agc | ggc | gat | gat | gcg | agc | gcg | ctg | 576 |
| Val | Ser | Asp | Asp | Phe | Val | Leu | Leu | Ser | Gly | Asp | Asp | Ala | Ser | Ala | Leu | |
| | | 180 | | | | | 185 | | | | | 190 | | | | |
| gac | ttc | atg | caa | ttg | ggc | ggt | cat | ggg | gtt | att | tcc | gtt | acg | gct | aac | 624 |
| Asp | Phe | Met | Gln | Leu | Gly | Gly | His | Gly | Val | Ile | Ser | Val | Thr | Ala | Asn | |
| | 195 | | | | | 200 | | | | | 205 | | | | | |
| gtc | gca | gcg | cgt | gat | atg | gcc | cag | atg | tgc | aaa | ctg | gca | gca | gaa | ggg | 672 |
| Val | Ala | Ala | Arg | Asp | Met | Ala | Gln | Met | Cys | Lys | Leu | Ala | Ala | Glu | Gly | |
| | 210 | | | | | 215 | | | | | 220 | | | | | |
| cat | ttt | gcc | gag | gca | cgc | gtt | att | aat | cag | cgt | ctg | atg | cca | tta | cac | 720 |
| His | Phe | Ala | Glu | Ala | Arg | Val | Ile | Asn | Gln | Arg | Leu | Met | Pro | Leu | His | |
| 225 | | | | | 230 | | | | | 235 | | | | | 240 | |
| aac | aaa | cta | ttt | gtc | gaa | ccc | aat | cca | atc | ccg | gtg | aaa | tgg | gca | tgt | 768 |
| Asn | Lys | Leu | Phe | Val | Glu | Pro | Asn | Pro | Ile | Pro | Val | Lys | Trp | Ala | Cys | |
| | | | | 245 | | | | | 250 | | | | | 255 | | |
| aag | gaa | ctg | ggt | ctt | gtg | gcg | acc | gat | acg | ctg | cgc | ctg | cca | atg | aca | 816 |
| Lys | Glu | Leu | Gly | Leu | Val | Ala | Thr | Asp | Thr | Leu | Arg | Leu | Pro | Met | Thr | |
| | | | 260 | | | | | 265 | | | | | 270 | | | |
| cca | atc | acc | gac | agt | ggt | cgt | gag | acg | gtc | aga | gcg | gcg | ctt | aag | cat | 864 |
| Pro | Ile | Thr | Asp | Ser | Gly | Arg | Glu | Thr | Val | Arg | Ala | Ala | Leu | Lys | His | |

```
                  275                 280                 285
gcc ggt ttg ctg taa                                                      879
Ala Gly Leu Leu
    290
```

<210> SEQ ID NO 41
<211> LENGTH: 292
<212> TYPE: PRT
<213> ORGANISM: Escherichia coli

<400> SEQUENCE: 41

```
Met Phe Thr Gly Ser Ile Val Ala Ile Val Thr Pro Met Asp Glu Lys
  1               5                  10                  15

Gly Asn Val Cys Arg Ala Ser Leu Lys Lys Leu Ile Asp Tyr His Val
             20                  25                  30

Ala Ser Gly Thr Ser Ala Ile Val Ser Val Gly Thr Thr Gly Glu Ser
         35                  40                  45

Ala Thr Leu Asn His Asp Glu His Ala Asp Val Val Met Met Thr Leu
     50                  55                  60

Asp Leu Ala Asp Gly Arg Ile Pro Val Ile Ala Gly Thr Gly Ala Asn
 65                  70                  75                  80

Ala Thr Ala Glu Ala Ile Ser Leu Thr Gln Arg Phe Asn Asp Ser Gly
                 85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290
```

<210> SEQ ID NO 42
<211> LENGTH: 822
<212> TYPE: DNA
<213> ORGANISM: Escherichia coli
<220> FEATURE:
<221> NAME/KEY: CDS
<222> LOCATION: (1)..(822)
<223> OTHER INFORMATION:

<400> SEQUENCE: 42

```
atg cat gat gca aac atc cgc gtt gcc atc gcg gga gcc ggg ggg cgt    48
Met His Asp Ala Asn Ile Arg Val Ala Ile Ala Gly Ala Gly Gly Arg
1               5                   10                  15 atg ggc cgc cag ttg att cag gcg gcg ctg gca tta gag ggc gtg cag    96
Met Gly Arg Gln Leu Ile Gln Ala Ala Leu Ala Leu Glu Gly Val Gln
            20                  25                  30 ttg ggc gct gcg ctg gag cgt gaa gga tct tct tta ctg ggc agc gac    144
Leu Gly Ala Ala Leu Glu Arg Glu Gly Ser Ser Leu Leu Gly Ser Asp
        35                  40                  45 gcc ggt gag ctg gcc gga gcc ggg aaa aca ggc gtt acc gtg caa agc    192
Ala Gly Glu Leu Ala Gly Ala Gly Lys Thr Gly Val Thr Val Gln Ser
50                  55                  60 agc ctc gat gcg gta aaa gat gat ttt gat gtg ttt atc gat ttt acc    240
Ser Leu Asp Ala Val Lys Asp Asp Phe Asp Val Phe Ile Asp Phe Thr
65                  70                  75                  80 cgt ccg gaa ggt acg ctg aac cat ctc gct ttt tgt cgc cag cat ggc    288
Arg Pro Glu Gly Thr Leu Asn His Leu Ala Phe Cys Arg Gln His Gly
                85                  90                  95 aaa ggg atg gtg atc ggc act acg ggg ttt gac gaa gcc ggt aaa caa    336
Lys Gly Met Val Ile Gly Thr Thr Gly Phe Asp Glu Ala Gly Lys Gln
            100                 105                 110 gca att cgt gac gcc gct gcc gat att gcg att gtc ttt gct gcc aat    384
Ala Ile Arg Asp Ala Ala Ala Asp Ile Ala Ile Val Phe Ala Ala Asn
        115                 120                 125 ttt agc gtt ggc gtt aac gtc atg ctt aag ctg ctg gag aaa gca gcc    432
Phe Ser Val Gly Val Asn Val Met Leu Lys Leu Leu Glu Lys Ala Ala
130                 135                 140 aaa gtg atg ggt gac tac acc gat atc gaa att att gaa gca cat cat    480
Lys Val Met Gly Asp Tyr Thr Asp Ile Glu Ile Ile Glu Ala His His
145                 150                 155                 160 aga cat aaa gtt gat gcg ccg tca ggc acc gca ctg gca atg gga gag    528
Arg His Lys Val Asp Ala Pro Ser Gly Thr Ala Leu Ala Met Gly Glu
                165                 170                 175 gcg atc gcc cac gcc ctt gat aaa gat ctg aaa gat tgc gcg gtc tac    576
Ala Ile Ala His Ala Leu Asp Lys Asp Leu Lys Asp Cys Ala Val Tyr
            180                 185                 190 agt cgt gaa ggc cac acc ggt gaa cgt gtg cct ggc acc att ggt ttt    624
Ser Arg Glu Gly His Thr Gly Glu Arg Val Pro Gly Thr Ile Gly Phe
        195                 200                 205 gcc acc gtg cgt gca ggt gac atc gtt ggt gaa cat acc gcg atg ttt    672
Ala Thr Val Arg Ala Gly Asp Ile Val Gly Glu His Thr Ala Met Phe
210                 215                 220 gcc gat att ggc gag cgt ctg gag atc acc cat aag gcg tcc agc cgt    720
Ala Asp Ile Gly Glu Arg Leu Glu Ile Thr His Lys Ala Ser Ser Arg
225                 230                 235                 240 atg aca ttt gct aac ggc gcg gta aga tcg gct ttg tgg ttg agt ggt    768
Met Thr Phe Ala Asn Gly Ala Val Arg Ser Ala Leu Trp Leu Ser Gly
                245                 250                 255 aag gaa agc ggt ctt ttt gat atg cga gat gta ctt gat ctc aat aat    816
Lys Glu Ser Gly Leu Phe Asp Met Arg Asp Val Leu Asp Leu Asn Asn
            260                 265                 270 ttg taa                                                            822
Leu
```

<210> SEQ ID NO 43
<211> LENGTH: 273
<212> TYPE: PRT
<213> ORGANISM: Escherichia coli

<400> SEQUENCE: 43

Met His Asp Ala Asn Ile Arg Val Ala Ile Ala Gly Ala Gly Gly Arg
1               5                   10                  15

Met Gly Arg Gln Leu Ile Gln Ala Ala Leu Ala Leu Glu Gly Val Gln
            20                  25                  30

Leu Gly Ala Ala Leu Glu Arg Glu Gly Ser Ser Leu Leu Gly Ser Asp
        35                  40                  45

Ala Gly Glu Leu Ala Gly Ala Gly Lys Thr Gly Val Thr Val Gln Ser
50                  55                  60

Ser Leu Asp Ala Val Lys Asp Asp Phe Asp Val Phe Ile Asp Phe Thr
65                  70                  75                  80

Arg Pro Glu Gly Thr Leu Asn His Leu Ala Phe Cys Arg Gln His Gly
                85                  90                  95

Lys Gly Met Val Ile Gly Thr Thr Gly Phe Asp Glu Ala Gly Lys Gln
            100                 105                 110

Ala Ile Arg Asp Ala Ala Ala Asp Ile Ala Ile Val Phe Ala Ala Asn
        115                 120                 125

Phe Ser Val Gly Val Asn Val Met Leu Lys Leu Leu Glu Lys Ala Ala
130                 135                 140

Lys Val Met Gly Asp Tyr Thr Asp Ile Glu Ile Glu Ala His His
145                 150                 155                 160

Arg His Lys Val Asp Ala Pro Ser Gly Thr Ala Leu Ala Met Gly Glu
                165                 170                 175

Ala Ile Ala His Ala Leu Asp Lys Asp Leu Lys Asp Cys Ala Val Tyr
            180                 185                 190

Ser Arg Glu Gly His Thr Gly Glu Arg Val Pro Gly Thr Ile Gly Phe
        195                 200                 205

Ala Thr Val Arg Ala Gly Asp Ile Val Gly Glu His Thr Ala Met Phe
210                 215                 220

Ala Asp Ile Gly Glu Arg Leu Glu Ile Thr His Lys Ala Ser Ser Arg
225                 230                 235                 240

Met Thr Phe Ala Asn Gly Ala Val Arg Ser Ala Leu Trp Leu Ser Gly
                245                 250                 255

Lys Glu Ser Gly Leu Phe Asp Met Arg Asp Val Leu Asp Leu Asn Asn
            260                 265                 270

Leu

<210> SEQ ID NO 44
<211> LENGTH: 1104
<212> TYPE: DNA
<213> ORGANISM: Escherichia coli
<220> FEATURE:
<221> NAME/KEY: CDS
<222> LOCATION: (1)..(1104)
<223> OTHER INFORMATION:

<400> SEQUENCE: 44

```
atg aaa aat gtt ggt ttt atc ggc tgg cgc ggt atg gtc ggc tcc gtt      48
Met Lys Asn Val Gly Phe Ile Gly Trp Arg Gly Met Val Gly Ser Val
1               5                   10                  15 ctc atg caa cgc atg gtt gaa gag cgc gac ttc gac gcc att cgc cct      96
Leu Met Gln Arg Met Val Glu Glu Arg Asp Phe Asp Ala Ile Arg Pro
            20                  25                  30 gtc ttc ttt tct act tct cag ctt ggc cag gct gcg ccg tct ttt ggc      144
Val Phe Phe Ser Thr Ser Gln Leu Gly Gln Ala Ala Pro Ser Phe Gly
        35                  40                  45 gga acc act ggc aca ctt cag gat gcc ttt gat ctg gag gcg cta aag      192
Gly Thr Thr Gly Thr Leu Gln Asp Ala Phe Asp Leu Glu Ala Leu Lys
```

```
                                           -continued

Gly Thr Thr Gly Thr Leu Gln Asp Ala Phe Asp Leu Glu Ala Leu Lys
    50                  55                  60 gcc ctc gat atc att gtg acc tgt cag ggc ggc gat tat acc aac gaa     240
Ala Leu Asp Ile Ile Val Thr Cys Gln Gly Gly Asp Tyr Thr Asn Glu
65                  70                  75                  80 atc tat cca aag ctt cgt gaa agc gga tgg caa ggt tac tgg att gac     288
Ile Tyr Pro Lys Leu Arg Glu Ser Gly Trp Gln Gly Tyr Trp Ile Asp
                85                  90                  95 gca gca tcg tct ctg cgc atg aaa gat gac gcc atc atc att ctt gac     336
Ala Ala Ser Ser Leu Arg Met Lys Asp Asp Ala Ile Ile Ile Leu Asp
                100                 105                 110 ccc gtc aat cag gac gtc att acc gac gga tta aat aat ggc atc agg     384
Pro Val Asn Gln Asp Val Ile Thr Asp Gly Leu Asn Asn Gly Ile Arg
            115                 120                 125 act ttt gtt ggc ggt aac tgt acc gta agc ctg atg ttg atg tcg ttg     432
Thr Phe Val Gly Gly Asn Cys Thr Val Ser Leu Met Leu Met Ser Leu
130                 135                 140 ggt ggt tta ttc gcc aat gat ctt gtt gat tgg gtg tcc gtt gca acc     480
Gly Gly Leu Phe Ala Asn Asp Leu Val Asp Trp Val Ser Val Ala Thr
145                 150                 155                 160 tac cag gcc gct tcc ggc ggt ggt gcg cga cat atg cgt gag tta tta     528
Tyr Gln Ala Ala Ser Gly Gly Gly Ala Arg His Met Arg Glu Leu Leu
                165                 170                 175 acc cag atg ggc cat ctg tat ggc cat gtg gca gat gaa ctc gcg acc     576
Thr Gln Met Gly His Leu Tyr Gly His Val Ala Asp Glu Leu Ala Thr
                180                 185                 190 ccg tcc tct gct att ctc gat atc gaa cgc aaa gtc aca acc tta acc     624
Pro Ser Ser Ala Ile Leu Asp Ile Glu Arg Lys Val Thr Thr Leu Thr
                195                 200                 205 cgt agc ggt gag ctg ccg gtg gat aac ttt ggc gtg ccg ctg gcg ggt     672
Arg Ser Gly Glu Leu Pro Val Asp Asn Phe Gly Val Pro Leu Ala Gly
210                 215                 220 agc ctg att ccg tgg atc gac aaa cag ctc gat aac ggt cag agc cgc     720
Ser Leu Ile Pro Trp Ile Asp Lys Gln Leu Asp Asn Gly Gln Ser Arg
225                 230                 235                 240 gaa gag tgg aaa ggg cag gcg gaa acc aac aag atc ctc aac aca tct     768
Glu Glu Trp Lys Gly Gln Ala Glu Thr Asn Lys Ile Leu Asn Thr Ser
                245                 250                 255 tcc gta att ccg gta gat ggt tta tgt gtg cgt gtc ggg gca ttg cgc     816
Ser Val Ile Pro Val Asp Gly Leu Cys Val Arg Val Gly Ala Leu Arg
                260                 265                 270 tgc cac agc cag gca ttc act att aaa ttg aaa aaa gat gtg tct att     864
Cys His Ser Gln Ala Phe Thr Ile Lys Leu Lys Lys Asp Val Ser Ile
                275                 280                 285 ccg acc gtg gaa gaa ctg ctg gct gcg cac aat ccg tgg gcg aaa gtc     912
Pro Thr Val Glu Glu Leu Leu Ala Ala His Asn Pro Trp Ala Lys Val
290                 295                 300 gtt ccg aac gat cgg gaa atc act atg cgt gag cta acc cca gct gcc     960
Val Pro Asn Asp Arg Glu Ile Thr Met Arg Glu Leu Thr Pro Ala Ala
305                 310                 315                 320 gtt acc ggc acg ctg acc acg ccg gta ggc cgc ctg cgt aag ctg aat     1008
Val Thr Gly Thr Leu Thr Thr Pro Val Gly Arg Leu Arg Lys Leu Asn
                325                 330                 335 atg gga cca gag ttc ctg tca gcc ttt acc gtg ggc gac cag ctg ctg     1056
Met Gly Pro Glu Phe Leu Ser Ala Phe Thr Val Gly Asp Gln Leu Leu
                340                 345                 350 tgg ggg gcc gcg gag ccg ctg cgt cgg atg ctt cgt caa ctg gcg taa     1104
Trp Gly Ala Ala Glu Pro Leu Arg Arg Met Leu Arg Gln Leu Ala
                355                 360                 365
```

<210> SEQ ID NO 45
<211> LENGTH: 367
<212> TYPE: PRT
<213> ORGANISM: Escherichia coli

<400> SEQUENCE: 45

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
        355                 360                 365

<210> SEQ ID NO 46
<211> LENGTH: 1350
<212> TYPE: DNA

<213> ORGANISM: Escherichia coli
<220> FEATURE:
<221> NAME/KEY: CDS
<222> LOCATION: (1)..(1350)
<223> OTHER INFORMATION:

<400> SEQUENCE: 46

```
atg tct gaa att gtt gtc tcc aaa ttt ggc ggt acc agc gta gct gat        48
Met Ser Glu Ile Val Val Ser Lys Phe Gly Gly Thr Ser Val Ala Asp
1               5                   10                  15 ttt gac gcc atg aac cgc agc gct gat att gtg ctt tct gat gcc aac        96
Phe Asp Ala Met Asn Arg Ser Ala Asp Ile Val Leu Ser Asp Ala Asn
            20                  25                  30 gtg cgt tta gtt gtc ctc tcg gct tct gct ggt atc act aat ctg ctg       144
Val Arg Leu Val Val Leu Ser Ala Ser Ala Gly Ile Thr Asn Leu Leu
        35                  40                  45 gtc gct tta gct gaa gga ctg gaa cct ggc gag cga ttc gaa aaa ctc       192
Val Ala Leu Ala Glu Gly Leu Glu Pro Gly Glu Arg Phe Glu Lys Leu
    50                  55                  60 gac gct atc cgc aac atc cag ttt gcc att ctg gaa cgt ctg cgt tac       240
Asp Ala Ile Arg Asn Ile Gln Phe Ala Ile Leu Glu Arg Leu Arg Tyr
65                  70                  75                  80 ccg aac gtt atc cgt gaa gag att gaa cgt ctg ctg gag aac att act       288
Pro Asn Val Ile Arg Glu Glu Ile Glu Arg Leu Leu Glu Asn Ile Thr
                85                  90                  95 gtt ctg gca gaa gcg gcg gcg ctg gca acg tct ccg gcg ctg aca gat       336
Val Leu Ala Glu Ala Ala Ala Leu Ala Thr Ser Pro Ala Leu Thr Asp
            100                 105                 110 gag ctg gtc agc cac ggc gag ctg atg tcg acc ctg ctg ttt gtt gag       384
Glu Leu Val Ser His Gly Glu Leu Met Ser Thr Leu Leu Phe Val Glu
        115                 120                 125 atc ctg cgc gaa cgc gat gtt cag gca cag tgg ttt gat gta cgt aaa       432
Ile Leu Arg Glu Arg Asp Val Gln Ala Gln Trp Phe Asp Val Arg Lys
    130                 135                 140 gtg atg cgt acc aac gac cga ttt ggt cgt gca gag cca gat ata gcc       480
Val Met Arg Thr Asn Asp Arg Phe Gly Arg Ala Glu Pro Asp Ile Ala
145                 150                 155                 160 gcg ctg gcg gaa ctg gcc gcg ctg cag ctg ctc cca cgt ctc aat gaa       528
Ala Leu Ala Glu Leu Ala Ala Leu Gln Leu Leu Pro Arg Leu Asn Glu
                165                 170                 175 ggc tta gtg atc acc cag gga ttt atc ggt agc gaa aat aaa ggt cgt       576
Gly Leu Val Ile Thr Gln Gly Phe Ile Gly Ser Glu Asn Lys Gly Arg
            180                 185                 190 aca acg acg ctt ggc cgt gga ggc agc gat tat acg gca gcc ttg ctg       624
Thr Thr Thr Leu Gly Arg Gly Gly Ser Asp Tyr Thr Ala Ala Leu Leu
        195                 200                 205 gcg gag gct tta cac gca tct cgt gtt gat atc tgg acc gac gtc ccg       672
Ala Glu Ala Leu His Ala Ser Arg Val Asp Ile Trp Thr Asp Val Pro
    210                 215                 220 ggc atc tac acc acc gat cca cgc gta gtt tcc gca gca aaa cgc att       720
Gly Ile Tyr Thr Thr Asp Pro Arg Val Val Ser Ala Ala Lys Arg Ile
225                 230                 235                 240 gat gaa atc gcg ttt gcc gaa gcg gca gag atg gca act ttt ggt gca       768
Asp Glu Ile Ala Phe Ala Glu Ala Ala Glu Met Ala Thr Phe Gly Ala
                245                 250                 255 aaa gta ctg cat ccg gca acg ttg cta ccc gca gta cgc agc gat atc       816
Lys Val Leu His Pro Ala Thr Leu Leu Pro Ala Val Arg Ser Asp Ile
            260                 265                 270 ccg gtc ttt gtc ggc tcc agc aaa gac cca cgc gca ggt ggt acg ctg       864
Pro Val Phe Val Gly Ser Ser Lys Asp Pro Arg Ala Gly Gly Thr Leu
        275                 280                 285
```

```
gtg tgc aat aaa act gaa aat ccg ccg ctg ttc cgc gct ctg gcg ctt      912
Val Cys Asn Lys Thr Glu Asn Pro Pro Leu Phe Arg Ala Leu Ala Leu
    290                 295                 300 cgt cgc aat cag act ctg ctc act ttg cac agc ctg aat atg ctg cat      960
Arg Arg Asn Gln Thr Leu Leu Thr Leu His Ser Leu Asn Met Leu His
305                 310                 315                 320 tct cgc ggt ttc ctc gcg gaa gtt ttc ggc atc ctc gcg cgg cat aat     1008
Ser Arg Gly Phe Leu Ala Glu Val Phe Gly Ile Leu Ala Arg His Asn
                325                 330                 335 att tcg gta gac tta atc acc acg tca gaa gtg agc gtg gca tta acc     1056
Ile Ser Val Asp Leu Ile Thr Thr Ser Glu Val Ser Val Ala Leu Thr
            340                 345                 350 ctt gat acc acc ggt tca acc tcc act ggc gat acg ttg ctg acg caa     1104
Leu Asp Thr Thr Gly Ser Thr Ser Thr Gly Asp Thr Leu Leu Thr Gln
        355                 360                 365 tct ctg ctg atg gag ctt tcc gca ctg tgt cgg gtg gag gtg gaa gaa     1152
Ser Leu Leu Met Glu Leu Ser Ala Leu Cys Arg Val Glu Val Glu Glu
    370                 375                 380 ggt ctg gcg ctg gtc gcg ttg att ggc aat gac ctg tca aaa gcc tgc     1200
Gly Leu Ala Leu Val Ala Leu Ile Gly Asn Asp Leu Ser Lys Ala Cys
385                 390                 395                 400 ggc gtt ggc aaa gag gta ttc ggc gta ctg gaa ccg ttc aac att cgc     1248
Gly Val Gly Lys Glu Val Phe Gly Val Leu Glu Pro Phe Asn Ile Arg
                405                 410                 415 atg att tgt tat ggc gca tcc agc cat aac ctg tgc ttc ctg gtg ccc     1296
Met Ile Cys Tyr Gly Ala Ser Ser His Asn Leu Cys Phe Leu Val Pro
            420                 425                 430 ggc gaa gat gcc gag cag gtg gtg caa aaa ctg cat agt aat ttg ttt     1344
Gly Glu Asp Ala Glu Gln Val Val Gln Lys Leu His Ser Asn Leu Phe
        435                 440                 445 gag taa                                                              1350
Glu

<210> SEQ ID NO 47
<211> LENGTH: 449
<212> TYPE: PRT
<213> ORGANISM: Escherichia coli

<400> SEQUENCE: 47

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
    130                 135                 140

Val Met Arg Thr Asn Asp Arg Phe Gly Arg Ala Glu Pro Asp Ile Ala
145                 150                 155                 160
```

Ala Leu Ala Glu Leu Ala Ala Leu Gln Leu Leu Pro Arg Leu Asn Glu
            165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
            195                 200                 205

Ala Glu Ala Leu His Ala Ser Arg Val Asp Ile Trp Thr Asp Val Pro
210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
            370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
            435                 440                 445

Glu

<210> SEQ ID NO 48
<211> LENGTH: 1245
<212> TYPE: DNA
<213> ORGANISM: Methylophilus methylotrophus
<220> FEATURE:
<221> NAME/KEY: CDS
<222> LOCATION: (1)..(1245)
<223> OTHER INFORMATION:

<400> SEQUENCE: 48

| gtg acc gct ttt tca atc caa caa ggc cta cta cat gcc gag aat gta | 48 |
|---|---|
| Val Thr Ala Phe Ser Ile Gln Gln Gly Leu Leu His Ala Glu Asn Val | |
| 1               5                   10                  15 | |

| gcc ctg cgt gac att gca caa acg cat caa acg ccc act tac gtc tat | 96 |
|---|---|
| Ala Leu Arg Asp Ile Ala Gln Thr His Gln Thr Pro Thr Tyr Val Tyr | |
|             20                  25                  30 | |

| tca cgt gcc gcc ttg acg act gct ttc gag cgt ttt cag gca ggc ctg | 144 |
|---|---|
| Ser Arg Ala Ala Leu Thr Thr Ala Phe Glu Arg Phe Gln Ala Gly Leu | |
|         35                  40                  45 | |

| | |
|---|---|
| act gga cat gac cat ttg atc tgc ttt gct gtc aaa gcc aac cca agc<br>Thr Gly His Asp His Leu Ile Cys Phe Ala Val Lys Ala Asn Pro Ser<br>50                           55                        60 | 192 |
| ctg gcc att ctc aac ctg ttt gcg cga atg gga gcg ggc ttt gat att<br>Leu Ala Ile Leu Asn Leu Phe Ala Arg Met Gly Ala Gly Phe Asp Ile<br>65                       70                      75                      80 | 240 |
| gtg tcc ggt ggt gag ctg gca cgc gtc ttg gcc gca ggt ggc gac ccg<br>Val Ser Gly Gly Glu Leu Ala Arg Val Leu Ala Ala Gly Gly Asp Pro<br>              85                      90                      95 | 288 |
| aaa aaa gtg gtg ttt tct ggt gtg ggc aaa tcc cat gcg gaa atc aaa<br>Lys Lys Val Val Phe Ser Gly Val Gly Lys Ser His Ala Glu Ile Lys<br>          100                      105                  110 | 336 |
| gcc gcg ctt gaa gcg ggc att ctt tgc ttc aac gtg gaa tca gtg aat<br>Ala Ala Leu Glu Ala Gly Ile Leu Cys Phe Asn Val Glu Ser Val Asn<br>115                     120                      125 | 384 |
| gag cta gac cgc atc cag cag gtg gcg gcc agc ctg ggc aaa aaa gcg<br>Glu Leu Asp Arg Ile Gln Gln Val Ala Ala Ser Leu Gly Lys Lys Ala<br>130                     135                      140 | 432 |
| cct att tcc ctg cgc gtg aac ccc aat gtg gat gcc aaa acc cat ccc<br>Pro Ile Ser Leu Arg Val Asn Pro Asn Val Asp Ala Lys Thr His Pro<br>145                   150                      155                      160 | 480 |
| tat att tcc acc ggc ctc aaa aac aat aaa ttt ggt gtg gca ttt gaa<br>Tyr Ile Ser Thr Gly Leu Lys Asn Asn Lys Phe Gly Val Ala Phe Glu<br>                    165                      170                  175 | 528 |
| gat gcc ttg ggc ctc tat gaa aaa gcg gcg caa ctg cca aac atc gag<br>Asp Ala Leu Gly Leu Tyr Glu Lys Ala Ala Gln Leu Pro Asn Ile Glu<br>                    180                      185                  190 | 576 |
| gta cac ggc gta gat tgc cat atc ggc tcg caa atc act gag ctg tca<br>Val His Gly Val Asp Cys His Ile Gly Ser Gln Ile Thr Glu Leu Ser<br>                       195                      200                  205 | 624 |
| cct ttc ctc gat gcc ttg gat aaa gta ttg ggc ctg gta gat gca ttg<br>Pro Phe Leu Asp Ala Leu Asp Lys Val Leu Gly Leu Val Asp Ala Leu<br>210                     215                      220 | 672 |
| gcc gcc aaa ggc att cat atc cag cat ata gac gtt ggc ggc ggt gtc<br>Ala Ala Lys Gly Ile His Ile Gln His Ile Asp Val Gly Gly Gly Val<br>225                   230                      235                      240 | 720 |
| ggt att act tac agc gac gaa acg cca cca gac ttt gca gcc tac act<br>Gly Ile Thr Tyr Ser Asp Glu Thr Pro Pro Asp Phe Ala Ala Tyr Thr<br>                    245                      250                  255 | 768 |
| gca gcg att ctt aaa aag ctg gca ggc agg aat gta aaa gtg ttg ttt<br>Ala Ala Ile Leu Lys Lys Leu Ala Gly Arg Asn Val Lys Val Leu Phe<br>260                     265                      270 | 816 |
| gag ccc ggc cgt gcc ctg gtg ggt aac gcc ggt gtg ctg ctg acc aag<br>Glu Pro Gly Arg Ala Leu Val Gly Asn Ala Gly Val Leu Leu Thr Lys<br>          275                      280                  285 | 864 |
| gtc gaa tac ctg aaa cct ggc gaa acc aaa aac ttt gcg att gtc gat<br>Val Glu Tyr Leu Lys Pro Gly Glu Thr Lys Asn Phe Ala Ile Val Asp<br>290                     295                      300 | 912 |
| gcc gcc atg aac gac ctc atg cgc ccg gct ttg tat gat gct ttc cac<br>Ala Ala Met Asn Asp Leu Met Arg Pro Ala Leu Tyr Asp Ala Phe His<br>305                     310                      315                      320 | 960 |
| aac att acg acc att gcc act tct gca gcc ccc gca caa atc tat gag<br>Asn Ile Thr Thr Ile Ala Thr Ser Ala Ala Pro Ala Gln Ile Tyr Glu<br>                    325                      330                  335 | 1008 |
| atc gtt ggc ccg gtt tgc gag agt ggt gac ttt tta ggc cat gac cgt<br>Ile Val Gly Pro Val Cys Glu Ser Gly Asp Phe Leu Gly His Asp Arg<br>                       340                      345                  350 | 1056 |
| aca ctt gcg atc gaa gaa ggt gat tac ctg gcg att cac tcc gca ggc<br>Thr Leu Ala Ile Glu Glu Gly Asp Tyr Leu Ala Ile His Ser Ala Gly<br>355                     360                      365 | 1104 |

```
gct tat ggc atg agc atg gcc agc aac tac aac acg cgc gcc cgt gcc      1152
Ala Tyr Gly Met Ser Met Ala Ser Asn Tyr Asn Thr Arg Ala Arg Ala
370             375                 380 gca gag gta ttg gtt gat ggt gac cag gtg cat gtg atc cgt gaa cgt      1200
Ala Glu Val Leu Val Asp Gly Asp Gln Val His Val Ile Arg Glu Arg
385             390                 395                 400 gaa caa att gcc gac ctg ttt aaa ctg gag cgt acg ctg cca taa          1245
Glu Gln Ile Ala Asp Leu Phe Lys Leu Glu Arg Thr Leu Pro
            405                 410
```

<210> SEQ ID NO 49
<211> LENGTH: 414
<212> TYPE: PRT
<213> ORGANISM: Methylophilus methylotrophus

<400> SEQUENCE: 49

```
Val Thr Ala Phe Ser Ile Gln Gln Gly Leu Leu His Ala Glu Asn Val
1               5                   10                  15

Ala Leu Arg Asp Ile Ala Gln Thr His Gln Thr Pro Thr Tyr Val Tyr
                20                  25                  30

Ser Arg Ala Ala Leu Thr Thr Ala Phe Glu Arg Phe Gln Ala Gly Leu
            35                  40                  45

Thr Gly His Asp His Leu Ile Cys Phe Ala Val Lys Ala Asn Pro Ser
        50                  55                  60

Leu Ala Ile Leu Asn Leu Phe Ala Arg Met Gly Ala Gly Phe Asp Ile
65                  70                  75                  80

Val Ser Gly Gly Glu Leu Ala Arg Val Leu Ala Ala Gly Gly Asp Pro
                85                  90                  95

Lys Lys Val Val Phe Ser Gly Val Gly Lys Ser His Ala Glu Ile Lys
            100                 105                 110

Ala Ala Leu Glu Ala Gly Ile Leu Cys Phe Asn Val Glu Ser Val Asn
        115                 120                 125

Glu Leu Asp Arg Ile Gln Gln Val Ala Ala Ser Leu Gly Lys Lys Ala
    130                 135                 140

Pro Ile Ser Leu Arg Val Asn Pro Asn Val Asp Ala Lys Thr His Pro
145                 150                 155                 160

Tyr Ile Ser Thr Gly Leu Lys Asn Asn Lys Phe Gly Val Ala Phe Glu
                165                 170                 175

Asp Ala Leu Gly Leu Tyr Glu Lys Ala Ala Gln Leu Pro Asn Ile Glu
            180                 185                 190

Val His Gly Val Asp Cys His Ile Gly Ser Gln Ile Thr Glu Leu Ser
        195                 200                 205

Pro Phe Leu Asp Ala Leu Asp Lys Val Leu Gly Leu Val Asp Ala Leu
    210                 215                 220

Ala Ala Lys Gly Ile His Ile Gln His Ile Asp Val Gly Gly Gly Val
225                 230                 235                 240

Gly Ile Thr Tyr Ser Asp Glu Thr Pro Pro Asp Phe Ala Ala Tyr Thr
                245                 250                 255

Ala Ala Ile Leu Lys Lys Leu Ala Gly Arg Asn Val Lys Val Leu Phe
            260                 265                 270

Glu Pro Gly Arg Ala Leu Val Gly Asn Ala Gly Val Leu Leu Thr Lys
        275                 280                 285

Val Glu Tyr Leu Lys Pro Gly Glu Thr Lys Asn Phe Ala Ile Val Asp
    290                 295                 300

Ala Ala Met Asn Asp Leu Met Arg Pro Ala Leu Tyr Asp Ala Phe His
305                 310                 315                 320
```

```
Asn Ile Thr Thr Ile Ala Thr Ser Ala Ala Pro Ala Gln Ile Tyr Glu
            325                 330                 335

Ile Val Gly Pro Val Cys Glu Ser Gly Asp Phe Leu Gly His Asp Arg
            340                 345                 350

Thr Leu Ala Ile Glu Glu Gly Asp Tyr Leu Ala Ile His Ser Ala Gly
            355                 360                 365

Ala Tyr Gly Met Ser Met Ala Ser Asn Tyr Asn Thr Arg Ala Arg Ala
            370                 375                 380

Ala Glu Val Leu Val Asp Gly Asp Gln Val His Val Ile Arg Glu Arg
385                 390                 395                 400

Glu Gln Ile Ala Asp Leu Phe Lys Leu Glu Arg Thr Leu Pro
            405                 410

<210> SEQ ID NO 50
<211> LENGTH: 712
<212> TYPE: DNA
<213> ORGANISM: Brevibacterium lactofermentum
<220> FEATURE:
<221> NAME/KEY: CDS
<222> LOCATION: (1)..(375)
<223> OTHER INFORMATION:

<400> SEQUENCE: 50 atg gtg atc atg gaa atc ttc att aca ggt ctg ctt ttg ggg gcc agt        48
Met Val Ile Met Glu Ile Phe Ile Thr Gly Leu Leu Leu Gly Ala Ser
1               5                   10                  15 ctt ttg ctg tcc atc gga ccg cag aat gta ctg gtg att aaa caa gga        96
Leu Leu Leu Ser Ile Gly Pro Gln Asn Val Leu Val Ile Lys Gln Gly
                20                  25                  30 att aag cgc gaa gga ctc att gcg gtt ctt ctc gtg tgt tta att tct      144
Ile Lys Arg Glu Gly Leu Ile Ala Val Leu Leu Val Cys Leu Ile Ser
            35                  40                  45 gac gtc ttt ttg ttc atc gcc ggc acc ttg ggc gtt gat ctt ttg tcc      192
Asp Val Phe Leu Phe Ile Ala Gly Thr Leu Gly Val Asp Leu Leu Ser
        50                  55                  60 aat gcc gcg ccg atc gtg ctc gat att atg cgc tgg ggt ggc atc gct      240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac      288
Tyr Leu Leu Trp Phe Ala Val Met Ala Ala Lys Asp Ala Met Thr Asn
                85                  90                  95 aag gtg gaa gcg cca cag atc att gaa gaa aca gaa cca acc gtg ccc      336
Lys Val Glu Ala Pro Gln Ile Ile Glu Glu Thr Glu Pro Thr Val Pro
                100                 105                 110 gat gac acg cct ttg ggc gtg ttc ggc ggt ggc cac tga cacgcgcaac       385
Asp Asp Thr Pro Leu Gly Val Phe Gly Gly Gly His
            115                 120 cgggtgcggg tggaggtgag cgtcgataag cagcgggttt gggtgaagcc catgttgatg    445
gcaatcgtgc tgacctggtt gaacccgaat gcgtatttgg acgcgtttgt gtttatcggc    505
ggcgtcggcg cgcaatacgg cgacaccgga cggtggattt cgccgctggc gcgttcgcg    565 gcaagcctga tctggttccc gctggtgggt ttcggcgcag cagcattgtc acgcccgctg    625
tccagcccca aggtgtggcg ctggatcaac gtcgtcgtgg cagttgtgat gaccgcattg    685
gccatcaaac tgatgttgat gggttag                                        712

<210> SEQ ID NO 51
<211> LENGTH: 124
<212> TYPE: PRT
<213> ORGANISM: Brevibacterium lactofermentum
```

<400> SEQUENCE: 51

```
Met Val Ile Met Glu Ile Phe Ile Thr Gly Leu Leu Gly Ala Ser
1               5                   10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Val Phe Gly Gly Gly His
            115                 120
```

<210> SEQ ID NO 52
<211> LENGTH: 963
<212> TYPE: DNA
<213> ORGANISM: Brevibacterium lactofermentum
<220> FEATURE:
<221> NAME/KEY: CDS
<222> LOCATION: (1)..(963)
<223> OTHER INFORMATION:

<400> SEQUENCE: 52

```
atg acc aac atc cgc gta gct atc gtg ggc tac gga aac ctg gga cgc         48
Met Thr Asn Ile Arg Val Ala Ile Val Gly Tyr Gly Asn Leu Gly Arg
1               5                   10                  15 agc gtc gaa aag ctt att gcc aag cag ccc gac atg gac ctt gta gga         96
Ser Val Glu Lys Leu Ile Ala Lys Gln Pro Asp Met Asp Leu Val Gly
            20                  25                  30 atc ttc tcg cgc cgg gcc acc ctc gac aca aag acg cca gtc ttt gat        144
Ile Phe Ser Arg Arg Ala Thr Leu Asp Thr Lys Thr Pro Val Phe Asp
        35                  40                  45 gtc gcc gac gtg gac aag cac gcc gac gac gtg gac gtg ctg ttc ctg        192
Val Ala Asp Val Asp Lys His Ala Asp Asp Val Asp Val Leu Phe Leu
    50                  55                  60 tgc atg ggc tcc gcc acc gac atc cct gag cag gca cca aag ttc gcg        240
Cys Met Gly Ser Ala Thr Asp Ile Pro Glu Gln Ala Pro Lys Phe Ala
65                  70                  75                  80 cag ttc gcc tgc acc gta gac acc tac gac aac cac cgc gac atc cca        288
Gln Phe Ala Cys Thr Val Asp Thr Tyr Asp Asn His Arg Asp Ile Pro
                85                  90                  95 cgc cac cgc cag gtc atg aac gaa gcc gcc acc gca gcc ggc aac gtt        336
Arg His Arg Gln Val Met Asn Glu Ala Ala Thr Ala Ala Gly Asn Val
            100                 105                 110 gca ctg gtc tct acc ggc tgg gat cca gga atg ttc tcc atc aac cgc        384
Ala Leu Val Ser Thr Gly Trp Asp Pro Gly Met Phe Ser Ile Asn Arg
        115                 120                 125 gtc tac gca gcg gca gtc tta gcc gag cac cag cag cac acc ttc tgg        432
Val Tyr Ala Ala Ala Val Leu Ala Glu His Gln Gln His Thr Phe Trp
    130                 135                 140 ggc cca ggt ttg tca cag ggc cac tcc gat gct ttg cga cgc atc cct        480
Gly Pro Gly Leu Ser Gln Gly His Ser Asp Ala Leu Arg Arg Ile Pro
145                 150                 155                 160 ggc gtt caa aag gca gtc cag tac acc ctc cca tcc gaa gac gcc ctg        528
```

```
                                                                          -continued Gly Val Gln Lys Ala Val Gln Tyr Thr Leu Pro Ser Glu Asp Ala Leu
                165                 170                 175 gaa aag gcc cgc cgg ggc gaa gcc ggc gac ctt acc gga aag caa acc       576
Glu Lys Ala Arg Arg Gly Glu Ala Gly Asp Leu Thr Gly Lys Gln Thr
            180                 185                 190 cac aag cgc caa tgc ttc gtg gtt gcc gac gcg gcc gat cac gag cgc       624
His Lys Arg Gln Cys Phe Val Val Ala Asp Ala Ala Asp His Glu Arg
        195                 200                 205 atc gaa aac gac atc cgc acc atg cct gat tac ttc gtt ggc tac gaa       672
Ile Glu Asn Asp Ile Arg Thr Met Pro Asp Tyr Phe Val Gly Tyr Glu
    210                 215                 220 gtc gaa gtc aac ttc atc gac gaa gca acc ttc gac tcc gag cac acc       720
Val Glu Val Asn Phe Ile Asp Glu Ala Thr Phe Asp Ser Glu His Thr
225                 230                 235                 240 ggc atg cca cac ggt ggc cac gtg att acc acc ggc gac acc ggt ggc       768
Gly Met Pro His Gly Gly His Val Ile Thr Thr Gly Asp Thr Gly Gly
                245                 250                 255 ttc aac cac acc gtg gaa tac atc ctc aag ctg gac cga aac cca gat       816
Phe Asn His Thr Val Glu Tyr Ile Leu Lys Leu Asp Arg Asn Pro Asp
            260                 265                 270 ttc acc gct tcc tca cag atc gct ttc ggt cgc gca gct cac cgc atg       864
Phe Thr Ala Ser Ser Gln Ile Ala Phe Gly Arg Ala Ala His Arg Met
        275                 280                 285 aag cag cag ggc caa agc gga gct ttc acc gtc ctc gaa gtt gct cca       912
Lys Gln Gln Gly Gln Ser Gly Ala Phe Thr Val Leu Glu Val Ala Pro
    290                 295                 300 tac ctg ctc tcc cca gag aac ttg gac gat ctg atc gca cgc gac gtc       960
Tyr Leu Leu Ser Pro Glu Asn Leu Asp Asp Leu Ile Ala Arg Asp Val
305                 310                 315                 320 taa                                                                     963

<210> SEQ ID NO 53
<211> LENGTH: 320
<212> TYPE: PRT
<213> ORGANISM: Brevibacterium lactofermentum

<400> SEQUENCE: 53

Met Thr Asn Ile Arg Val Ala Ile Val Gly Tyr Gly Asn Leu Gly Arg
1               5                   10                  15

Ser Val Glu Lys Leu Ile Ala Lys Gln Pro Asp Met Asp Leu Val Gly
            20                  25                  30

Ile Phe Ser Arg Arg Ala Thr Leu Asp Thr Lys Thr Pro Val Phe Asp
        35                  40                  45

Val Ala Asp Val Asp Lys His Ala Asp Asp Val Asp Val Leu Phe Leu
    50                  55                  60

Cys Met Gly Ser Ala Thr Asp Ile Pro Glu Gln Ala Pro Lys Phe Ala
65                  70                  75                  80

Gln Phe Ala Cys Thr Val Asp Thr Tyr Asp Asn His Arg Asp Ile Pro
                85                  90                  95

Arg His Arg Gln Val Met Asn Glu Ala Ala Thr Ala Ala Gly Asn Val
            100                 105                 110

Ala Leu Val Ser Thr Gly Trp Asp Pro Gly Met Phe Ser Ile Asn Arg
        115                 120                 125

Val Tyr Ala Ala Ala Val Leu Ala Glu His Gln His Thr Phe Trp
    130                 135                 140

Gly Pro Gly Leu Ser Gln Gly His Ser Asp Ala Leu Arg Arg Ile Pro
145                 150                 155                 160

Gly Val Gln Lys Ala Val Gln Tyr Thr Leu Pro Ser Glu Asp Ala Leu
```

```
                    165                 170                 175
Glu Lys Ala Arg Arg Gly Glu Ala Gly Asp Leu Thr Gly Lys Gln Thr
            180                 185                 190

His Lys Arg Gln Cys Phe Val Ala Asp Ala Ala Asp His Glu Arg
        195                 200                 205

Ile Glu Asn Asp Ile Arg Thr Met Pro Asp Tyr Phe Val Gly Tyr Glu
    210                 215                 220

Val Glu Val Asn Phe Ile Asp Glu Ala Thr Phe Asp Ser Glu His Thr
225                 230                 235                 240

Gly Met Pro His Gly Gly His Val Ile Thr Thr Gly Asp Thr Gly Gly
                245                 250                 255

Phe Asn His Thr Val Glu Tyr Ile Leu Lys Leu Asp Arg Asn Pro Asp
            260                 265                 270

Phe Thr Ala Ser Ser Gln Ile Ala Phe Gly Arg Ala Ala His Arg Met
        275                 280                 285

Lys Gln Gln Gly Gln Ser Gly Ala Phe Thr Val Leu Glu Val Ala Pro
    290                 295                 300

Tyr Leu Leu Ser Pro Glu Asn Leu Asp Asp Leu Ile Ala Arg Asp Val
305                 310                 315                 320

<210> SEQ ID NO 54
<211> LENGTH: 711
<212> TYPE: DNA
<213> ORGANISM: Brevibacterium lactofermentum
<220> FEATURE:
<221> NAME/KEY: CDS
<222> LOCATION: (1)..(711)

<400> SEQUENCE: 54 atg gtg atc atg gaa atc ttc att aca ggt ctg ctt ttg ggg gcc agt       48
Met Val Ile Met Glu Ile Phe Ile Thr Gly Leu Leu Leu Gly Ala Ser
1               5                   10                  15 ctt tta ctg tcc atc gga ccg cag aat gta ctg gtg att aaa caa gga       96
Leu Leu Leu Ser Ile Gly Pro Gln Asn Val Leu Val Ile Lys Gln Gly
                20                  25                  30 att aag cgc gaa gga ctc att gcg gtt ctt ctc gtg tgt tta att tct      144
Ile Lys Arg Glu Gly Leu Ile Ala Val Leu Leu Val Cys Leu Ile Ser
            35                  40                  45 gac gtc ttt ttg ttc atc gcc ggc acc ttg ggc gtt gat ctt ttg tcc      192
Asp Val Phe Leu Phe Ile Ala Gly Thr Leu Gly Val Asp Leu Leu Ser
        50                  55                  60 aat gcc gcg ccg atc gtg ctc gat att atg cgc tgg ggt ggc atc gct      240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac      288
Tyr Leu Leu Trp Phe Ala Val Met Ala Ala Lys Asp Ala Met Thr Asn
                85                  90                  95 aag gtg gaa gcg cca cag atc att gaa gaa aca gaa cca acc gtg ccc      336
Lys Val Glu Ala Pro Gln Ile Ile Glu Glu Thr Glu Pro Thr Val Pro
            100                 105                 110 gat gac acg cct ttg ggc ggt tcg gcg gtg gcc act gac acg cgc aac      384
Asp Asp Thr Pro Leu Gly Gly Ser Ala Val Ala Thr Asp Thr Arg Asn
        115                 120                 125 cgg gtg cgg gtg gag gtg agc gtc gat aag cag cgg gtt tgg gta aag      432
Arg Val Arg Val Glu Val Ser Val Asp Lys Gln Arg Val Trp Val Lys
    130                 135                 140 ccc atg ttg atg gca atc gtg ctg acc tgg ttg aac ccg aat gcg tat      480
Pro Met Leu Met Ala Ile Val Leu Thr Trp Leu Asn Pro Asn Ala Tyr
145                 150                 155                 160
```

```
ttg gac gcg ttt gtg ttt atc ggc ggc gtc ggc gcg caa tac ggc gac    528
Leu Asp Ala Phe Val Phe Ile Gly Gly Val Gly Ala Gln Tyr Gly Asp
                165                 170                 175 acc gga cgg tgg att ttc gcc gct ggc gcg ttc gcg gca agc ctg atc    576
Thr Gly Arg Trp Ile Phe Ala Ala Gly Ala Phe Ala Ala Ser Leu Ile
            180                 185                 190 tgg ttc ccg ctg gtg ggt ttc ggc gca gca gca ttg tca cgc ccg ctg    624
Trp Phe Pro Leu Val Gly Phe Gly Ala Ala Ala Leu Ser Arg Pro Leu
        195                 200                 205 tcc agc ccc aag gtg tgg cgc tgg atc aac gtc gtc gtg gca gtt gtg    672
Ser Ser Pro Lys Val Trp Arg Trp Ile Asn Val Val Val Ala Val Val
    210                 215                 220 atg acc gca ttg gcc atc aaa ctg atg ttg atg ggt tag                711
Met Thr Ala Leu Ala Ile Lys Leu Met Leu Met Gly
225                 230                 235

<210> SEQ ID NO 55
<211> LENGTH: 236
<212> TYPE: PRT
<213> ORGANISM: Brevibacterium lactofermentum

<400> SEQUENCE: 55

Met Val Ile Met Glu Ile Phe Ile Thr Gly Leu Leu Leu Gly Ala Ser
1               5                   10                  15

Leu Leu Leu Ser Ile Gly Pro Gln Asn Val Leu Val Ile Lys Gln Gly
            20                  25                  30

Ile Lys Arg Glu Gly Leu Ile Ala Val Leu Leu Val Cys Leu Ile Ser
        35                  40                  45

Asp Val Phe Leu Phe Ile Ala Gly Thr Leu Gly Val Asp Leu Leu Ser
    50                  55                  60

Asn Ala Ala Pro Ile Val Leu Asp Ile Met Arg Trp Gly Gly Ile Ala
65                  70                  75                  80

Tyr Leu Leu Trp Phe Ala Val Met Ala Ala Lys Asp Ala Met Thr Asn
                85                  90                  95

Lys Val Glu Ala Pro Gln Ile Ile Glu Glu Thr Glu Pro Thr Val Pro
            100                 105                 110

Asp Asp Thr Pro Leu Gly Gly Ser Ala Val Ala Thr Asp Thr Arg Asn
        115                 120                 125

Arg Val Arg Val Glu Val Ser Val Asp Lys Gln Arg Val Trp Val Lys
    130                 135                 140

Pro Met Leu Met Ala Ile Val Leu Thr Trp Leu Asn Pro Asn Ala Tyr
145                 150                 155                 160

Leu Asp Ala Phe Val Phe Ile Gly Gly Val Gly Ala Gln Tyr Gly Asp
                165                 170                 175

Thr Gly Arg Trp Ile Phe Ala Ala Gly Ala Phe Ala Ala Ser Leu Ile
            180                 185                 190

Trp Phe Pro Leu Val Gly Phe Gly Ala Ala Ala Leu Ser Arg Pro Leu
        195                 200                 205

Ser Ser Pro Lys Val Trp Arg Trp Ile Asn Val Val Val Ala Val Val
    210                 215                 220

Met Thr Ala Leu Ala Ile Lys Leu Met Leu Met Gly
225                 230                 235

<210> SEQ ID NO 56
<211> LENGTH: 761
<212> TYPE: DNA
<213> ORGANISM: Brevibacterium lactofermentum
<220> FEATURE:
<221> NAME/KEY: CDS
```

```
<222> LOCATION: (1)..(372)
<223> OTHER INFORMATION:
<220> FEATURE:
<221> NAME/KEY: CDS
<222> LOCATION: (401)..(712)
<223> OTHER INFORMATION:

<400> SEQUENCE: 56 atg gtg atc atg gaa atc ttc att aca ggt ctg ctt ttg ggg gcc agt        48
Met Val Ile Met Glu Ile Phe Ile Thr Gly Leu Leu Leu Gly Ala Ser
1               5                   10                  15 ctt ttg ctg tcc atc gga ccg cag aat gta ctg gtg att aaa caa gga        96
Leu Leu Leu Ser Ile Gly Pro Gln Asn Val Leu Val Ile Lys Gln Gly
                20                  25                  30 att aag cgc gaa gga ctc att gcg gtt ctt ctc gtg tgt tta att tct      144
Ile Lys Arg Glu Gly Leu Ile Ala Val Leu Leu Val Cys Leu Ile Ser
            35                  40                  45 gac gtc ttt ttg ttc atc gcc ggc acc ttg ggc gtt gat ctt ttg tcc      192
Asp Val Phe Leu Phe Ile Ala Gly Thr Leu Gly Val Asp Leu Leu Ser
        50                  55                  60 aat gcc gcg ccg atc gtg ctc gat att atg cgc tgg ggt ggc atc gct      240
Asn Ala Ala Pro Ile Val Leu Asp Ile Met Arg Trp Gly Gly Ile Ala
65                  70                  75                  80 tac ctg tta tgg ttt gcc gtc atg gca gcg aaa gac gcc atg aca aac      288
Tyr Leu Leu Trp Phe Ala Val Met Ala Ala Lys Asp Ala Met Thr Asn
                85                  90                  95 aag gtg gaa gcg cca cag atc att gaa gaa aca gaa cca acc gtg ccc      336
Lys Val Glu Ala Pro Gln Ile Ile Glu Glu Thr Glu Pro Thr Val Pro
            100                 105                 110 gat gac acg cct ttg ggc gtg ttc ggc ggt ggc cac tgactagcta            382
Asp Asp Thr Pro Leu Gly Val Phe Gly Gly Gly His
        115                 120 aaccgggtgc gggtggag gtg agc gtc gat aag cag cgg gtt tgg gtg aag      433
                    Val Ser Val Asp Lys Gln Arg Val Trp Val Lys
                        125                 130                 135 ccc atg ttg atg gca atc gtg ctg acc tgg ttg aac ccg aat gcg tat      481
Pro Met Leu Met Ala Ile Val Leu Thr Trp Leu Asn Pro Asn Ala Tyr
                140                 145                 150 ttg gac gcg ttt gtg ttt atc ggc ggc gtc ggc gcg caa tac ggc gac      529
Leu Asp Ala Phe Val Phe Ile Gly Gly Val Gly Ala Gln Tyr Gly Asp
            155                 160                 165 acc gga cgg tgg att ttc gcc gct ggc gcg ttc gcg gca agc ctg atc      577
Thr Gly Arg Trp Ile Phe Ala Ala Gly Ala Phe Ala Ala Ser Leu Ile
        170                 175                 180 tgg ttc ccg ctg gtg ggt ttc ggc gca gca gca ttg tca cgc ccg ctg      625
Trp Phe Pro Leu Val Gly Phe Gly Ala Ala Ala Leu Ser Arg Pro Leu
185                 190                 195 tcc agc ccc aag gtg tgg cgc tgg atc aac gtc gtc gtg gca gtt gtg      673
Ser Ser Pro Lys Val Trp Arg Trp Ile Asn Val Val Val Ala Val Val
200                 205                 210                 215 atg acc gca ttg gcc atc aaa ctg atg ttg atg ggt tag ttttcgcggg       722
Met Thr Ala Leu Ala Ile Lys Leu Met Leu Met Gly
                220                 225 ttttggagct cttctagcag aagagcatac atctggaag                           761

<210> SEQ ID NO 57
<211> LENGTH: 124
<212> TYPE: PRT
<213> ORGANISM: Brevibacterium lactofermentum

<400> SEQUENCE: 57

Met Val Ile Met Glu Ile Phe Ile Thr Gly Leu Leu Leu Gly Ala Ser
```

```
                1               5                  10                 15
Leu Leu Leu Ser Ile Gly Pro Gln Asn Val Leu Val Ile Lys Gln Gly
            20                  25                 30

Ile Lys Arg Glu Gly Leu Ile Ala Val Leu Leu Val Cys Leu Ile Ser
            35                  40                 45

Asp Val Phe Leu Phe Ile Ala Gly Thr Leu Gly Val Asp Leu Leu Ser
            50                  55                 60

Asn Ala Ala Pro Ile Val Leu Asp Ile Met Arg Trp Gly Gly Ile Ala
65                  70                  75                 80

Tyr Leu Leu Trp Phe Ala Val Met Ala Ala Lys Asp Ala Met Thr Asn
                    85                  90                 95

Lys Val Glu Ala Pro Gln Ile Ile Glu Glu Thr Glu Pro Thr Val Pro
            100                 105                110

Asp Asp Thr Pro Leu Gly Val Phe Gly Gly Gly His
            115                 120
```

```
<210> SEQ ID NO 58
<211> LENGTH: 828
<212> TYPE: DNA
<213> ORGANISM: Methylophilus methylotrophus
<220> FEATURE:
<221> NAME/KEY: CDS
<222> LOCATION: (1)..(825)

<400> SEQUENCE: 58
```

| | | | | | | | | | | | | | | | | |
|---|---|---|---|---|---|---|---|---|---|---|---|---|---|---|---|---|
| gtg | aat | aat | aat | atc | tct | tac | agt | ttt | gaa | ttc | ttc | ccg | ccc | aag | acg | 48 |
| Val | Asn | Asn | Asn | Ile | Ser | Tyr | Ser | Phe | Glu | Phe | Phe | Pro | Pro | Lys | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gta | gaa | ggc | atg | gcc | aat | ctg | cgc | aat | gtg | cgc | aat | gag | ctg | gcg | gca | 96 |
| Val | Glu | Gly | Met | Ala | Asn | Leu | Arg | Asn | Val | Arg | Asn | Glu | Leu | Ala | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| ttt | tca | ccc | gaa | ttt | ttc | tcg | gtc | act | ttt | ggc | gca | ggt | ggc | tcc | acg | 144 |
| Phe | Ser | Pro | Glu | Phe | Phe | Ser | Val | Thr | Phe | Gly | Ala | Gly | Gly | Ser | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| cgt | gac | cgt | acc | atg | gaa | agc | gtg | ctg | gaa | atc | cag | gcg | gaa | ggc | cat | 192 |
| Arg | Asp | Arg | Thr | Met | Glu | Ser | Val | Leu | Glu | Ile | Gln | Ala | Glu | Gly | His | |
| | 50 | | | | | 55 | | | | | 60 | | | | | |

| | | | | | | | | | | | | | | | | |
|---|---|---|---|---|---|---|---|---|---|---|---|---|---|---|---|---|
| ggg | gca | gca | cct | cat | att | tcc | tgt | att | tcc | tct | agt | aaa | gaa | gaa | att | 240 |
| Gly | Ala | Ala | Pro | His | Ile | Ser | Cys | Ile | Ser | Ser | Ser | Lys | Glu | Glu | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cgt | gag | tta | tta | cag | gct | tat | caa | gcc | aaa | ggc | atc | aag | cga | ctg | gtc | 288 |
| Arg | Glu | Leu | Leu | Gln | Ala | Tyr | Gln | Ala | Lys | Gly | Ile | Lys | Arg | Leu | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| acc | ttg | cgc | ggc | gat | atc | cct | tca | ggc | gaa | gtg | agt | gct | ggc | gat | ttt | 336 |
| Thr | Leu | Arg | Gly | Asp | Ile | Pro | Ser | Gly | Glu | Val | Ser | Ala | Gly | Asp | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| aaa | tat | gcc | aat | gag | ctg | gtg | agt | ttt | atc | cgt | gct | gaa | acc | ggt | gac | 384 |
| Lys | Tyr | Ala | Asn | Glu | Leu | Val | Ser | Phe | Ile | Arg | Ala | Glu | Thr | Gly | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| tgg | ttt | cac | ctc | gaa | gtg | gcg | gct | tac | cct | gag | ttt | cat | ccg | gaa | gca | 432 |
| Trp | Phe | His | Leu | Glu | Val | Ala | Ala | Tyr | Pro | Glu | Phe | His | Pro | Glu | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| ggt | tct | gca | caa | aaa | gac | ctg | gaa | aac | ttc | aaa | cgt | aaa | atc | gat | gcc | 480 |
| Gly | Ser | Ala | Gln | Lys | Asp | Leu | Glu | Asn | Phe | Lys | Arg | Lys | Ile | Asp | Ala | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggt | gcc | gat | tct | gcc | att | acg | cag | tac | ttt | tac | aat | atg | gat | gcg | tat | 528 |
| Gly | Ala | Asp | Ser | Ala | Ile | Thr | Gln | Tyr | Phe | Tyr | Asn | Met | Asp | Ala | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| ttc | cgt | ttt | gtg | gaa | gcg | gcg | caa | aaa | atg | ggt | gtt | aca | gcg | cct | atc | 576 |
| Phe | Arg | Phe | Val | Glu | Ala | Ala | Gln | Lys | Met | Gly | Val | Thr | Ala | Pro | Ile | |

```
                                180                 185                 190
att ccc ggc atc atg ccg atc tac aat tac acg cag ctg gcg cgt ttt      624
Ile Pro Gly Ile Met Pro Ile Tyr Asn Tyr Thr Gln Leu Ala Arg Phe
        195                 200                 205 tcc aat gta tgt ggt gca gag att cca cgc tgg ttg cgt tta cgt ctg      672
Ser Asn Val Cys Gly Ala Glu Ile Pro Arg Trp Leu Arg Leu Arg Leu
    210                 215                 220 gaa gct tat ggt gat gac ttg gct tca tta cgt gct ttt ggc gtg gat      720
Glu Ala Tyr Gly Asp Asp Leu Ala Ser Leu Arg Ala Phe Gly Val Asp
225                 230                 235                 240 gta gtc acc gat att tgc gcc aag ctg att gcg tct ggc gtg gat aaa      768
Val Val Thr Asp Ile Cys Ala Lys Leu Ile Ala Ser Gly Val Asp Lys
                245                 250                 255 atg cat ttc tat acg ctg aac cag gct ggc att att ggc cag att atc      816
Met His Phe Tyr Thr Leu Asn Gln Ala Gly Ile Ile Gly Gln Ile Ile
            260                 265                 270 cgg caa ctg taa                                                      828
Arg Gln Leu
        275

<210> SEQ ID NO 59
<211> LENGTH: 275
<212> TYPE: PRT
<213> ORGANISM: Methylophilus methylotrophus

<400> SEQUENCE: 59

Val Asn Asn Asn Ile Ser Tyr Ser Phe Glu Phe Phe Pro Pro Lys Thr
1               5                   10                  15

Val Glu Gly Met Ala Asn Leu Arg Asn Val Arg Asn Glu Leu Ala Ala
            20                  25                  30

Phe Ser Pro Glu Phe Phe Ser Val Thr Phe Gly Ala Gly Gly Ser Thr
        35                  40                  45

Arg Asp Arg Thr Met Glu Ser Val Leu Glu Ile Gln Ala Glu Gly His
    50                  55                  60

Gly Ala Ala Pro His Ile Ser Cys Ile Ser Ser Lys Glu Glu Ile
65                  70                  75                  80

Arg Glu Leu Leu Gln Ala Tyr Gln Ala Lys Gly Ile Lys Arg Leu Val
                85                  90                  95

Thr Leu Arg Gly Asp Ile Pro Ser Gly Glu Val Ser Ala Gly Asp Phe
            100                 105                 110

Lys Tyr Ala Asn Glu Leu Val Ser Phe Ile Arg Ala Glu Thr Gly Asp
        115                 120                 125

Trp Phe His Leu Glu Val Ala Ala Tyr Pro Glu Phe His Pro Glu Ala
    130                 135                 140

Gly Ser Ala Gln Lys Asp Leu Glu Asn Phe Lys Arg Lys Ile Asp Ala
145                 150                 155                 160

Gly Ala Asp Ser Ala Ile Thr Gln Tyr Phe Tyr Asn Met Asp Ala Tyr
                165                 170                 175

Phe Arg Phe Val Glu Ala Ala Gln Lys Met Gly Val Thr Ala Pro Ile
            180                 185                 190

Ile Pro Gly Ile Met Pro Ile Tyr Asn Tyr Thr Gln Leu Ala Arg Phe
        195                 200                 205

Ser Asn Val Cys Gly Ala Glu Ile Pro Arg Trp Leu Arg Leu Arg Leu
    210                 215                 220

Glu Ala Tyr Gly Asp Asp Leu Ala Ser Leu Arg Ala Phe Gly Val Asp
225                 230                 235                 240

Val Val Thr Asp Ile Cys Ala Lys Leu Ile Ala Ser Gly Val Asp Lys
```

```
                        245                 250                     255
Met His Phe Tyr Thr Leu Asn Gln Ala Gly Ile Ile Gly Gln Ile Ile
                260                 265                 270

Arg Gln Leu
        275
```